United States Patent
Khoshakhlagh et al.

(10) Patent No.: US 12,195,756 B2
(45) Date of Patent: Jan. 14, 2025

(54) METHODS AND COMPOSITIONS FOR THE PRODUCTION OF OLIGODENDROCYTE PROGENITOR CELLS

(71) Applicant: President and Fellows of Harvard College, Cambridge, MA (US)

(72) Inventors: Parastoo Khoshakhlagh, Cambridge, MA (US); Hon Man Alex Ng, Cambridge, MA (US); George M. Church, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 18/437,775

(22) Filed: Feb. 9, 2024

(65) Prior Publication Data

US 2024/0254437 A1    Aug. 1, 2024

Related U.S. Application Data

(63) Continuation of application No. 16/768,348, filed as application No. PCT/US2018/063245 on Nov. 30, 2018, now Pat. No. 12,031,153.

(60) Provisional application No. 62/624,000, filed on Jan. 30, 2018, provisional application No. 62/593,560, filed on Dec. 1, 2017.

(51) Int. Cl.
*C12N 5/0735* (2010.01)
*C12N 15/86* (2006.01)
*C12N 15/90* (2006.01)

(52) U.S. Cl.
CPC ........... *C12N 5/0606* (2013.01); *C12N 15/86* (2013.01); *C12N 15/90* (2013.01); *C12N 2501/602* (2013.01); *C12N 2501/603* (2013.01); *C12N 2506/45* (2013.01); *C12N 2800/90* (2013.01)

(58) Field of Classification Search
CPC ............................... C12N 5/0606; C12N 15/86
See application file for complete search history.

(56) References Cited

U.S. PATENT DOCUMENTS

| | | |
|---|---|---|
| 7,812,124 B2 | 10/2010 | Palm |
| 9,057,053 B2 | 6/2015 | Wernig et al. |
| 9,273,119 B2 | 3/2016 | Maizels et al. |
| 9,487,757 B2 | 11/2016 | Tesar et al. |
| 9,732,128 B2 | 8/2017 | West et al. |
| 11,788,131 B2 | 10/2023 | Ng et al. |
| 11,845,960 B2 | 12/2023 | Ng et al. |
| 12,031,153 B2 | 7/2024 | Khoshakhlagh et al. |
| 2003/0092009 A1 | 5/2003 | Palm |
| 2004/0219575 A1 | 11/2004 | Neuman et al. |
| 2007/0161023 A1 | 7/2007 | Palm |
| 2009/0176724 A1 | 7/2009 | Shen et al. |
| 2010/0093092 A1 | 4/2010 | Bamdad et al. |
| 2010/0159595 A1 | 6/2010 | Zhang et al. |
| 2011/0154518 A1 | 6/2011 | Kim et al. |
| 2012/0070419 A1 | 3/2012 | Christiansen-Weber |
| 2012/0107284 A1 | 5/2012 | Kozlova |
| 2012/0129262 A1 | 5/2012 | West et al. |
| 2012/0157474 A1 | 6/2012 | Dreyfuss et al. |
| 2012/0207744 A1 | 8/2012 | Mendlein et al. |
| 2013/0022583 A1 | 1/2013 | Wernig et al. |
| 2013/0029423 A1 | 1/2013 | Yamanaka et al. |
| 2013/0160152 A1 | 6/2013 | Ostertag et al. |
| 2013/0309769 A1 | 11/2013 | Benvenisty et al. |
| 2013/0330825 A1 | 12/2013 | Couture et al. |
| 2014/0170752 A1 | 6/2014 | Pulst et al. |
| 2014/0234971 A1 | 8/2014 | Slukvin et al. |
| 2015/0044187 A1 | 2/2015 | Visel et al. |
| 2015/0284681 A1 | 10/2015 | Wernig et al. |
| 2015/0352154 A1 | 12/2015 | Goldman et al. |
| 2016/0010056 A1 | 1/2016 | Nakaki et al. |
| 2016/0038544 A1 | 2/2016 | Keller et al. |
| 2016/0201053 A1 | 7/2016 | Maizels et al. |
| 2016/0237402 A1 | 8/2016 | Tilly et al. |
| 2017/0087192 A1 | 3/2017 | Tilly et al. |
| 2018/0127714 A1 | 5/2018 | Ko |
| 2018/0289748 A9 | 10/2018 | Tilly et al. |
| 2019/0017032 A1 | 1/2019 | Firas et al. |
| 2019/0099452 A1 | 4/2019 | Jiang et al. |
| 2019/0233795 A1 | 8/2019 | Ng et al. |
| 2020/0063105 A1 | 2/2020 | Ng et al. |
| 2021/0054448 A1 | 2/2021 | Ng et al. |
| 2021/0171902 A1 | 6/2021 | Khoshakhlagh et al. |

(Continued)

FOREIGN PATENT DOCUMENTS

| | | |
|---|---|---|
| CN | 102796696 A | 11/2012 |
| CN | 106456672 A | 2/2017 |

(Continued)

OTHER PUBLICATIONS

Gorris et al., Pluripotent stem cell-derived radial glia-like cells as stable intermediate for efficient generation of human oligodendrocytes. Glia, vol. 63, No. 12 (Dec. 2015) pp. 2152-2167. (Year: 2015).*
[No Author Listed], Genbank Submission; NIH/NCBI, Accession No. EF587698. Jul. 16, 2007. 2 pages.
[No Author Listed], Genbank Submission; NIH/NCBI, Accession No. NM_203289. Dec. 28, 2019. 4 pages.
[No Author Listed], Genbank Submission; NIH/NCBI, Accession No. EF687698. Dec. 8, 2016. 1 page.
[No Author Listed], Genbank Submission; NIH/NCBI, Accession No. NM_000572. Sep. 9, 2016. 3 pages.
[No Author Listed], Genbank Submission; NIH/NCBI, Accession No. NM_000572. Dec. 31, 2019. 3 pages.
[No Author Listed], Genbank Submission; NIH/NCBI, Accession No. NM_000572.2. Nov. 20, 2017. 3 pages.

(Continued)

*Primary Examiner* — Kara D Johnson
(74) *Attorney, Agent, or Firm* — Wolf, Greenfield & Sacks, P.C.

(57) ABSTRACT

Provided herein are pluripotent stem cells comprising particular combinations of transcription factor for the production of oligodendrocyte progenitor cells (OPCs). Also provided herein are methods of producing the pluripotent stem cells and methods of using the pluripotent stem cells to produce (OPCs) and oligodendrocytes.

19 Claims, 24 Drawing Sheets

Specification includes a Sequence Listing.

(56) References Cited

U.S. PATENT DOCUMENTS

| | | |
|---|---|---|
| 2022/0204926 A1 | 6/2022 | Ng et al. |
| 2024/0117312 A1 | 4/2024 | Ng et al. |
| 2024/0209321 A1 | 6/2024 | Ng et al. |
| 2024/0209435 A1 | 6/2024 | Ng et al. |

FOREIGN PATENT DOCUMENTS

| | | | |
|---|---|---|---|
| CN | 109072200 A | 12/2018 | |
| EP | 3118306 A1 | 1/2017 | |
| JP | 2021-040578 A | 3/2021 | |
| WO | WO 2004/060302 A2 | 7/2004 | |
| WO | WO 2006/005043 A2 | 1/2006 | |
| WO | WO 2008/153568 A1 | 12/2008 | |
| WO | WO 2009/029315 A2 | 3/2009 | |
| WO | WO 2009/029315 A9 | 5/2009 | |
| WO | WO 2009/137674 A2 | 11/2009 | |
| WO | WO 2009/137844 A2 | 11/2009 | |
| WO | WO 2011/091048 A1 | 7/2011 | |
| WO | WO 2012/054896 A1 | 4/2012 | |
| WO | WO 2013/124309 A1 | 8/2013 | |
| WO | WO 2013/170146 A1 | 11/2013 | |
| WO | WO 2015/049677 A1 | 4/2015 | |
| WO | WO 2015/084908 A1 | 6/2015 | |
| WO | WO 2015/179822 A1 | 11/2015 | |
| WO | WO 2016/012570 A1 | 1/2016 | |
| WO | WO 2016/103269 A1 | 6/2016 | |
| WO | WO 2016/120493 A1 | 8/2016 | |
| WO | WO-2016163958 A1 * | 10/2016 | ............ C12N 15/85 |
| WO | WO 2017/015075 A1 | 1/2017 | |
| WO | WO 2018/049382 A1 | 3/2018 | |
| WO | WO 2018/204262 A1 | 11/2018 | |
| WO | WO 2019/108894 A1 | 6/2019 | |
| WO | WO 2020/243392 A1 | 12/2020 | |
| WO | WO 2020/243643 A1 | 12/2020 | |

OTHER PUBLICATIONS

[No Author Listed], Genbank Submission; NIH/NCBI, Accession No. NM_001173531. Dec. 28, 2019. 4 pages.

[No Author Listed], Genbank Submission; NIH/NCBI, Accession No. NM_001285986. Dec. 28, 2019. 4 pages.

[No Author Listed], Genbank Submission; NIH/NCBI, Accession No. NM_001285987. Dec. 28, 2019. 4 pages.

[No Author Listed], Genbank Submission; NIH/NCBI, Accession No. NM_002176. Dec. 31, 2019. 3 pages.

[No Author Listed], Genbank Submission; NIH/NCBI, Accession No. NM_002701. Dec. 31, 2019. 5 pages.

[No Author Listed], Genbank Submission; NIH/NCBI, Accession No. NM_005806. Sep. 27, 2019. 3 Pages.

[No Author Listed], Genbank Submission; NIH/NCBI, Accession No. NM_006168. Aug. 2, 2019. 3 pages.

[No Author Listed], Genbank Submission; NIH/NCBI, Accession No. NM_152568. Oct. 23, 2019. 3 pages.

[No Author Listed], Genbank Submission; NIH/NCBI, Accession No. NM_177400. Oct. 1, 2019. 3 pages.

[No Author Listed], Genbank Submission; NIH/NCBI, Accession No. Z46629. Oct. 7, 2008. 3 pages.

[No Author Listed], ORFeome Collaboration. The ORFeome Collaboration: a genome-scale human ORF-clone resource. Nat Methods. Mar. 2016;13(3):191-2. doi: 10.1038/nmeth.3776.

[No Author Listed], Origene, Product datasheet for RC211285L1, BAPX1 (NKX3-2) (NM_001189) Human Tagged ORF Clone. Retrieved Nov. 15, 2022. https://www.origene.com/catalog/cdna-clones/expression-plasmids/rc21128511/bapx1-nkx3-2-nm_001189-human-tagged-orf-clone.

Abed et al., Transplantation of macaca cynomolgus iPS-derived hematopoietic cells in NSG immunodeficient mice. Haematologica. Oct. 2015;100(10):e428-31. Epub Jun. 18, 2015.

Adamson et al., A Multiplexed Single-Cell CRISPR Screening Platform Enables Systematic Dissection of the Unfolded Protein Response. Cell. Dec. 1, 2016;167(7):1867-1882.e21. doi: 10.1016/j.cell.2016.11.048.

Benabdellah et al., Development of an all-in-one lentiviral vector system based on the original TetR for the easy generation of Tet-ON cell lines. PLoS One. 2011;6(8):e23734. Epub Aug. 18, 2011.

Beneviste et al., Type I interferons as anti-inflammatory mediators. Sci STKE. Dec. 11, 2007;2007(416):pe70.

Bornsen et al., Endogenous interferon-β-inducible gene expression and interferon-β-treatment are associated with reduced T cell responses to myelin basic protein in multiple sclerosis. PLoS One. Mar. 4, 2015;10(3):e0118830. doi: 10.1371/journal.pone.0118830.

Burdo et al., The Maize TFome—development of a transcription factor open reading frame collection for functional genomics. Plant J. Oct. 2014;80(2):356-66. doi: 10.1111/tpj.12623. Epub Aug. 26, 2014.

Busskamp et al., Rapid neurogenesis through transcriptional activation in human stem cells. Mol Syst Biol. Nov. 17, 2014;10:760(1-21). doi: 10.15252/msb.20145508.

Cannella et al., Multiple sclerosis: cytokine receptors on oligodendrocytes predict innate regulation. Ann Neurol. Jan. 2004;55(1):46-57.

Cao et al., Restoring BMP4 expression in vascular endothelial progenitors ameliorates maternal diabetes-induced apoptosis and neural tube defects. Cell Death Dis. Oct. 15, 2020;11(10):859.

Carstens, Identification and nucleotide sequence of the regions of Autographa californica nuclear polyhedrosis virus genome carrying insertion elements derived from Spodoptera frugiperda. Virology. Nov. 1987;161(1):8-17. doi: 10.1016/0042-6822(87)90165-6.

Casey et al., Intrinsic DNA binding properties demonstrated for lineage-specifying basic helix-loop-helix transcription factors. Genome Res. Apr. 2018;28(4):484-496. doi: 10.1101/gr.224360.117. Epub Mar. 2, 2018.

Chanda et al., Generation of induced neuronal cells by the single reprogramming factor ASCL1. Stem Cell Reports. Aug. 12, 2014;3(2):282-96. doi: 10.1016/j.stemcr.2014.05.020. Epub Jul. 4, 2014.

Chavez et al., Comparative analysis of Cas9 activators across multiple species. Nat Methods. Jul. 2016;13(7):563-567. doi: 10.1038/nmeth.3871. Epub May 23, 2016. Author Manuscript, 16 pages.

Chavez et al., Highly efficient Cas9-mediated transcriptional programming. Nat Methods. Apr. 2015;12(4):326-8. doi: 10.1038/nmeth.3312. Epub Mar. 2, 2015. Author Manuscript, 11 pages.

Chen et al., Inducing goat pluripotent stem cells with four transcription factor mRNAs that activate endogenous promoters. BMC Biotechnol. 2017;17(1):11(1-10). Published Feb. 13, 2017. doi:10.1186/s12896-017-0336-7.

Choi et al., A comparison of genetically matched cell lines reveals the equivalence of human iPSCs and ESCs. Nat Biotechnol. Nov. 2015;33(11):1173-81. doi: 10.1038/nbt.3388. Epub Oct. 26, 2015. Author Manuscript, 22 pages.

Darr et al., Overexpression of NANOG in human ES cells enables feeder-free growth while inducing primitive ectoderm features. Development. Mar. 2006;133(6):1193-201.

Dendrou et al., Immunopathology of multiple sclerosis. Nat Rev Immunol. Sep. 15, 2015;15(9):545-58. doi: 10.1038/nri3871. Epub Aug. 7, 2015.

Dixit et al., Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.

Douvaras et al., Generation and isolation of oligodendrocyte progenitor cells from human pluripotent stem cells. Nat Protoc. Aug. 2015;10(8):1143-54. doi: 10.1038/nprot.2015.075. Epub Jul. 2, 2015.

Ehrlich et al., Rapid and efficient generation of oligodendrocytes from human induced pluripotent stem cells using transcription factors. Proc Natl Acad Sci U S A. Mar. 14, 2017;114(11):E2243-E2252. doi: 10.1073/pnas.1614412114. Epub Feb. 28, 2017.

Fraser et al., Acquisition of Host Cell DNA Sequences by Baculoviruses: Relationship Between Host DNA Insertions and FP Mutants of Autographa californica and Galleria mellonella Nuclear Polyhedrosis Viruses. J Virol. Aug. 1983;47(2):287-300. doi: 10.1128/JVI.47.2.287-300.1983.

Garcia-Leon et al., SOX10 Single Transcription Factor-Based Fast and Efficient Generation of Oligodendrocytes from Human Pluripotent

(56) References Cited

OTHER PUBLICATIONS

Stem Cells. Stem Cell Reports. Feb. 13, 2018;10(2):655-672. doi: 10.1016/j.stemcr.2017.12.014. Epub Jan. 11, 2018.
Gohl et al., Large-scale mapping of transposable element insertion sites using digital encoding of sample identity. Genetics. Mar. 2014;196(3):615-23. doi: 10.1534/genetics.113.159483. Epub Dec. 27, 2013.
Goldenberg, Multiple Sclerosis Review. P T. Mar. 2012;37(3):175-84.
Goldman et al., How to make an oligodendrocyte. Development. Dec. 1, 2015;142(23):3983-95. doi: 10.1242/dev.126409.
Goparaju et al., Rapid differentiation of human pluripotent stem cells into functional neurons by mRNAs encoding transcription factors. Sci Rep. Feb. 13, 2017;7:42367(1-12). doi: 10.1038/srep42367.
Gorbacheva et al., Improved transposon-based library preparation for the Ion Torrent platform. Biotechniques. Apr. 1, 2015;58(4):200-2. doi: 10.2144/000114277.
Gorris et al., Pluripotent stem cell-derived radial glia-like cells as stable intermediate for efficient generation of human oligodendrocytes. Glia. Dec. 2015;63(12):2152-67. doi: 10.1002/glia.22882. Epub Jun. 30, 2015.
Gradwohl et al., neurogenin3 is required for the development of the four endocrine cell lineages of the pancreas. Proc Natl Acad Sci U S A. Feb. 15, 2000;97(4):1607-11.
Haenebalcke et al., The ROSA26-iPSC mouse: a conditional, inducible, and exchangeable resource for studying cellular (De)differentiation. Cell Rep. Feb. 21, 2013;3(2):335-41. doi: 10.1016/j.celrep.2013.01.016. Epub Feb. 7, 2013.
Hou et al., Sleeping Beauty transposon system for genetic etiological research and gene therapy of cancers. Cancer Biol Ther. 2015;16(1):8-16. doi: 10.4161/15384047.2014.986944.
Hsieh et al., PKCalpha expression regulated by Elk-1 and MZF-1 in human HCC cells. Biochem Biophys Res Commun. 2006;339(1):217-225. doi:10.1016/j.bbrc.2005.11.015.
Hui et al., Isolation and functional characterization of the human gene encoding the myeloid zinc finger protein MZF-1. Biochemistry. 1995;34(50):16493-16502. doi:10.1021/bi00050a033.
Ikuno et al., Correction: efficient and robust differentiation of endothelial cells from human induced pluripotent stem cells via lineage control with VEGF and cyclic AMP. PLoS One. Apr. 17, 2017;12(4):e0176238. Erratum for: PLoS One. Mar. 13, 2017;12(3):e0173271.
Ivics et al., Molecular reconstruction of Sleeping Beauty, a Tc1-like transposon from fish, and its transposition in human cells. Cell. Nov. 14, 1997;91(4):501-10. doi: 10.1016/s0092-8674(00)80436-5.
Jackman et al., Oligodendrocyte development and myelin biogenesis: parsing out the roles of glycosphingolipids. Physiology (Bethesda). Oct. 2009;24:290-7. doi: 10.1152/physiol.00016.2009.
Jaitin et al., Dissecting Immune Circuits by Linking CRISPR-Pooled Screens with Single-Cell RNA-Seq. Cell. Dec. 15, 2016;167(7):1883-1896.e15. doi: 10.1016/j.cell.2016.11.039.
Kim et al., Oct4-induced oligodendrocyte progenitor cells enhance functional recovery in spinal cord injury model. Embo J. Oct. 23, 2015;34(23):2971-83.
Kim et al., Selective depletion of SSEA-3- and TRA-1-60-Positive undifferentiated human embryonic stem cells by magnetic activated cell sorter (MACS). Tissue Eng. and Regen. Med. 2011;8(2):253-261.
Klein et al., Droplet barcoding for single-cell transcriptomics applied to embryonic stem cells. Cell. May 21, 2015;161(5):1187-1201 and Supplemental Info. doi: 10.1016/j.cell.2015.04.044.
Klose et al., Suppression of experimental autoimmune encephalomyelitis by interleukin-10 transduced neural stem/progenitor cells. J Neuroinflammation. Sep. 22, 2013;10:117. doi: 10.1186/1742-2094-10-117.
Klum et al., Sequentially acting SOX proteins orchestrate astrocyte- and oligodendrocyte-specific gene expression. EMBO Rep. Nov. 2018;19(11):e46635. Epub Aug. 30, 2018.
Kojo et al., Priming of lineage-specifying genes by Bcl11b is required for lineage choice in post-selection thymocytes. Nat Commun. Sep. 26, 2017;8(1):702. doi: 10.1038/s41467-017-00768-1.
Levy et al., mRNA-engineered mesenchymal stem cells for targeted delivery of interleukin-10 to sites of inflammation. Blood. Oct. 3, 2013;122(14):e23-32. doi: 10.1182/blood-2013-04-495119. Epub Aug. 26, 2013.
Li et al., Neural Stem Cells Engineered to Express Three Therapeutic Factors Mediate Recovery from Chronic Stage CNS Autoimmunity. Mol Ther. Aug. 2016;24(8):1456-69. doi: 10.1038/mt.2016.104. Epub May 16, 2016.
Liao et al., Mesenchymal stem cells engineered to express selectin ligands and IL-10 exert enhanced therapeutic efficacy in murine experimental autoimmune encephalomyelitis. Biomaterials. Jan. 2016;77:87-97. doi: 10.1016/j.biomaterials.2015.11.005. Epub Nov. 10, 2015.
Macosko et al., Highly Parallel Genome-wide Expression Profiling of Individual Cells Using Nanoliter Droplets. Cell. May 21, 2015;161(5):1202-1214. doi: 10.1016/j.cell.2015.05.002.
Makar et al., Stem cell based delivery of IFN-beta reduces relapses in experimental autoimmune encephalomyelitis. J Neuroimmunol. May 30, 2008;196(1-2):67-81. doi: 10.1016/j.jneuroim.2008.02.014. Epub May 8, 2008.
Mohammadzadeh et al., Evaluation of AD-MSC (adipose-derived mesenchymal stem cells) as a vehicle for IFN-β delivery in experimental autoimmune encephalomyelitis. Clin Immunol. Aug. 2016;169:98-106. doi: 10.1016/j.clim.2016.06.015. Epub Jul. 1, 2016.
Morris et al., The myeloid zinc finger gene, MZF-1, regulates the CD34 promoter in vitro. Blood. 1995;86(10):3640-3647.
Mulvaney et al., Atoh1, an essential transcription factor in neurogenesis and intestinal and inner ear development: function, regulation, and context dependency. J Assoc Res Otolaryngol. Jun. 2012;13(3):281-93. doi: 10.1007/s10162-012-0317-4. Epub Feb. 28, 2012.
Najm et al., Transcription factor-mediated reprogramming of fibroblasts to expandable, myelinogenic oligodendrocyte progenitor cells. Nat Biotechnol. May 2013;31(5):426-33. doi: 10.1038/nbt.2561. Epub Apr. 14, 2013.
Neman et al., A method for deriving homogenous population of oligodendrocytes from mouse embryonic stem cells. Dev Neurobiol. Jun. 2012;72(6):777-88. doi: 10.1002/dneu.22008.
Ng et al., A comprehensive library of human transcription factors for cell fate engineering. Nat Biotechnol. Apr. 2021;39(4):510-519. Epub Nov. 30, 2020. Author Manuscript, 37 pages.
Ng, Differentiation of Human Cells and Tissues Using a Comprehensive Human Transcription Factor Library. Doctoral dissertation, Harvard University, Graduate School of Arts & Sciences. 2018. Retrieved from https://dash.harvard.edu/handle/1/41129209. 105 pages.
Nishiyama et al., Uncovering early response of gene regulatory networks in ESCs by systematic induction of transcription factors. Cell Stem Cell. Oct. 2, 2009;5(4):420-33. doi: 10.1016/j.stem.2009.07.012. Author Manuscript, 23 pages.
Oestreich et al., Master regulators or lineage-specifying? Changing views on CD4+ T cell transcription factors. Nat Rev Immunol. Nov. 2012;12(11):799-804. doi: 10.1038/nri3321. Epub Oct. 12, 2012.
Opal et al., Anti-inflammatory cytokines. Chest. Apr. 2000;117(4):1162-72.
Pagliuca et al., Generation of functional human pancreatic β cells in vitro. Cell. Oct. 9, 2014;159(2):428-39. doi: 10.1016/j.cell.2014.09.040. Author Manuscript, 29 pages.
Pashai et al., Genome-wide profiling of pluripotent cells reveals a unique molecular signature of human embryonic germ cells. PLoS One. 2012;7(6):e39088(1-19). doi:10.1371/journal.pone.0039088.
Patsch et al., Generation of vascular endothelial and smooth muscle cells from human pluripotent stem cells. Nat Cell Biol. Aug. 2015;17(8):994-1003. Epub Jul. 27, 2015. Supplementary Information, 9 pages.
Perrotti et al., Overexpression of the zinc finger protein MZF1 inhibits hematopoietic development from embryonic stem cells: correlation with negative regulation of CD34 and c-myb promoter activity. Mol Cell Biol. 1995;15(11):6075-6087. doi:10.1128/mcb.15.11.6075.

(56) References Cited

OTHER PUBLICATIONS

Pozniak et al., Sox10 directs neural stem cells toward the oligodendrocyte lineage by decreasing Suppressor of Fused expression. Proc Natl Acad Sci U S A. Dec. 14, 2010;107(50):21795-800. Epub Nov. 22, 2010.

Rufaihah et al., Human induced pluripotent stem cell-derived endothelial cells exhibit functional heterogeneity. Am J Transl Res. 2013;5(1):21-35. Epub Jan. 21, 2013.

Rukstalis et al., Neurogenin3: a master regulator of pancreatic islet differentiation and regeneration. Islets. Nov.-Dec. 2009;1(3):177-84. doi: 10.4161/isl.1.3.9877.

Ryu et al., Gene therapy of multiple sclerosis using interferon β-secreting human bone marrow mesenchymal stem cells. Biomed Res Int. 2013;2013:696738. Epub Apr. 22, 2013.

Sagal et al., Proneural transcription factor Atoh1 drives highly efficient differentiation of human pluripotent stem cells into dopaminergic neurons. Stem Cells Transl Med. Aug. 2014;3(8):888-98. doi: 10.5966/sctm.2013-0213. Epub Jun. 5, 2014.

Sarkar et al., The sox family of transcription factors: versatile regulators of stem and progenitor cell fate. Cell Stem Cell. Jan. 3, 2013;12(1):15-30.

Selvaraj et al., Switching cell fate: the remarkable rise of induced pluripotent stem cells and lineage reprogramming technologies. Trends Biotechnol. Apr. 2010;28(4):214-23. doi: 10.1016/j.tibtech.2010.01.002. Epub Feb. 9, 2010.

Simicevic et al., Absolute quantification of transcription factors during cellular differentiation using multiplexed targeted proteomics. Nat Methods. Jun. 2013;10(6):570-6. doi: 10.1038/nmeth.2441. Epub Apr. 14, 2013.

Singari et al., Singari S, Javeed N, Tardi NJ, Marada S, Carlson JC, Kirk S, Thorn JM, Edwards KA. Inducible protein traps with dominant phenotypes for functional analysis of the *Drosophila* genome. Genetics. Jan. 2014;196(1):91-105. doi: 10.1534/genetics.113.157529. Epub Oct. 30, 2013.

Sripal, Combined expression of microRNAs and transcription factors for promoting hair cell differentiation. 2013 Master's Thesis. Department of Biomedical Sciences. Creighton University, 89 pages. Submitted Jul. 29, 2013.

Stolt et al., The Sox9 transcription factor determines glial fate choice in the developing spinal cord. Genes Dev. Jul. 1, 2003;17(13):1677-89.

Suchorska et al., Comparison of Four Protocols to Generate Chondrocyte-Like Cells from Human Induced Pluripotent Stem Cells (hiPSCs). Stem Cell Rev Rep. Apr. 2017;13(2):299-308. doi: 10.1007/s12015-016-9708-y.

Takahashi et al., Induction of pluripotent stem cells from mouse embryonic and adult fibroblast cultures by defined factors. Cell. Aug. 25, 2006;126(4):663-76. Epub Aug. 10, 2006.

Trandem et al., Virally expressed interleukin-10 ameliorates acute encephalomyelitis and chronic demyelination in coronavirus-infected mice. J Virol. Jul. 2011;85(14):6822-31. doi: 10.1128/JVI.00510-11. Epub May 18, 2011.

Trounson, Pluripotent stem cells progressing to the clinic. Nat Rev Mol Cell Biol. Mar. 2016;17(3):194-200. doi: 10.1038/nrm.2016.10.

Van Der Maaten et al., Visualizing Data using t-SNE. J Mach Learn Res. 2008;9(86):2579-2605.

Vaquerizas et al., A census of human transcription factors: function, expression and evolution. Nat Rev Genet. Apr. 2009;10(4):252-63. doi: 10.1038/nrg2538.

Walczak et al., Directed differentiation of human iPSC into insulin producing cells is improved by induced expression of PDX1 and NKX6.1 factors in IPC progenitors. J Transl Med. Dec. 20, 2016;14(1):341. doi: 10.1186/s12967-016-1097-0.

Wang et al., Human iPSC-derived oligodendrocyte progenitor cells can myelinate and rescue a mouse model of congenital hypomyelination. Cell Stem Cell. Feb. 7, 2013;12(2):252-64. doi: 10.1016/j.stem.2012.12.002.

Williams et al., Antibody-mediated inhibition of TNFR1 attenuates disease in a mouse model of multiple sclerosis. PLoS One. Feb. 28, 2014;9(2):e90117. doi: 10.1371/journal.pone.0090117.

Williams et al., SnapShot: directed differentiation of pluripotent stem cells. Cell. May 25, 2012;149(5):1174-1174.e1. doi: 10.1016/j.cell.2012.05.015. 2 pages.

Xiao et al., Mesenchymal stem cells and induced pluripotent stem cells as therapies for multiple sclerosis. Int J Mol Sci. Apr. 24, 2015;16(5):9283-302. doi: 10.3390/ijms16059283.

Yamakawa et al., Screening of Human cDNA Library Reveals Two differentiation-Related Genes, HHEX and HLX, as Promoters of Early Phase Reprogramming toward Pluripotency. Stem Cells. Nov. 2016;34(11):2661-2669. doi: 10.1002/stem.2436. Epub Jul. 8, 2016.

Yamamizu et al., Identification of transcription factors for lineage-specific ESC differentiation. Stem Cell Reports. Dec. 2013;1(6):545-59. doi: 10.1016/j.stemcr.2013.10.006. eCollection 2013.

Yamanaka, Induced pluripotent stem cells: past, present, and future. Cell Stem Cell. Jun. 14, 2012;10(6):678-684. doi: 10.1016/j.stem.2012.05.005.

Yang et al., Adult neural stem cells expressing IL-10 confer potent immunomodulation and remyelination in experimental autoimmune encephalitis. J Clin Invest. Dec. 2009;119(12):3678-91. doi: 10.1172/JCI37914. Epub Nov. 2, 2009.

Yang et al., Generation of oligodendroglial cells by direct lineage conversion. Nat Biotechnol. May 2013;31(5):434-9. doi: 10.1038/nbt.2564. Epub Apr. 14, 2013.

Zhang et al., Rapid single-step induction of functional neurons from human pluripotent stem cells. Neuron. Jun. 5, 2013;78(5):785-98. doi: 10.1016/j.neuron.2013.05.029.

\* cited by examiner

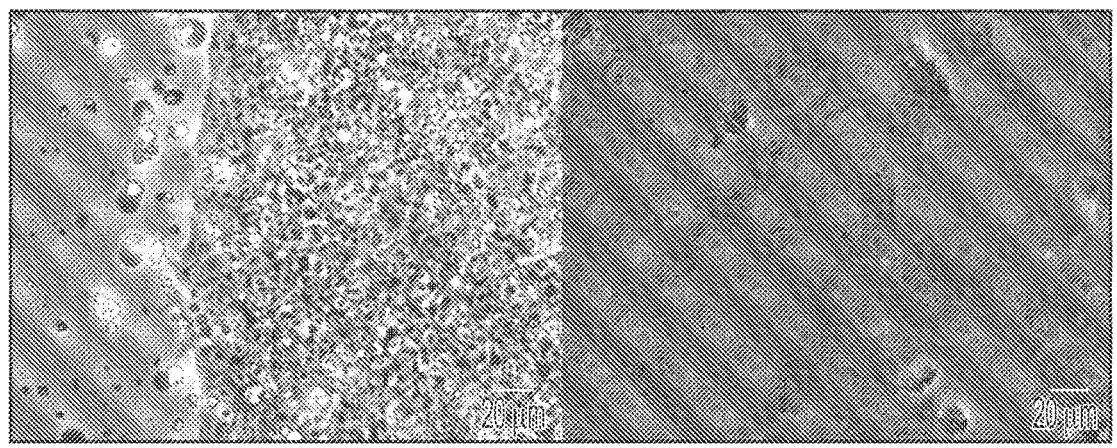
FIG. 2
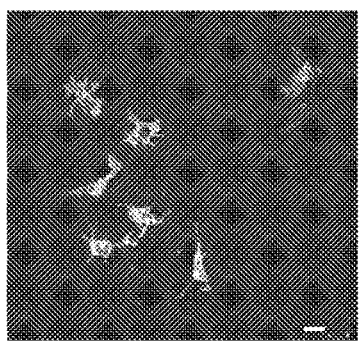 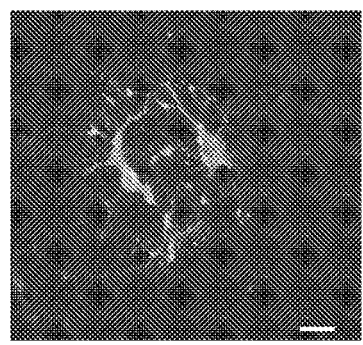 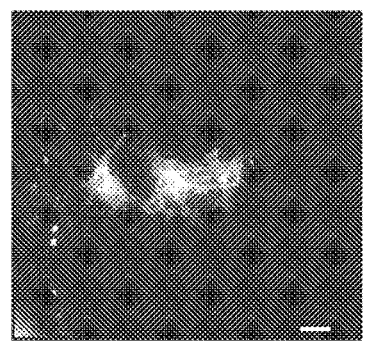
FIG. 3A  FIG. 3B  FIG. 3C

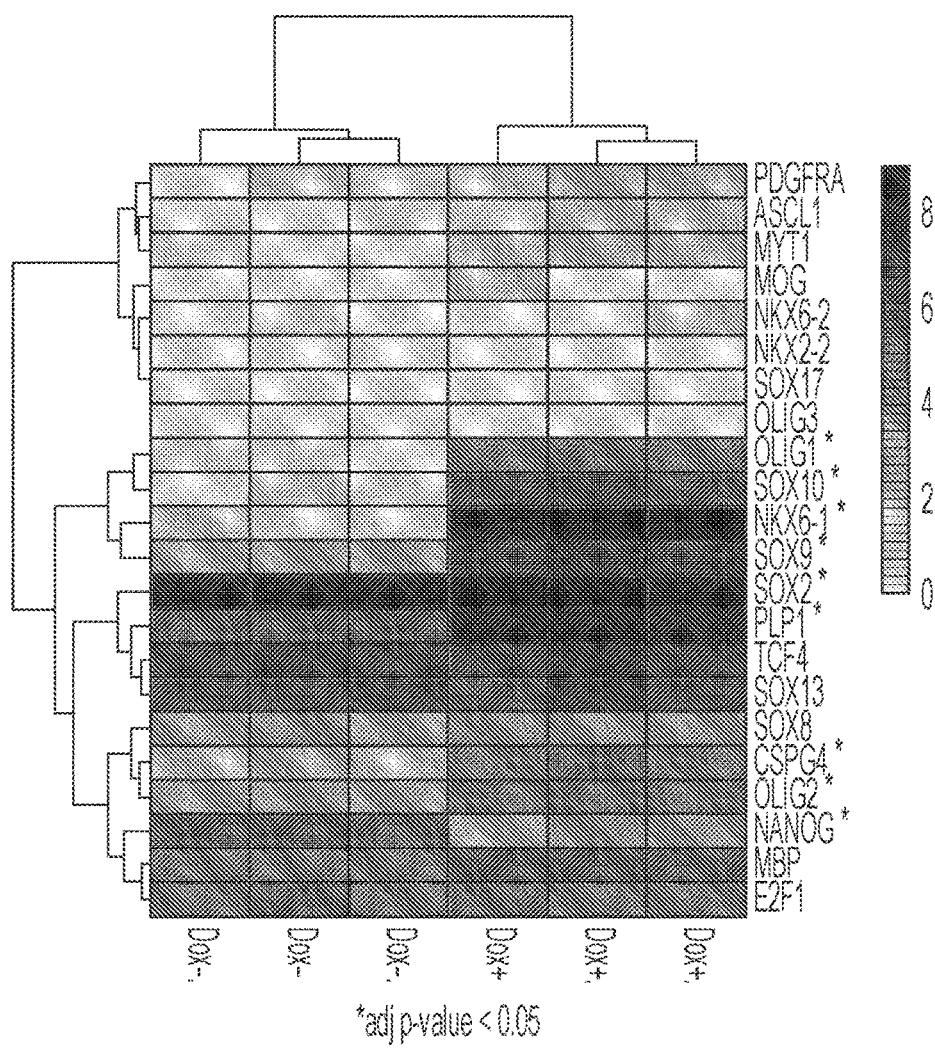
FIG. 8A
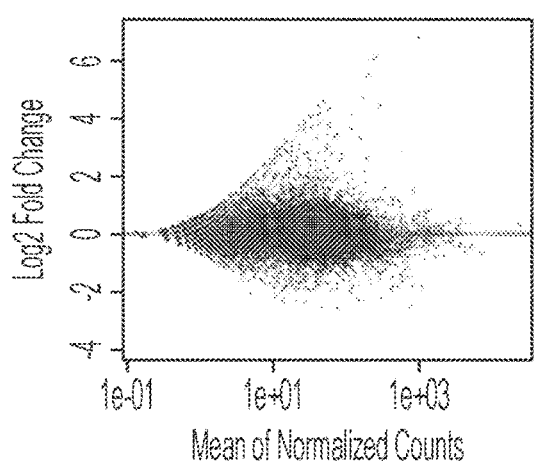
FIG. 8B
FIG. 8C

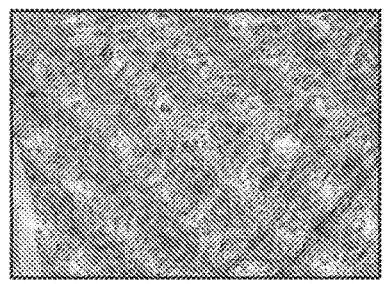 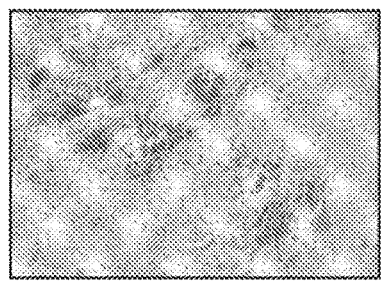 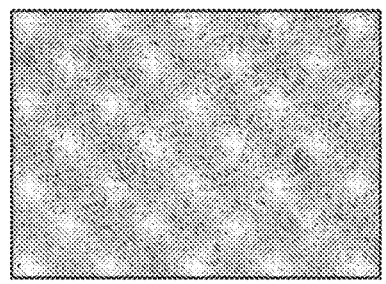
FIG. 17A  FIG. 17B  FIG. 17C
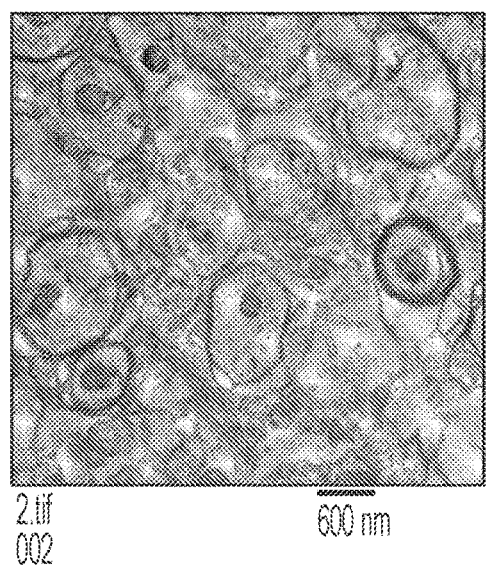
FIG. 18A

METHODS AND COMPOSITIONS FOR THE PRODUCTION OF OLIGODENDROCYTE PROGENITOR CELLS

RELATED APPLICATIONS

This application is a continuation of U.S. application Ser. No. 16/768,348, filed May 29, 2020, which is a national stage filing under 35 U.S.C. § 371 of International Application No. PCT/US2018/063245, filed Nov. 30, 2018, which claims the benefit under 35 U.S.C. § 119(e) of U.S. Provisional Application No. 62/593,560, filed Dec. 1, 2017 and U.S. Provisional Application No. 62/624,000, filed Jan. 30, 2018, each of which is incorporated by reference herein in its entirety.

FEDERALLY SPONSORED RESEARCH

This invention was made with government support under AG048056, HG008525, and MH103910 awarded by National Institutes of Health (NIH). The government has certain rights in the invention.

REFERENCE TO AN ELECTRONIC SEQUENCE LISTING

The contents of the electronic sequence listing (H049870650US03-SEQ-KVC.xml; Size: 16,992 bytes; and Date of Creation: Feb. 6, 2024) is herein incorporated by reference in its entirety.

BACKGROUND

Oligodendrocytes are a subtype of glial cells in the central nervous system that originate from oligodendrocyte progenitor cells (OPCs). OPCs account for about 5% of cells in the central nervous system. Oligodendrocytes help support and insulate axons by producing myelin. Myelin sheaths in the central nervous system are made of extended oligodendrocyte plasma membranes. While mature oligodendrocytes cannot self-renew, OPCs can repopulate oligodendrocytes following injury to the central nervous system in healthy individuals.

Multiple sclerosis is a demyelinating disorder that includes an autoimmune response, which leads to the destruction of (damage to) the myelin sheath made by oligodendrocytes. Overactivated T-cells are thought to be part of this process, leading to a pro-inflammatory profile that results in CNS inflammation. T cells secrete various inflammatory responses such as cytokines (e.g., IFNγ, IL17, etc.), nitric oxide (NO), and glutamate, causing an overstimulation of the immune system and eventual degradation of myelin, oligodendrocytes and axons. Most treatments for demyelinating disorders have focused on reducing symptoms rather than replacing damaged myelin.

SUMMARY

Provided herein, in some embodiments, are pluripotent stem cells and methods for producing oligodendrocyte progenitor cells (OPCs) (e.g., O4-positive OPCs) and myelin-producing oligodendrocytes. In some embodiments, the oligodendrocytes are 'immunoprotective,' meaning they are capable of secreting immunosuppressive factors. Although myelin damage is a hallmark of many demyelinating disorders, treatment options for these disorders are limited due in part to the lack of efficient methods for producing functional OPCs. Further, while cell therapies utilizing transplanted stem cell-derived OPCs may help with remyclination, these exogenous cells can become the target of a heightened inflammatory response, resulting in some instances in limited therapeutic benefit and insignificant improvement in clinical outcome.

The experimental results provided herein show unexpectedly that particular combinations of transcription factors can induce the formation of OPCs, in some embodiments, in as few as four days without optimizing for cell growth and/or differentiation culture conditions. In some embodiments, these stem cell-derived OPCs are also engineered to protect themselves from autoimmune attacks by secreting anti-inflammatory cytokines.

Further, in some embodiments, the methods provided herein improve OPC production yield and shorten production time through the use of a PIGGYBAC™ transposon system, which permits high copy number (e.g., 5 to 50 copies) integration of nucleic acids into a host genome.

Accordingly, some aspects of the present disclosure provide pluripotent stem cells (e.g., induced pluripotent stem cells) that include at least three transcription factors selected from the following transcription factors: (a) an oligodendrocyte (OLIG) transcription factor. (b) an SRY-box (SOX) transcription factor, (c) two NKX homeobox transcription factors, and (d) an octamer-binding (OCT) transcription factor. In some embodiments, the OLIG transcription factor is OLIG2. In some embodiments, the SOX transcription factor is SOX9. In some embodiments, the two NKX homeobox transcription factor are NKX6.1 and NKX6.2. In some embodiments, the OCT transcription factor is OCT4 (also referred to as POU5F1 (POU domain, class 5, transcription factor)). In some embodiments, the pluripotent stem cells comprise, consist of: or consist essentially of OLIG2, SOX9, NKX6.1, NKX6.2, and OCT4. In some embodiments, the pluripotent stem cells further include IL-10 and/or IFNβ.

Other aspects of the present disclosure provide methods that include introducing into pluripotent stem cells at least one engineered nucleic acid encoding at least three transcription factors selected from an OLIG transcription factor, a SOX transcription factor, two NKX homeobox transcription factors, and an OCT transcription factor to produce O4 positive OPCs. In some embodiments, the methods further include introducing into pluripotent stem cells at least one engineered nucleic acid encoding IL-10 and/or IFNβ. In some embodiments, the methods further include culturing the OPCs to produce oligodendrocytes.

Yet other aspects of the present disclosure provide pharmaceutical compositions comprising the OPCs or the oligodendrocytes produced by the methods described herein. These pharmaceutical compositions may be used, for example, to treat (e.g., improve) a demyelinating disorder, such as multiple sclerosis.

BRIEF DESCRIPTION OF THE DRAWINGS

FIG. 2 shows data indicating that induction of OLIG2, SOX9, NKX6.1, NKX6.2, and OCT4 transcription factor expression changes the morphology of iPSCs and promotes the differentiation of iPSC cells. The left picture shows the morphology of control iPSCs, in which there is no induction of transcription factor expression (no doxycycline is added to the media). The right picture shows the morphology of iPSCs after doxycycline is added to the cell media to induce expression of the transcription factors. Both pictures were taken after iPSCs were cultured for 4 days (with or without doxycycline). Scale bar=20 µm.

FIGS. 3A-3C show data indicating that induction of OLIG2, SOX9, NKX6.1, and OCT4 transcription factor expression in iPSCs promotes the formation of OPCs and maturation oligodendrocytes. FIG. 3A is a photo showing immunohistochemistry analysis of cells four days after induction of transcription factor expression, using anti-O4 antibody. FIG. 3B is a photo showing immunohistochemistry analysis of cells eight days after induction of transcription factor expression, using anti-O4 antibody. FIG. 3C is a photo showing immunohistochemistry analysis of cells eight days after induction of transcription factor expression, using anti-MOG antibody.

FIG. 4A is a bar graph showing the frequency of O4-positive, NG2-positive, and anti-Galactocerebroside (anti-GalC)-positive OPCs four days after no induction (No Dox) or after induction (Dox) of OLIG2, SOX9, NKX6.1, NKX6.2, and OCT4 transcription factor expression in iPSCs. Data was generated using anti-O4, anti-NG2, and anti-GalC antibodies and fluorescence activated cell sorting (FACS) analysis. FIG. 4B includes transmission electron microscopy images showing robust myelin formation after engineered oligodendrocyte cells were co-cultured for 4 weeks with doxycycline inducible iNGN (Neurogenin-mediated) stem cells. Scale bars on the left two panels indicate 100 nm. Scale bars on the right two panels indicate 200 nm. M indicates myelin, while A indicates axon.

FIG. 7A shows the frequency of O4+ cells in individual colonies that were analyzed from OPC0 and OPC10. Data has not been shown for all the tested samples (n>6). Due to the large volume of colonies screened, no replicates were included. See also FIG. 14G for additional replicates and colonies. FIG. 7B shows the results for the OPC0 colony with the highest O4 marker frequency (Colony #1), which was stained for early (NG2), intermediate proliferative premitotic (O4), and late, non-proliferative post mitotic (GalC) markers after 4 or 8 days of doxycycline induction (suffix -4 or -8 respectively). The first set of bars indicates results with no doxycycline. The second set of bars for each colony indicates results with doxycycline.

FIGS. 8A-8C include RNA-seq data of O4+ cells (from OPC9) compared to uninduced samples. FIG. 8A is a heatmap showing that some of the specific oligodendrocyte markers were up-regulated after 4 days of induction confirming the commitment of the O4+ OPCs to become matured oligodendrocytes. Genes were plotted based on their log 2 fold change compared to hiPSCs and were considered as statistically significant (*) if the adjusted p-value was less than 0.05. The darker the box for each transcription factor, the higher the fold change in gene expression. Dox− indicates the absence of doxycycline treatment (TF expression was not induced). DOX+ indicates addition of doxycycline to induce TF expression. FIG. 8B is a graph showing a comparison of the mean of normalized counts and Log 2 fold change. FIG. 8C is a chart showing the top 40 differentially expressed genes, some of which are oligodendrocyte-specific such as OLIG1 and PLP1.

FIG. 13A shows a vector for over-expressing IL10 and IFNβ with GFP selection. FIG. 13B shows a vector for over-expressing IL10 and IFNβ with puromycin (Puro) selection.

FIG. 14A shows percent of O4-positive cells among the different colonies made by transfecting high amounts of DNA (e.g., ≥1000 ng per 1 million cells). The first set of bars for each colony indicates results with no doxycycline. The second set of bars for each colony indicates results with doxycycline for four days. FIG. 14B shows percent of GalC-positive cells among the different colonies made by transfecting high amounts of DNA. The first set of bars for each colony indicates results with no doxycycline. The second set of bars for each colony indicates results with doxycycline for four days. FIG. 14C shows number of genomically integrated TFs in three colonies made by transfecting high amounts of DNA. This figure shows the total copy number of all integrated transcription factors in the indicated colony. FIG. 14D shows detailed analysis of O4 and GalC expression among the top three colonies made by transfecting high amounts of DNA. FIG. 14E shows number of genomically integrated TFs among colonies made by transfecting low amounts of DNA (e.g., less than 1000 ng per 1 million cells). FIG. 14F shows detailed analysis of O4 and GalC expression in a colony made by transfecting low amounts of DNA. FIG. 14G shows percent of cells expressing NG2, O4 and GalC among colonies made by transfecting low amounts of DNA.

FIG. 15A shows a 3-day co-culture of engineered OPCs interacting with neurites of hiPSC-induced neurons. As shown, OPC is contacting the induced neuron. FIG. 15B shows myelin (M) formation wrapping around an axon (A), demonstrating functionality of the differentiated OPCs after four weeks of co-culture. A portion of the culture was cross-sectioned and imaged using electron microscopy.

FIG. 16A shows that control cerebral organoid mixed with inducible OPCs but not treated with doxycycline did not stain for MBP or MOG. DAPI was used to label nuclei. FIG. 16B shows that cerebral organoids mixed with inducible OPCs and treated with doxycycline to induce differentiation stained positive for MBP and MOG. DAPI was used to label nuclei. FIG. 16C shows that cerebral organoids mixed with inducible OPCs and treated with doxycycline to induce differentiation stained positive for MBP. DAPI was used to label nuclei. MBP staining can be seen as the lighter shading surrounding the center two cells.

FIGS. 17A-17C include brain slice images stained for MBP demonstrating the amount of myelin (darker staining). FIG. 17A shows staining of a sample from a normal mouse. FIG. 17B shows staining of a sample from a mouse injected with engineered OPCs. Cells from OPC0, colony 1, which were engineered to inducibly express OLIG2, SOX9, NKX6.1, NKX6.2, and OCT4, were used. FIG. 17C shows a staining of a sample from an untreated Shiverer mouse.

FIGS. 18A-18D include data quantifying the number of myelinated axons using transmission electron microscopy (TEM) images. FIGS. 18A-18B show TEM images of brain slices from control group where the mice received PBS injections (FIG. 18A) and from a treatment cohort where the mice received cells (FIG. 18B). FIG. 18C shows quantification of the number of myelinated axons in a series of brain slices. FIG. 18D shows G-ratio in injected mice.

FIG. 19A is a graph of the concentration of secreted IL-10 in cells engineered to overexpress doxycycline-dependent OPC-inducing transcription factors (SOX9, NKX6.1, OLIG2, NKX6.2, and OCT4) and doxycycline-dependent IL10. FIG. 19B shows a graph of the concentration of secreted IL-10 in cells engineered to overexpress doxycycline-dependent OPC-inducing transcription factors, doxycycline-dependent IL-10, and doxycycline-dependent IFNβ. (first series of columns: uninduced, second series of columns: induced)

FIG. 21A shows the body weight over time, as days after immunization with anti-MOG T cells. Lighter line represents animals injected with cells. Black line represents animals not injected with cells. Error bars are standard errors of the mean. FIG. 21B shows the EAE clinical score. Lighter line represents animals injected with cells. Black line represents animals not injected with cells. Error bars are standard errors of the mean.

DETAILED DESCRIPTION

Figure 1:
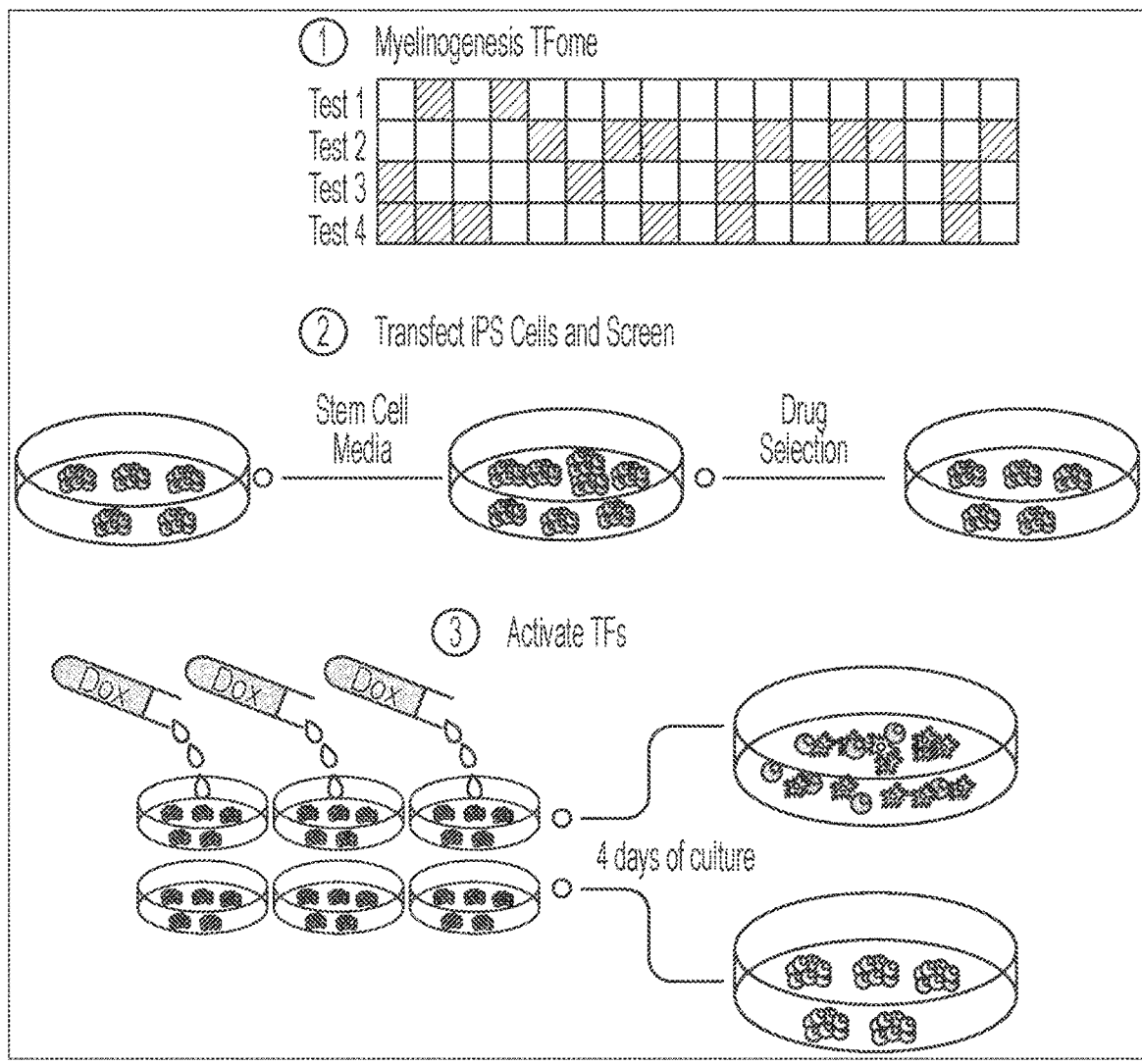
FIG. 1 shows a schematic protocol for directed differentiation of induced pluripotent stem cells (iPSCs) into oligodendrocyte progenitor cells (OPCs).

Induced pluripotent stem cells (iPSCs) are reprogrammed from adult differentiated cells and are capable of developing into many phenotypes. iPSCs may be obtained from a patient and changed into any cell type that is necessary to improve a particular condition, permitting patient-specific autologous clinical applications while simultaneously minimizing the risk of immune response or rejection. Although the use of stem cell therapies for clinical applications such as neurodegenerative and myelin degenerative diseases, myocardial infarction, and bone defect repair have been promising, there are significant limitations relating to uncontrolled proliferation, low cell survival, negative immune responses, differentiation into undesired cell types, inconsistency and long procedure duration. The technology provided herein overcomes many of these limitations. The present disclosure provides methods for transcription factor (TF)-mediated direct reprogramming of stem cells, such as iPSCs, to generate a desired cell type, in some instances, in as few as 1 to 8 days with high efficiency (e.g., at least 50%, at least 60%, at least 70%, at least 80%, or at least 90% of the cells expressing markers of differentiation). For example, cells may be reprogrammed within 2-8, 3-8, or 4-8 days. In some embodiments, a cell may be reprogrammed using the methods described herein in less than 10 days, less than 9 days, less than 8 days, less than 7 days, less than 6 days, less than 5 days, less than 4 days, less than 3 days, less than 2 days, or less than 1 day. In some embodiments cells may be reprogrammed (e.g., express differentiation markers) within 1 day. The present disclosure also provides methods for protecting the desired cell type from the immune (inflammatory) response.

Autoimmune diseases that are the result of dysfunctional immune systems may be amenable to stem cell therapies. Multiple sclerosis (MS), with a worldwide prevalence of approximately 2.5 million people, is an autoimmune disease that is a frequent mesenchymal stem cell (MSC) therapy target. Success to date has been limited, however, largely due to the above-mentioned limitations. Current strategies to overcome the hurdles of stem cell are still largely impractical in application due to the lengthy culture times, complicated culture conditions and low efficiency.

Data provided herein demonstrates that TF-mediated direct reprogramming of iPSCs can be utilized, in some embodiments, to generate O4-positive OPCs while requiring no media regimen optimization. This approach is considerably faster and more efficient than existing reprogramming methods. Data provided herein also shows that these iPSCs and the cells produced from these iPSCs can be programmed to secrete inflammatory cytokines, thus rendering the cells immunoprotective.

The present disclosure is based, at least in part, on unexpected results demonstrating that a specific combination of transcription factors can induce the formation of OPCs. The combination of transcription factors, in some embodiments, comprises at least two (e.g., at least three, least four, or at least five) transcription factors selected from oligodendrocyte (OLIG) transcription factors, SRY-box (SOX) transcription factors, NKX homeobox transcription factors, and octamer-binding (OCT) transcription factors. These OPCs may be used, for example, to rebuild the damaged myelin sheath surrounding axons in subjects having demyelinating disorders.

Oligodendrocyte Progenitor Cells and Oligodendrocytes

Oligodendrocyte progenitor cells (OPCs) are a subtype of glial cells in the central nervous system characterized by expression of the proteoglycans PDGFRA and NG2 (CSPG4). They are precursors to oligodendrocytes, which are neuroglia that function to support and insulate axons by producing a myelin sheath wrapping. While mature oligodendrocytes cannot self-renew, OPCs can repopulate oligodendrocytes following an injury to the central nervous system in healthy individuals.

As stem cells develop into oligodendrocytes, each stage of development may be characterized by specific cell surface markers. For example, the membrane chondroitin sulfate proteoglycan NG2 (CSPG4) may be used as a marker of early-stage proliferative OPCs. Oligodendrocyte marker O4 may be used as an indicator of mid- to late-stage OPCs (Jackman, N et al., *Physiology* (24):290-7 (2009). In some embodiments, OPCs produced by the methods of the present disclosure are mid- to late-stage OPCs that express O4. Myelin Basic Protein (MBP) and Myelin Oligodendrocyte Glycoprotein (MOG) are expressed in terminal differentiation of OPCs to oligodendrocytes. They both are oligodendrocyte-specific genes and may be used as markers of mature oligodendrocytes formation. MOG is a membrane protein found on the surface of oligodendrocyte cells and on the outer layer of myelin sheaths. GalC is a galactosphingolipid of myelin found on oligodendrocyte membranes and may be used as a marker for late stage OPC (post-mitotic) and early mature oligodendrocyte. GalC may be used as a marker of terminal differentiation. In some embodiments, oligodendrocytes produced by the methods of the present disclosure may be mature oligodendrocytes that express MOG and/or GalC. Additional markers of the stages of oligodendrocyte development (e.g., markers for early-stage OPCs, intermediate and late-stage OPCs and mature oligodendrocytes) are known in the art and may be used as provided herein. See e.g., Jackman, N et al., *Physiology* (24):290-7 (2009).

In some embodiments, a OPC comprises an OLIG2 transcription factor and/or a nucleic acid encoding OLIG2. In some embodiments, a OPC comprises an SOX9 transcription factor and/or a nucleic acid encoding SOX9. In some embodiments, a OPC comprises an NKX6.1 transcription factor and/or a nucleic acid encoding NKX6.1. In some embodiments, a OPC comprises an NKX6.2 transcription factor and/or a nucleic acid encoding NKX6.2. In some embodiments, a OPC comprises an OCT4 transcription factor and/or a nucleic acid encoding OCT4.

In some embodiments, a OPC comprises OLIG2 and SOX9. In some embodiments, a OPC comprises OLIG2 and NKX6.1. In some embodiments, a OPC comprises OLIG2 and NKX6.2. In some embodiments, a OPC comprises OLIG2 and OCT4. In some embodiments, a OPC comprises SOX9 and NKX6.1. In some embodiments, a OPC comprises SOX9 and NKX6.2. In some embodiments, a OPC comprises SOX9 and OCT4. In some embodiments, a OPC comprises NKX6.1 and NKX6.2. In some embodiments, a OPC comprises NKX6.1 and OCT4. In some embodiments, a OPC comprises NKX6.2 and OCT4.

In some embodiments, a OPC comprises OLIG2, SOX9 and NKX6.1. In some embodiments, a OPC comprises OLIG2, SOX9 and NKX6.2. In some embodiments, a OPC comprises OLIG2, SOX9 and OCT4. In some embodiments, a OPC comprises OLIG2, NKX6.1 and NKX6.2. In some embodiments, a OPC comprises OLIG2, NKX6.1 and OCT4. In some embodiments, a OPC comprises OLIG2, NKX6.2 and OCT4. In some embodiments, a OPC comprises SOX9, NKX6.1 and NKX6.2. In some embodiments, a OPC comprises SOX9, NKX6.1 and OCT4. In some embodiments, a OPC comprises NKX6.1, NKX6.2 and OCT.

In some embodiments, a OPC comprises at least two transcription factors selected from OLIG2, SOX9, NKX6.1, NKX6.2 and OCT4. In some embodiments, a OPC comprises at least three transcription factors selected from OLIG2, SOX9, NKX6.1, NKX6.2 and OCT4. In some embodiments, a OPC comprises at least four transcription factors selected from OLIG2, SOX9, NKX6.1, NKX6.2 and OCT4. In some embodiments, a OPC comprises OLIG2, SOX9, NKX6.1, NKX6.2 and OCT4.

Pluripotent Stem Cells

Provided herein are methods for reprogramming pluripotent stem cells to produce OPCs (e.g., O4-positive OPCs). Pluripotent stem cells are cells that have the capacity to self-renew by dividing, and to develop into the three primary germ cell layers of the early embryo, and therefore into all cells of the adult body, but not extra-embryonic tissues such as the placenta. Embryonic stem cells (ESCs) and induced pluripotent stem cells (iPSCs) are pluripotent stem cells. ESCs are derived from the undifferentiated inner mass cells of a human embryo and are able to differentiate into all derivatives of the three primary germ layers: ectoderm, endoderm and mesoderm. iPCSs can be generated directly from adult cells (Takahashi, K; Yamanaka. S. *Cell* 126(4): 663-76, 2006). In some embodiments, a pluripotent stem cell is an ESC. In some embodiments, a pluripotent cell is an iPSC. In some embodiments, a pluripotent stem cell is a human ESC. In some embodiments, a pluripotent cell is an iPSC. In some embodiments, a pluripotent cell is a human iPSC.

Pluripotent stem cells, such as an iPSC, may be engineered to express the following transcription factors: (a) an oligodendrocyte (OLIG) transcription factor, (b) an SRY-box (SOX) transcription factor, (c) two NKX homeobox transcription factors, and (d) an octamer-binding (OCT) transcription factor. In some embodiments, a pluripotent stem cell, such as an iPSC, is engineered to express a combination of two or more transcription factors selected from OLIG2, SOX9, NKX6.1, NKX6.2 and OCT4. In some embodiments, a pluripotent stem cell, such as an iPSC, is engineered to express OLIG2, SOX9, NKX6.1, NKX6.2 and OCT4.

In some embodiments, a pluripotent stem cell comprises an OLIG2 transcription factor and/or a nucleic acid encoding OLIG2. In some embodiments, a pluripotent stem cell comprises an SOX9 transcription factor and/or a nucleic acid encoding SOX9. In some embodiments, a pluripotent stem cell comprises an NKX6.1 transcription factor and/or a nucleic acid encoding NKX6.1. In some embodiments, a pluripotent stem cell comprises an NKX6.2 transcription factor and/or a nucleic acid encoding NKX6.2. In some embodiments, a pluripotent stem cell comprises an OCT4 transcription factor and/or a nucleic acid encoding OCT4.

In some embodiments, a pluripotent stem cell comprises OLIG2 and SOX9. In some embodiments, a pluripotent stem cell comprises OLIG2 and NKX6.1. In some embodiments, a pluripotent stem cell comprises OLIG2 and NKX6.2. In some embodiments, a pluripotent stem cell comprises OLIG2 and OCT4. In some embodiments, a pluripotent stem cell comprises SOX9 and NKX6.1. In some embodiments, a pluripotent stem cell comprises SOX9 and NKX6.2. In some embodiments, a pluripotent stein cell comprises SOX9 and OCT4. In some embodiments, a pluripotent stem cell comprises NKX6.1 and NKX6.2. In some embodiments, a pluripotent stem cell comprises NKX6.1 and OCT4. In some embodiments, a pluripotent stem cell comprises NKX6.2 and OCT4.

In some embodiments, a pluripotent stem cell comprises OLIG2, SOX9 and NKX6.1. In some embodiments, a pluripotent stem cell comprises OLIG2, SOX9 and NKX6.2. In some embodiments, a pluripotent stem cell comprises OLIG2, SOX9 and OCT4. In some embodiments, a pluripotent stem cell comprises OLIG2, NKX6.1 and NKX6.2. In some embodiments, a pluripotent stem cell comprises OLIG2, NKX6.1 and OCT4. In some embodiments, a pluripotent stem cell comprises OLIG2, NKX6.2 and OCT4. In some embodiments, a pluripotent stem cell comprises SOX9, NKX6.1 and NKX6.2. In some embodiments, a pluripotent stem cell comprises SOX9, NKX6.1 and OCT4. In some embodiments, a pluripotent stem cell comprises NKX6.1, NKX6.2 and OCT.

In some embodiments, a pluripotent stem cell comprises at least two transcription factors selected from OLIG2, SOX9, NKX6.1, NKX6.2 and OCT4. In some embodiments, a pluripotent stem cell comprises at least three transcription factors selected from OLIG2, SOX9, NKX6.1, NKX6.2 and OCT4. In some embodiments, a pluripotent stem cell comprises at least four transcription factors selected from OLIG2, SOX9, NKX6.1, NKX6.2 and OCT4. In some embodiments, a pluripotent stem cell comprises OLIG2, SOX9, NKX6.1, NKX6.2 and OCT4.

Stem cells of the present disclosure are engineered. Engineered cells are cells that comprise at least one engineered (e.g., recombinant or synthetic) nucleic acid, or are otherwise modified such that they are structurally and/or functionally distinct from their naturally-occurring counterparts. Thus, a cell that contains an exogenous nucleic acid sequence is considered an engineered cell.

In some embodiments, an engineered cell of the present disclosure is an engineered pluripotent stem cell (e.g., an induced pluripotent stem cell), an oligodendrocyte progenitor cell (OPC), or an oligodendrocyte. As used herein unless indicated otherwise, a cell that is engineered to express a (at least one) transcription factor may be engineered to constitutively express the transcription factor or engineered to inducibly express the transcription factor.

OLIG Transcription Factors

In some embodiments, pluripotent stem cells engineered to produce OPCs comprise an OLIG transcription factor. OLIG transcription factors belong to the basic helix-loop-helix family of transcription factors. Examples of OLIG transcription factors include but are not limited to OLIG1, OLIG2, OLIG3 and OLIG4. In some embodiments, the OLIG transcription factor used in TF-mediate reprogramming of the present disclosure is OLIG1. In some embodiments, the OLIG transcription factor is OLIG2. In some embodiments, the OLIG transcription factor is OLIG3. In some embodiments, the OLIG transcription factor is OLIG4. An OLIG transcription factor, or homolog or variant thereof, as used herein, may be a human or other mammalian OLIG transcription factor. Other OLIG2 transcription factors (e.g., from other species) and other OLIG transcription factors, generally, are known and nucleic acids encoding OLIG transcription factors can be found in publically available gene databases, such as GenBank. In some embodiments, the nucleic acid encoding wild-type human OLIG2 is at least 80% (e.g., at least 85%, 90%, 95%, 98% or 100%) identical to the open reading frame of the nucleic acid described in the NCBI Reference Sequence database (RefSeq) under accession number NM_005806. In some embodiments, a nucleic acid encoding OLIG2 is at least 80% (e.g., at least 85%, 90%, 95%, 98% or 100%) identical to SEQ ID NO: 4. In some embodiments, an amino acid sequence encoding OLIG2 is at least 80% (e.g., at least 85%, 90%, 95%, 98% or 100%) identical to SEQ ID NO: 9.

SOX Transcription Factors

In some embodiments, pluripotent stem cells engineered to produce OPCs comprise an SOX transcription factor. Members of the SOX (SRY-related HMG-box) family of transcription factors are characterized by a high mobility group (HMG)-box DNA sequence. This HMG box is a DNA binding domain that is highly conserved throughout eukaryotic species. The Sox family has no singular function, and many members possess the ability to regulate several different aspects of development. Examples of SOX transcription factors include but are not limited to SRY, SOX1, SOX2, SOX3, SOX4, SOX5, SOX6, SOX7, SOX8 SOX9, SOX10, SOX11, SOX12, SOX13, SOX14, SOX15, SOX17, SOX18, SOX21 and SOX30. In some embodiments, the SOX transcription factor used in TF-mediate reprogramming of the present disclosure is SRY. In some embodiments, the SOX transcription factor is SOX1. In some embodiments, the SOX transcription factor is SOX2. In some embodiments, the SOX transcription factor is SOX3. In some embodiments, the SOX transcription factor is SOX4. In some embodiments, the SOX transcription factor is SOX5. In some embodiments, the SOX transcription factor is SOX6. In some embodiments, the SOX transcription factor is SOX7. In some embodiments, the SOX transcription factor is SOX8. In some embodiments, the SOX transcription factor is SOX9. In some embodiments, the SOX transcription factor is SOX10. In some embodiments, the SOX transcription factor is SOX11. In some embodiments, the SOX transcription factor is SOX12. In some embodiments, the SOX transcription factor is SOX13. In some embodiments, the SOX transcription factor is SOX14. In some embodiments, the SOX transcription factor is SOX15. In some embodiments, the SOX transcription factor is SOX17. In some embodiments, the SOX transcription factor is SOX18. In some embodiments, the SOX transcription factor is SOX21. In some embodiments, the SOX transcription factor is SOX30. A SOX transcription factor, or homolog or variant thereof, as used herein, may be a human or other mammalian SOX transcription factor. Other SOX transcription factors (e.g., from other species) and other SOX transcription factors, generally, are known and nucleic acids encoding SOX transcription factors can be found in publically available gene databases, such as GenBank. In some embodiments, the nucleic acid encoding wild-type human SOX9 is at least 80% (e.g., at least 85%, 90%, 95%, 98% or 100%) identical to the open reading frame of the nucleic acid described in the NCBI RefSeq under accession number Z46629.

In some embodiments, a nucleic acid encoding SOX9 is at least 80% (e.g., at least 85%, 90%, 95%, 98% or 100%) identical to SEQ ID NO: 2. In some embodiments, an amino acid sequence encoding SOX9 is at least 80% (e.g., at least 85%, 90%, 95%, 98% or 100%) identical to SEQ ID NO: 7.

NKX Homeobox Transcription Factors

In some embodiments, pluripotent stem cells engineered to produce OPCs comprise a NKX homeobox transcription factor. Members of the NKX family of transcription factors are characterized by a homeobox domain and often regulate development. NKX homeobox transcription factors include members of the NKX2 (NK2) subfamily (e.g., NKX2.1 and NKX2.2) and members of the NKX (NK6) subfamily (e.g., NKX6.1, NKX6.2 and NKX6.3). In some embodiments, the two NKX homeobox transcription factors used in TF-mediate reprogramming of the present disclosure include NKX2.1 and NKX2.2. In some embodiments, the NKX homeobox transcription factor is NKX2.1. In some embodiments, the NKX homobox transcription factor is NKX2.2. In some embodiments, the two NKX homeobox transcription factors are selected from NKX6.1, NKX6.2 and NKX6.3. In some embodiments, the two NKX homeobox transcription factor are NKX6.1 and NKX6.2. In some embodiments, the two NKX homeobox transcription factor are NKX6.2 and NKX6.3. In some embodiments, the two NKX homeobox transcription factor are NKX6.1 and NKX6.3. In some embodiments, the NKX homeobox transcription factor is NKX6.1. In some embodiments, the NKX homeobox transcription factor is NKX6.2. In some embodiments, the NKX homeobox transcription factor is NKX6.3. A NKX homeobox transcription factor, or homolog or variant thereof, as used herein, may be a human or other mammalian SOX transcription factor. Other NKX homeobox transcription factors (e.g., from other species) and other NKX homeobox transcription factors, generally, are known and nucleic acids encoding NKX homeobox transcription factors can be found in publically available gene databases, such as GenBank. In some embodiments, the nucleic acid encoding wild-type human NKX6.1 is at least 80% (e.g., at least 85%, 90%, 95%, 98% or 100%) identical to the nucleic acid described in the NCBI RefSeq under accession number NM_006168. In some embodiments, the nucleic acid encoding wild-type human NKX6.2 is at least 80% (e.g., at least 85%, 90%, 95%, 98% or 100%) identical to the nucleic acid described in the NCBI RefSeq under accession number NM_177400. In some embodiments, the nucleic acid encoding wild-type human NKX6.2 is at least 80% (e.g., at least 85%, 90%, 95%, 98% or 100%) identical to the open reading frame of the nucleic acid described in the NCBI RefSeq under accession number NM_152568.

In some embodiments, a nucleic acid encoding NKX6.1 is at least 80% (e.g., at least 85%, 90%, 95%, 98% or 100%) identical to SEQ ID NO: 1. In some embodiments, an amino acid sequence encoding NKX6.1 is at least 80% (e.g., at least 85%, 90%, 95%, 98% or 100%) identical to SEQ ID NO: 6.

In some embodiments, a nucleic acid encoding NKX6.2 is at least 80% (e.g., at least 85%, 90%, 95%, 98% or 100%) identical to SEQ ID NO: 3. In some embodiments, an amino acid sequence encoding NKX6.2 is at least 80% (e.g., at least 85%, 90%, 95%, 98% or 100%) identical to SEQ ID NO: 8.

OCT Transcription Factors

In some embodiments, pluripotent stem cells engineered to produce OPCs comprise an OCT transcription factor. OCT transcription factors are characterized by a bipartite DNA binding domain called a POU domain. Examples of OCT transcription factors include but are not limited to OCT1, OCT2, OCT 4 and OCT6. In some embodiments, the OCT transcription factor used in TF-mediate reprogramming of the present disclosure is OCT1. In some embodiments, the OCT transcription factor is OCT2. In some embodiments, the OCT transcription factor is OCT4 (also called OCT3/4). In some embodiments, the OCT transcription factor is OCT6. An OCT transcription factor, or homolog or variant thereof, as used herein, may be a human or other mammalian OCT transcription factor. Other OCT transcription factors (e.g., from other species) and other OCT transcription factors, generally, are known and nucleic acids encoding OCT transcription factors can be found in publically available gene databases, such as GenBank. In some embodiments, the nucleic acid encoding wild-type human OCT4 is at least 80% (e.g., at least 85%, 90%, 95%, 98% or 100%) identical to the open reading from of the nucleic acid described in the NCBI RefSeq under accession number NM_002701. NM_203289, NM_001173531, NM_001285986 or NM_001285987. Non-limiting examples of OCT4 variants encompassed herein include POU5F1, transcript variant 1, POU5F1, transcript variant 2. POU5F1, transcript variant 3. POU5F1, transcript variant 4 and POU5F1 transcript variant 5.

In some embodiments, a nucleic acid encoding OCT4 is at least 80% (e.g., at least 85%, 90%, 95%, 98% or 100%) identical to SEQ ID NO: 5. In some embodiments, an amino acid sequence encoding OCT4 is at least 80% (e.g., at least 85%, 90%, 95%, 98% or 100%) identical to SEQ ID NO: 10.

The transcription factors described herein (e.g., an OLIG. SOX. NKX and/or OCT transcription factor) may contain one or more amino acid substitutions relative to its wild-type counterpart. Variants can be prepared according to methods for altering polypeptide sequence known to one of ordinary skill in the art such as are found in references which compile such methods. e.g. Molecular Cloning: A Laboratory Manual, J. Sambrook, et al., eds., Second Edition, Cold Spring Harbor Laboratory Press. Cold Spring Harbor, New York, 1989, or Current Protocols in Molecular Biology, F. M. Ausubel, et al., eds., John Wiley & Sons. Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Methods for Producing OPCs

Provided herein are methods for producing OPCs. In some embodiments, the methods comprise introducing into pluripotent stem cells at least one engineered nucleic acid encoding an oligodendrocyte (OLIG) transcription factor, a SRY-box (SOX) transcription factor, two NKX homeobox transcription factors, and an octamer-binding (OCT) transcription factor, and culturing the pluripotent stem cells to produce O4 positive OPCs (see e.g., Examples 1 and 2).

The OPCs of the present disclosure may further comprise an anti-inflammatory cytokine. See, e.g., Opal et al., Chest. 2000 (4):1162-72 and Benveniste et al., Sci STKE, 2007 (416):pe70 for a discussion of anti-inflammatory cytokines. OPCs in the body do not naturally express anti-inflammatory cytokines (Cannella B, Raine C S. Ann. Neurol. 2004 January; 55(0):46-57). For example, the OPCs of the present disclosure may comprise a nucleic acid encoding an anti-inflammatory cytokine. In some embodiments, an anti-inflammatory cytokine reduces the ability of an OPC to activate the immune system (e.g., suppresses T-cell activation). In some embodiments, the level of proinflammatory cytokines (e.g., cytokines that activate the immune system, including IL17 and IFNγ) secreted by a T-cell in the presence and absence of an OPC may be used to determine the ability of an OPC to activate the immune system. In other embodiments, in vitro cell proliferation assays may be used to assess the effect of a cytokine (e.g., IL10 and IFNβ) that is expressed by an engineered OPC on T cell proliferation. Assays known in the art, including an enzyme-linked immunosorbent assay (ELISA) assay, may be used to determine cytokine levels (See Example 3 in the Examples section below). In some embodiments, an OPC harboring an anti-inflammatory cytokine reduces T-cell activation (e.g., as measured by a lower level of secreted proinflammatory cytokines) by at least 2-fold, 3-fold, 5-fold, 10-fold, 20-fold, 50-fold or 100-fold compared to an OPC not harboring the anti-inflammatory cytokine under the same or substantially conditions.

Suitable anti-inflammatory cytokines for the present disclosure include, but are not limited to, interferons and interleukins. For example, cells may be engineered to express interferon beta (IFNβ) and/or interleukin 10 (IL10). In some embodiments, an engineered OPC expresses/comprises IFNβ (e.g., also referred to herein as IFNβ1). In some embodiments, an engineered OPC expresses/comprises IL10. In some embodiments, an engineered OPC expresses/comprises both IFNβ and IL10. The sequences of the interferons and cytokines may be obtained from publically available databases, including National Center for Biotechnology Information's GenBank. An exemplary interferon beta 1 (IFNβ) sequence is listed under the GenBank Accession Identifier NM_002176. An exemplary IL10 sequence is listed under the GenBank Accession Identifier NM_000572. It should be understood that, in some embodiments, only the open reading frame is used to express the transcription factors and cytokines described herein.

The anti-inflammatory cytokines may be secreted or promote the secretion of another anti-inflammatory cytokine. For example, an anti-inflammatory cytokine may promote the secretion of IL10. In some embodiments, an OPC harboring an anti-inflammatory cytokine secretes at least 2-fold, at least 3-fold, at least 5-fold, at least 10-fold, at least 20-fold, at least 50-fold, at least 100-fold, at least 200-fold, at least 300-fold, at least 400-fold, at least 500-fold, at least 600-fold, at least 700-fold, at least 800-fold, at least 900-fold, at least 1,000-fold, at least 1,500-fold, at least 2,000-fold, at least 3,000-fold, at least 4,000-fold, at least 5.000-fold, at least 6,000-fold, at least 7,000-fold, at least 8,000-fold, at least 9,000-fold, or at least 10,000-fold more IL10 than a control counterpart not harboring the anti-inflammatory cytokine.

In some embodiments, an OPC harboring an anti-inflammatory cytokine secretes at least 2-fold, at least 3-fold, at least 5-fold, at least 10-fold, at least 20-fold, at least 50-fold, at least 100-fold, at least 200-fold, at least 300-fold, at least 400-fold, at least 500-fold, at least 600-fold, at least 700-fold, at least 800-fold, at least 900-fold, at least 1,000-fold, at least 1,500-fold, at least 2,000-fold, at least 3,000-fold, at least 4,000-fold, at least 5.000-fold, at least 6,000-fold, at least 7,000-fold, at least 8,000-fold, at least 9,000-fold, or at least 10,000-fold more IFNβ than a control counterpart not harboring the anti-inflammatory cytokine.

In some embodiments, iPSCs are engineered to express IL-10 and SOX9, NKX6.1, OLIG2, NKX6.2, and/or OCT4. In some embodiments, the engineered iPSCs differentiate into OPCs (e.g., O4+ cells) within 1-10 days of induction of expression of IL-10 and SOX9, NKX6.1, OLIG2, NKX6.2, and/or OCT4. In some embodiments, the engineered cells (e.g., iPSCs or OPCs) secrete IL-10. In some embodiments, the engineered cells (e.g., engineered iPSCs or engineered OPCs) secrete IL-10 at a level that is at least 50-fold, at least 60-fold, at least 70-fold, at least 80-fold, at least 90-fold, at least 100-fold, at least 200-fold, at least 300-fold, at least 400-fold, at least 500-fold, at least 600-fold, at least 700-fold, at least 800-fold, at least 900-fold, at least 1,000-fold, at least 1.500-fold, at least 2,000-fold, at least 3,000-fold, at least 4.000-fold, at least 5,000-fold, at least 6,000-fold, at least 7,000-fold, at least 8,000-fold, at least 9,000-fold, or at least 10.000-fold higher than control cells. Control cells may be naturally-occurring iPSCs or OPCs, engineered iPSCs or engineered OPCs that are not specifically modified to express IL-10, or iPSCs or OPCs that are engineered to inducibly express IL-10 but are cultured under conditions that lack an inducing agent (i.e., IL-10 expression is not induced). In some embodiments, the control cell is the same type of cell (e.g., iPSC or OPC) as the engineered cell. In some embodiments, the iPSCs or OPCs secrete IL-10 at a level that is at least 50-fold, at least 60-fold, at least 70-fold, at least 80-fold, at least 90-fold, or at least 100-fold higher than control cells within 1-10 days of induction of expression of IL-10 and SOX9, NKX6.1, OLIG2, NKX6.2, and/or OCT4.

In some embodiments, an engineered cell secretes IL-10 (e.g., steadily/continuously) over the course of 1, 2, 3, 4, 5, 6, 7, 8, 9, 10, 11, 12, 13, 14, 15, 16, 17, 18, 19, or 20 days of culturing (e.g., in the presence of an inducing agent or in the absence of an inducing agent).

In some embodiments, iPSCs or iPSC-derived cells are engineered to express IL10 and/or IFNβ.

In some embodiments, iPSCs are engineered to express IFNβ and SOX9, NKX6.1, OLIG2, NKX6.2, and/or OCT4. In some embodiments, the engineered iPSCs differentiate into OPCs (e.g., O4+ cells) within 1-10 days of induction of expression of IFNβ and SOX9, NKX6.1, OLIG2, NKX6.2, and/or OCT4. In some embodiments, the engineered cells (e.g., engineered iPSCs or engineered OPCs) secrete IL-10. In some embodiments, the engineered cells (e.g., engineered iPSCs or engineered OPCs) secrete TIL-10 at a level that is at least 50-fold, at least 60-fold, at least 70-fold, at least 80-fold, at least 90-fold, or at least 100-fold, at least 200-fold, at least 300-fold, at least 400-fold, at least 500-fold, at least 600-fold, at least 700-fold, at least 800-fold, at least 900-fold, at least 1,000-fold, at least 1.500-fold, at least 2,000-fold, at least 3,000-fold, at least 4,000-fold, at least 5,000-fold, at least 6,000-fold, at least 7,000-fold, at least 8,000-fold, at least 9,000-fold, or at least 10,000-fold higher than control cells. Control cells include naturally-occurring iPSCs or OPCs, engineered iPSCs or engineered OPCs that are not specifically modified to express IFNβ, or iPSCs or OPCs that are engineered to inducibly express IFNβ, but are cultured under conditions that lack an inducing agent. In some embodiments, the engineered iPSCs or engineered OPCs secrete IL-10 at a level that is at least 50-fold, at least 60-fold, at least 70-fold, at least 80-fold, at least 90-fold, or at least 100-fold higher than control cells within 1-10 days of induction of expression of IFNβ and SOX9, NKX6.1, OLIG2, NKX6.2, and/or OCT4.

In some embodiments, iPSCs are engineered to express IFNβ, IL-10, and SOX9, NKX6.1, OLIG2, NKX6.2, and/or OCT4. In some embodiments, the engineered iPSCs differentiate into OPCs (e.g., O4+ cells) within 1-10 days of induction of expression of IFNβ, IL-10, and SOX9, NKX6.1, OLIG2, NKX6.2, and/or OCT4. In some embodiments, the engineered iPSCs or engineered OPCs secrete IL-10. In some embodiments, the engineered cells (e.g., engineered OPCs or engineered iPSCs) secrete IL-10 at a level that is at least 50-fold, at least 60-fold, at least 70-fold, at least 80-fold, at least 90-fold, or at least 100-fold, at least 200-fold, at least 300-fold, at least 400-fold, at least 500-fold, at least 600-fold, at least 700-fold, at least 800-fold, at least 900-fold, at least 1,000-fold, at least 1,500-fold, at least 2,000-fold, at least 3,000-fold, at least 4,000-fold, at least 5,000-fold, at least 6.000-fold, at least 7,000-fold, at least 8.000-fold, at least 9,000-fold, or at least 10,000-fold higher than control cells. Control cells include naturally-occurring iPSCs or OPCs, engineered iPSCs or engineered OPCs that are not specifically modified to express IFNβ and IL-10, and iPSCs or OPCs that are engineered to inducibly express IFNβ and IL-10, but are cultured under conditions that lack an inducing agent. In some embodiments, the engineered iPSCs or engineered OPCs secrete IL-10 at a level that is at least 50-fold, at least 60-fold, at least 70-fold, at least 80-fold, at least 90-fold, or at least 100-fold higher than control cells within 1-10 days of induction of expression of IFNβ, IL-10, and SOX9, NKX6.1, OLIG2, NKX6.2, and/or OCT4.

A nucleic acid, generally, is at least two nucleotides covalently linked together, and in some instances, may contain phosphodiester bonds (e.g., a phosphodiester "backbone"). A nucleic acid is considered "engineered" if it does not occur in nature. Examples of engineered nucleic acids include recombinant nucleic acids and synthetic nucleic acids. In some embodiments, an engineered nucleic acid encodes an OLIG (e.g., OLIG2) transcription factor. In some embodiments, an engineered nucleic acid encodes an SOX (e.g., SOX9) transcription factor. In some embodiments, an engineered nucleic acid encodes an NKX homeobox (e.g., NKX6.1 and/or NKX 6.2) transcription factor. In some embodiments, an engineered nucleic acid encodes an OCT (e.g., OCT4) transcription factor. In some embodiments, a single transcription factor is encoded by a single nucleic acid, while in other embodiments, a single nucleic acid may encode two or more transcription factors (e.g., each operably linked to a different promoter, or both operably linked to the same promoter).

Nucleic acids encoding the transcription factors described herein may be introduced into a pluripotent stem cell using any known methods, including but not limited to chemical transfection, viral transduction (e.g. using lentiviral vectors, adenovirus vectors, sendaivirus, and adeno-associated viral vectors) and electroporation. For example, methods that do not require genomic integration include transfection of mRNA encoding one or more of the transcription factors and introduction of episomal plasmids. In some embodiments, the nucleic acids (e.g., mRNA) are delivered to pluripotent stem cells using an episomal vector (e.g., episomal plasmid). In other embodiments, nucleic acids encoding transcriptions factors for reprogramming pluripotent stem cells may be integrated into the genome of the cell. Genomic integration methods are known, any of which may be used herein, including the use of the PIGGYBAC™ transposon system, sleeping beauty system, lentiviral system, adeno-associated virus system, and the CRISPR gene editing system.

In some embodiments, an engineered nucleic acid is present on PIGGYBAC™ transposon vector that comprises PIGGYBAC™ inverted terminal repeat sequences flanking a nucleotide sequence encoding a transcription factor and/or anti-inflammatory cytokine of the present disclosure. PIGGYBAC™ transposases are enzymes that recognize PIGGYBAC™ inverted terminal repeats on each side of an insertion sequence (e.g., sequence encoding a transcription factor of interest), excise the insertion sequence and insert the excised element into another nucleic acid. PIGGYBAC™ transposases may insert excised sequences into target sites with the sequence TTAA. An exemplary sequence encoding PIGGYBAC™ transposase is described in GenBank accession number: EF587698.

In some embodiments, a transcription factor is cloned into a PIGGYBAC™ transposon vector then nucleofected at high copy numbers (e.g., an average of 10 copies per cell) into iPSCs and integrated into the genome by codelivering a PIGGYBAC™ transposase. In some embodiments, a high copy number is 5 to 50 copies, inclusive, (e.g., average of 5 to 50 copies inclusive or exactly 5 to 50 copies inclusive) of a nucleotide sequence encoding a transcription factor (e.g., SOX9, NKX6.1, OLIG2, NKX6.2, and/or OCT4) per cell. In some embodiments, a cell has at least 5, 10, 15, 20, 25, or 50 copies of a nucleotide sequence encoding a transcription factor. In some embodiments, a cell has 15 copies of a nucleotide sequence encoding a transcription factor. In some embodiments, a cell has 5 to 10 copies, 5 to 20 copies, 5 to 30 copies, 5 to 40 copies, 10 to 20 copies, 10 to 30 copies, 10 to 40 copies, 10 to 50 copies, 15 to 20 copies, 15 to 25 copies, 15 to 30 copies, 15 to 35 copies, 15 to 40 copies, 15 to 45 copies, 15 to 50 copies, 20 to 30 copies, 20 to 40 copies, 20 to 50 copies, 30 to 40 copies, 30 to 50 copies, or 40 to 50 copies of a nucleotide sequence encoding a transcription factor. In some instances, the copy number refers to the average copy number of at least one nucleotide sequence encoding at least one transcription factor per cell in a population of cells (e.g., in a polyclonal population of cells). In some instances, the copy number refers to the exact copy number of at least one nucleotide sequence encoding at least transcription factor in a cell or of every cell in a population of cells (e.g., in a clonal population of cells).

In some embodiments, a high copy number may be obtained by introducing a high concentration of DNA into a population of cells. In some embodiments, a high concentration of DNA is a DNA concentration that is greater than or equal to 1,000 ng DNA per 1 million cells, greater than 2,000 ng DNA per 1 million cells, greater than 5,000 ng DNA per 1 million cells, or greater than 10,000 ng DNA per 1 million cells.

In some embodiments, a low copy number is obtained by introducing a low concentration of DNA into a population of cells. In some embodiments, a low concentration of DNA is a DNA concentration that is less than 1,000 ng DNA per 1 million cells, less than 500 ng DNA per 1 million cells, less than 400 ng DNA, less than 300 ng DNA per 1 million cells.

The plasmid may be designed to be, for example, antibiotic resistant and/or inducible (e.g., doxycycline-inducible) in order to permit the selection of transcription factor-integrated cells and/or to control transcription.

In some embodiments, a PIGGYBAC™ transposon vector comprises PIGGYBAC™ inverted terminal repeat sequences flanking a nucleotide sequence encoding an OLIG (e.g., OLIG2) transcription factor. In some embodiments, a PIGGYBAC™ transposon vector comprises PIGGYBAC™ inverted terminal repeat sequences flanking a nucleotide sequence encoding a SOX (e.g., SOX9) transcription factor. In some embodiments, a PIGGYBAC™ transposon vector comprises PIGGYBAC™ inverted terminal repeat sequences flanking a nucleotide sequence encoding a NKX homeobox (e.g., NKX6.1 and/or NKX 6.2) transcription factor. In some embodiments, a PIGGYBAC™ transposon vector comprises PIGGYBAC™ inverted terminal repeat sequences flanking a nucleotide sequence encoding OCT (e.g., OCT4) transcription factor. In some embodiments, the nucleotide sequence encoding any three or more of OLIG2, SOX9, NKX6.1, NKX6.2 and OCT4 are placed, in the same cassette flanked by PIGGYBAC™ inverted terminal repeat sequences. The transcription factors in this cassette may be separated or not separated such that they produce unconnected proteins, for instance by separating the transcription factors by internal ribosome entry sites (IRES) or polypeptide cleavage signals such as 2A sequences. In some embodiments, the nucleotide sequence encoding IFNβ and/or IL10 are flanked by PIGGYBAC™ inverted terminal repeat sequences.

In some embodiments, an engineered nucleic acid is present on an expression plasmid, which is introduced into pluripotent stem cells. In some embodiments, the expression plasmid comprises a selection marker, such as an antibiotic resistance gene (e.g., bsd, neo, hygB, pac, ble, or Sh bla) or a gene encoding a fluorescent protein (RFP, BFP, YFP, or GFP). In some embodiments, an antibiotic resistance gene encodes a puromycin resistance gene. In some embodiments, the selection marker enables selection of cells expressing a transcription factor of interest (e.g., OLIG, SOX, NKX, and/or OCT).

Any of the engineered nucleic acids described herein may be generated using conventional methods. For example, recombinant or synthetic technology may be used to generate nucleic acids encoding the transcription factors described herein. Conventional cloning techniques may be used to insert a transcription factor of interest into a PIGGYBAC™ transposon vector.

In some embodiments, an engineered nucleic acid (optionally present on an expression plasmid) comprises a nucleotide sequence encoding a transcription factor operably linked to a promoter (promoter sequence). In some embodiments, the promoter is an inducible promoter (e.g., comprising a tetracycline-regulated sequence). Inducible promoters enable, for example, temporal and/or spatial control of transcription factor expression.

A promoter control region of a nucleic acid sequence at which initiation and rate of transcription of the remainder of a nucleic acid sequence are controlled. A promoter may also contain sub-regions at which regulatory proteins and molecules may bind, such as RNA polymerase and other transcription factors. Promoters may be constitutive, inducible, activatable, repressible, tissue-specific or any combination thereof. A promoter drives expression or drives transcription of the nucleic acid sequence that it regulates. Herein, a promoter is considered to be "operably linked" when it is in a correct functional location and orientation in relation to a nucleic acid sequence it regulates to control ("drive") transcriptional initiation and/or expression of that sequence.

An inducible promoter is one that is characterized by initiating or enhancing transcriptional activity when in the presence of, influenced by or contacted by an inducing agent. An inducing agent may be endogenous or a normally exogenous condition, compound or protein that contacts an engineered nucleic acid in such a way as to be active in inducing transcriptional activity from the inducible promoter.

Inducible promoters for use in accordance with the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid 25 receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

A preparation of pluripotent stem cells (e.g., expressing the transcription factor combination as provided herein) may be cultured under standard stem cell culture conditions. For example, the pluripotent stem cells may be cultured in any commercially-available feeder-free maintenance medium for human ESCs and iPSCs, such as mTeSR™1 media. In some embodiments, the pluripotent stem cells are cultured in commercially-available stem cell media without added nutrients or growth factors.

A preparation of pluripotent stem cells (e.g., expressing the transcription factor combination as provided herein) may be cultured, in some embodiments, for as few as 4 to 10 day before producing O4-positive OPCs. In some embodiments, the pluripotent stem cells are cultured for 4-10 days, 4-9 days, 4-8 days, 4-7 days, 4-6 days or 4-5 days. In some embodiments, the pluripotent stem cells are cultured for less than 4 days (e.g., 1, 2 and 3 days) before producing O4-positive OPCs. In some embodiments, at least 10% (at least 20%, 30%, 40%, 50%, 60%, 70% or 80%) of the cells of the preparation express O4 after only 4-10 days (e.g., 4, 5, 6, 7, 8, 9 or 10) of culture.

A preparation of pluripotent stem cells (e.g., expressing the transcription factor combination as provided herein) may include, for example, $10^4$ to $10^{10}$ cells. In some embodiments, a preparation of pluripotent stem cells includes $10^4$, $10^5$, $10^6$, $10^7$, $10^8$, $10^9$, or $10^{10}$ cells.

Expression of O4 and other OPC-specific markers may be assessed based on protein expression or nucleic acid expression using known methods. Additional OPC-specific markers include, but are not limited to, Sox1, Pax6, Nestin, Islet1, A2B5, Sox10, Olig2, Olig1, PDGFRa, NG2, RIP, O1, PLP1, CNPase, GalC, MBP, MAG and MOG. In some embodiments, an OPC does not express OCT4, Nanog, and/or SOX2. Exemplary methods include immunofluorescence using an anti-O4 antibody conjugated to a fluorophore, using western blot analysis with an anti-O4 antibody, quantitative polymerase chain reaction with primers targeting O4, and fluorescence activated cell sorting (FACS) with an anti-O4 antibody. In some embodiments, the methods further comprise sorting for O4-positive OPCs (e.g., using FACS).

In some embodiments, the methods further comprise culturing OPCs to produce oligodendrocytes. Culturing of OPCs may include the use of media comprising factors that induce oligodendrocyte differentiation, including growth hormones (e.g., fibroblast growth factors). Oligodendrocytes may be characterized by cell surface markers (e.g., MOG and GalC). Oligodendrocytes may also, or may alternatively, be characterized by their ability to form myelin. As exemplified below, cells engineered by the methods disclosed herein may be co-cultured with iPSC-derived neurons (e.g., in a polyethylene glycol mold) for a period of time (e.g., a few weeks) and assessed for myelination (e.g., the co-cultures can be fixed, embedded in resin, sectioned, stained and imaged using transmission electron microscopy to assess myelination). In some embodiments, the engineered cells of the present disclosure increase the number of myelinated axons by at least two-fold, at least 3-fold, at least 4-fold, at least 5-fold, at least 6-fold, at least 7-fold, at least 8-fold, at least 9-fold, or at least 10-fold. In some embodiments, the extent of myelination may be calculated by determining the g-ratio. The axonal g-ratio is the ratio between the inner and the outer diameter of the myelin sheath. In some embodiments, the axonal g-ratio from a subject who has been administered any of the engineered cells of the present disclosure is similar to the g-ratio of myelin from a control (e.g., the subject prior to administration of the engineered cells or a healthy subject). In some embodiments, the axonal g-ratio from a subject who has been administered any of the engineered cells of the present disclosure is similar to the axonal g-ratio from a control (e.g., the subject prior to administration of the engineered cells or a healthy subject) if the axonal g-ratio of myelin from the subject is on average between 0.6-0.8. See. e.g., Mohammadi et al., Front Neurosci. 2015 Nov. 27:9:441.

In some embodiments, the OPCs described herein have been engineered to express IL-10 and/or IFNβ. In some embodiments, the OPCs are cultured to express IL-10 and/or IFNβ (e.g., with an inducing agent if cytokine expression is controlled by an inducible promoter). Without being bound by a particular theory. OPCs engineered to express IL-10 and/or IFNβ may be useful in the treatment of a subject with a myelin degenerative disease (e.g., Multiple Sclerosis). Without being bound by a particular theory, immune-tolerant cells such as engineered OPCs with capability to secrete IL10 and IFNβ secretion not only can regenerate and remyelinate the axons can protect itself and adjacent cells from the immune attack. In some embodiments. OPCs engineered to secrete IL10 and IFNβ may reduce or suppress the immune response of a host to administered OPCs and promote regeneration.

In some embodiments, the engineered OPCs are cultured with other cells (e.g., neurons) to produce a myelinated organoid. In some embodiments, the myelinated organoid is transplanted into a subject in need thereof (e.g., a subject with a demyclinating disorder). In some embodiments, the organoid is a cerebral organoid (e.g., partial or complete cerebral organoid). In some embodiments, the engineered myelinated organoid is used to compound screening (e.g., therapeutic drugs) or disease modeling.

In some embodiments, a pluripotent stem cell (e.g. iPSC) and/or OPC comprises at least three transcription factors selected from (a) oligodendrocyte 2 (OLIG2), (b) SRY-box 9 (SOX9), (c) NKX homeobox 6.1 (NKX6.1), (d) NKX homeobox 6.2 (NKX6.2), and (e) octamer-binding 4 (OCT4). In some embodiments, a pluripotent stem cell (e.g. iPSC) and/or OPC comprises OCT4, SOX9, and NKX6.1. In some embodiments, a pluripotent stem cell (e.g. iPSC) and/or OPC comprises OCT4, OLIG2, and NKX6.1. In some embodiments, a pluripotent stem cell (e.g. iPSC) and/or OPC comprises OCT4, NKX6.2, and NKX6.1. In some embodiments, a pluripotent stem cell (e.g. iPSC) and/or OPC comprises OCT4, SOX9, and OLIG2. In some embodiments, a pluripotent stem cell (e.g. iPSC) and/or OPC comprises OLIG2, SOX9, and NKX6.1.

In some embodiments, a pluripotent stem cell (e.g. iPSC) and/or OPC comprises at least four transcription factors selected from (a) OLIG2, (b) SOX9, (c) NKX6.1, (d) NKX6.2, and (e) OCT4. In some embodiments, a pluripotent stem cell (e.g. iPSC) and/or OPC comprises OCT4, OLIG2, NKX6.1, and NKX6.2. In some embodiments, a pluripotent stem cell (e.g. iPSC) and/or OPC comprises SOX9, OLIG2, NKX6.1, and NKX6.2. In some embodiments, a pluripotent stem cell (e.g. iPSC) and/or OPC comprises OCT4, OLIG2, NKX6.1, and NKX6.2. In some embodiments, a pluripotent stem cell (e.g. iPSC) and/or OPC comprises OCT4, OLIG2, NKX6.1, and SOX9. In some embodiments, a pluripotent stem cell (e.g. iPSC) and/or OPC comprises OCT4, SOX9, NKX6.1, and NKX6.2.

In some embodiments, a pluripotent stem cell (e.g. iPSC) and/or OPC comprises OLIG2, SOX9, NKX6.1, NKX6.2, and OCT4.

Pharmaceutical Compositions and Uses Thereof

Also provided herein are pharmaceutical composition comprising pluripotent stem cells (e.g., induced pluripotent stem cells). OPCs and/or oligodendrocytes produced by any of the methods disclosed herein. The pharmaceutical compositions may further comprise a pharmaceutically-acceptable carrier (e.g., a nanocarrier) or excipient. Hydrogels may also be used as pharmaceutically-acceptable carriers. Non-limiting examples of pharmaceutically-acceptable excipients include water, saline, dextrose, glycerol, ethanol and combinations thereof. The pharmaceutically-acceptable excipient may comprise phosphate buffered saline, a bicarbonate solution, a preservative, a stabilizing agent, an emulsifier (e.g., a phospholipid emulsifier), a solubilizing agent (e.g., surfactant), or a binding agent. The excipient may be selected on the basis of the mode and route of administration, and standard pharmaceutical practice.

General considerations in the formulation and/or manufacture of pharmaceutical agents, such as compositions comprising any of the engineered cells disclosed herein, may be found, for example, in Remington: The Science and Practice of Pharmacy 21st ed., Lippincott Williams & Wilkins, 2005 (incorporated herein by reference in its entirety).

Any of the pharmaceutical compositions disclosed herein may be administered to a subject (e.g., a human subject). Additional exemplary subjects include, but are not limited to, mice, rats, rabbits, horses, dogs, cats, goats, sheep and other animals. The subject may have a demyelinating disorder. Demyelinating disorders include disorders in which myelin surrounding axons is lost or damaged. Magnetic resonance imaging (MRI) may be used to diagnose a demyelinating disorder. Examples of demyelinating disorders include disorders in which myelin in the central nervous system is damaged. In some embodiments, the demyelinating disorder includes damage to OPCs. An exemplary demyelinating disorder is multiple sclerosis.

The term "an effective amount" or a "therapeutically effective amount" as used herein refers to the amount of OPCs and/or oligodendrocytes required to confer therapeutic effect on a subject, either alone or in combination with at least one other active agent. Effective amounts vary, as recognized by those skilled in the art, depending on the route of administration, excipient usage, and co-usage with other active agents. The quantity to be administered depends on the subject to be treated, including, for example, the strength of an individual's immune system or genetic predispositions. Suitable dosage ranges are readily determinable by one skilled in the art and may be on the order of micrograms of the polypeptide of this disclosure. The dosage of the preparations disclosed herein may depend on the route of administration and varies according to the size of the subject.

Suitable routes of administration include, for example, parenteral routes such as intravenous, intrathecal, parenchymal, or intraventricular routes. Suitable routes of administration include, for example, parenteral routes such as intravenous, intrathecal, parenchymal, or intraventricular injection.

EXAMPLES

Example 1: Identification of Transcription Factor Combinations Capable of Differentiating Induced Pluripotent Stem Cells (iPSCs) into Oligodendrocyte Progenitor Cells (OPCs)

To identify transcription factor (TF) combinations capable of inducing the formation of OPCs, sixteen different pools of transcription factors were generated and tested for their ability to form OPCs. Each TF was cloned into a PIGGYBAC™ transposon vector (PBAN) and nucleofected at high copy numbers into iPSCs and integrated into the genome with the co-delivery of PIGGYBAC™ transposase. The PBAN plasmid was designed to be puromycin resistant and doxycycline-inducible to enable selection of TF-integrated cells and to express the TFs on demand, respectively. PIGGYBAC™ transposon vectors were used to increase the copy number of the TFs integrated into the genome and to improve the viability of the iPSCs. After cells were nucleofected with transcription factors, cells were treated with puromycin to select for integrants. TF expression was induced by the addition of doxycycline (500 ng/mL) to stem cell media (mTeSR1) for four days (FIG. 1).

Cells expressing each TF combination were then tested for their ability to form OPCs. iPSCs were nucleofected with the TFs and cultured in stem cell media (mTeSR1) without antibiotics and on a Matrigel-coated plate. The cells were kept on Y27632 ROCK inhibitor for one day. After the cells reached 80% confluency puromycin (1 µg/ml) was added to the media to select for integrants. TF expression was induced by addition of doxycycline (500 ng/mL) to stem cell media (mTeSR1) for four days. The cells then were harvested using TrypLE Express (1%) and were fixed in 4% paraformaldehyde. After blocking with 5% BSA, the cells were stained for anti-O4 antibody and the percentage of them that were expressing the O4 marker was assessed using flow cytometry. This study identifies combinations of TFs sufficient to promote OPC formation, without nutrient, growth factor or microenvironmental optimization.

The study identified OLIG2, SOX9, NKX6.1, NKX6.2 and OCT4 as a combination of transcription factors capable of forming OPCs. While iPSCs nucleofected with OLIG2, NKX6.1, NKX6.2, SOX9, and OCT4 constructs continued to form iPSC colonies in the absence of doxycycline (no transcription factor induction), induction of this combination of transcription factors changed the morphology of the iPSCs (FIG. 2). Doxycycline treatment of iPSCs nucleofected with OLIG2, SOX9, NKX6.1, NKX6.2 and OCT4 constructs resulted in cells breaking away from the iPSC colonies and displaying a branched morphology (FIG. 2). These morphological changes are consistent with iPSCs differentiating into OPCs.

Immunohistochemistry analysis was used to determine whether the combination of OLIG2, SOX9, NKX6.1, and OCT4 induced the development of OPCs. iPSCs nucleofected with this combination of TFs were treated with doxycycline to induce expression of the TFs. Immunohistochemistry analysis was then performed with anti-O4, anti-Myelin oligodendrocyte glycoprotein (MOG), anti-NG2 (an integral membrane chondroitin sulfate proteoglycan) and anti-Galactocerebroside (anti-GalC) antibodies to determine the stage of oligodendrocyte development. NG2 was used as early stage OPC marker, O4 was used as an intermediate proliferative premitotic OPC marker. GalC was used as a marker for late stage OPC (post-mitotic) and early mature oligodendrocytes and MOG was used as a marker for mature oligodendrocytes. At four days after induction of TF expression, cells stained positive for O4 (FIG. 3A). At eight days after induction of TF expression, the cells stained positive for O4 (FIG. 3B) and the myelin marker MOG (FIG. 3C). FIGS. 3A-3C demonstrate that O4-expressing O4+ cells can be generated using a subset (OLIG2, SOX9, NKX6.1 and OCT4) of the five transcription factors identified.

Figure 4A:
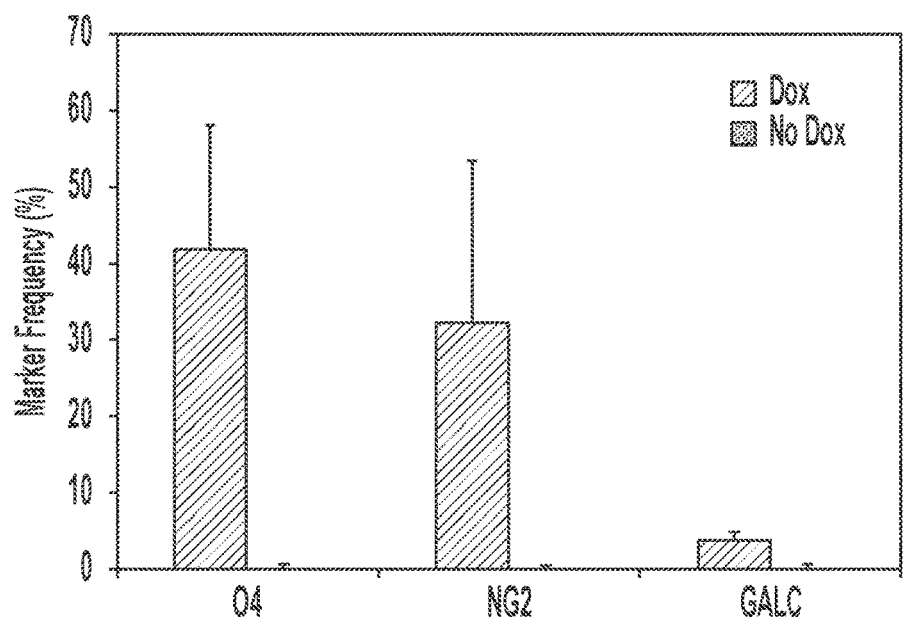
FIGS. 4A-4B includes data indicating that the induced OPCs are capable of forming myelin-producing cells.

Fluorescence activated cell sorting (FACS) was also used for quantitative analysis of conversion percentage of iPSCs to the oligodendrocyte lineage, the cells (engineered by expressing OLIG2, SOX9, NKX6.1, NKX6.2 and OCT4) were stained for anti-NG2, anti-O4, and anti-Galactocerebroside (GalC) surface markers and compared against the nucleofected iPSCs with no exposure to doxycycline (no TF induction). As shown in FIG. 4A, four days after induction of TF (OLIG2, SOX9, NKX6.1, NKX6.2, and OCT4) expression about 40% of doxycycline-treated cells were O4-positive and about 30% of cells were NG2-positive. Few doxycycline-treated cells were positive for the late stage OPC (post-mitotic) and early mature oligodendrocyte marker GalC at 4 days. In contrast, nucleofected iPSCs had negligible expression of all three surface markers in the absence of doxycycline (no induction of TF expression). Thus, the combination of OLIG2, SOX9, NKX6.1, NKX6.2, and OCT4 transcription factors can efficiently induce the development of iPSCs into O4-positive OPCs. As shown in the Examples below, other subsets of this combination can also induce the development of iPSCs into O4-positive OPCs.

Figure 5:
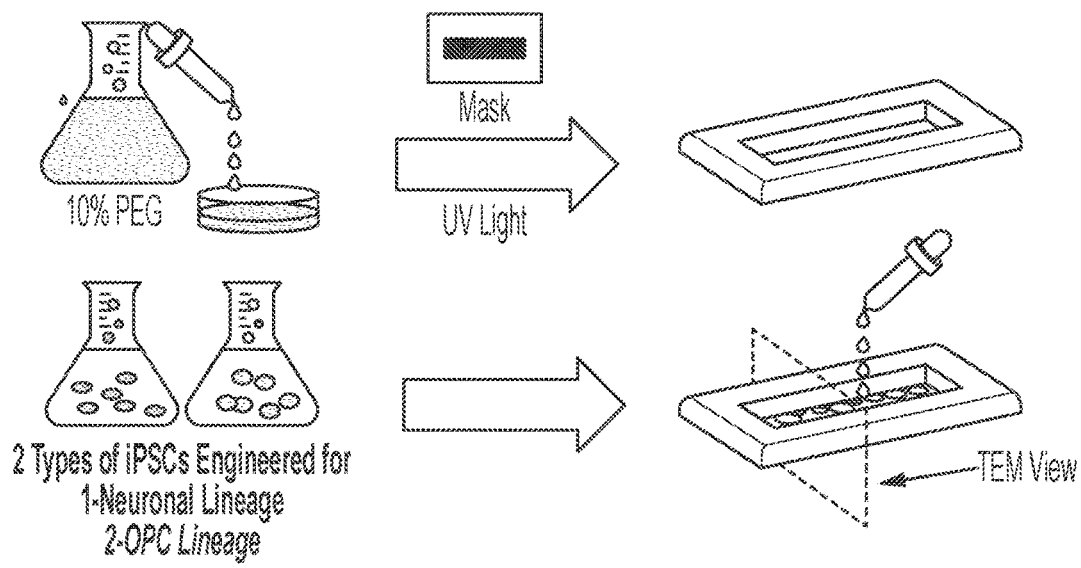
FIG. 5 shows a schematic of the process of making micro-grooves for analysis of the functional ability of OPCs. It shows in vitro myclin formation and photo-micropatterning of microgrooves for co-culture of oligodendrocyte/neuron-generating iPSCs.

To assess the ability of the generated OPCs (engineered by expressing OLIG2, SOX9, NKX6.1, NKX6.2, and OCT4) to form myelin-producing oligodendrocytes, the cells were co-cultured with doxycycline inducible iNGN (Neurogenin-mediated) stem cells in a polyethylene glycol mold. The mold was created using photomicropatterning and was shaped like a narrow channel (micro-groove) in order to contain the cells. This method lets the neurons align along the channel and allowed the OPCs to integrate with the neurons and form myelin. To make a micro-groove, cells were co-cultured with iPSCs that were previously developed and engineered to form neurons (FIG. 5). A 10% polyethylene glycol (PEG) solution was added to the collagen-coated transwell. A negative mask to form a microgroove (narrow channel) was used and the light-sensitive solution was irradiated for 30 seconds with UV light. Neurons do not grow in PEG unless it has been functionalized or biomolecules are added to promote neuronal growth. Therefore in this example, it acts as a cell restrictive mold which contains neuronal extensions into the micro-grooves leading to a highly fasciculated aligned neuronal outgrowth. Meanwhile the limited space will increase the interaction between the OPC and neuron-generating iPSCs leading to integration of the two cell types and formation of myelin sheaths with dense lines and intermediate lines, confirming the occurrence and abundance of mature myelin layers. This demonstrates that the OPCs have the capacity to differentiate into functional myelin-forming cells.

Figure 4B:
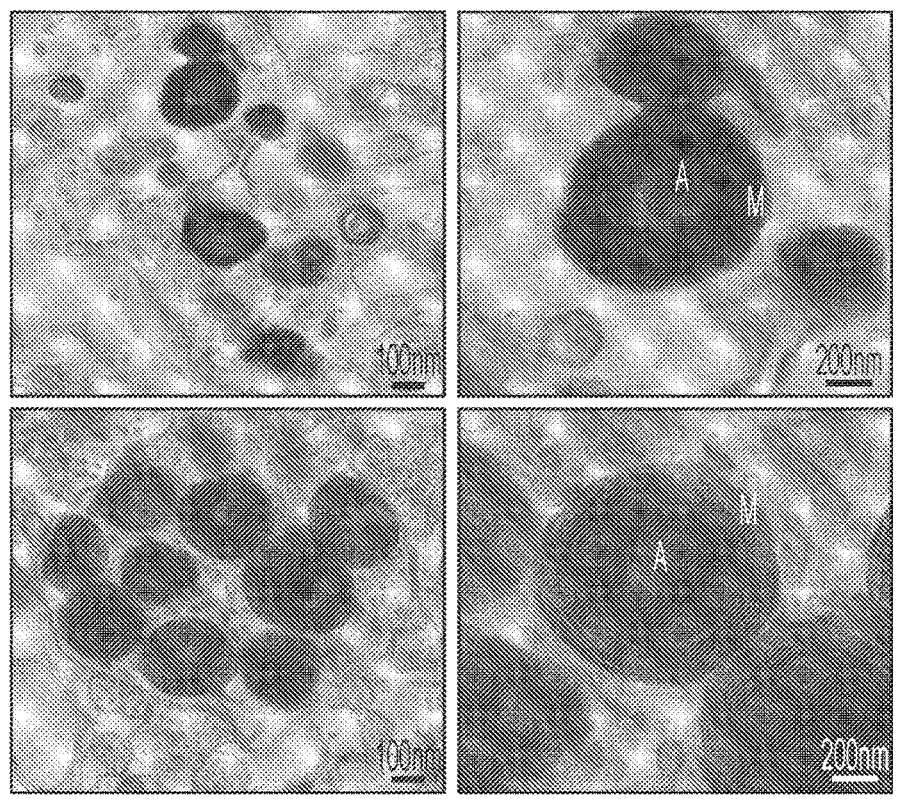

After four weeks of co-culture of generated OPCs with iNGN cells, the constructs were fixed, embedded in resin, sectioned, stained and imaged using transmission electron microscope (TEM) (FIG. 4B). TEM analysis showed robust myelin formation around the developing neurons. Thus, the OPCs generated by expressing OLIG2, SOX9, NKX6.1, NKX6.2, and OCT4 are capable of forming myelin-producing oligodendrocytes.

Example 2: Identification of Transcription Factor Combination Subsets Capable of Inducing Differentiating of Induced Pluripotent Stem Cells (IPSCs) into Oligodendrocyte Progenitor Cells (OPCs)

A combination of five TFs (SOX9, NKX6.2, NKX6.1, OCT4, and OLIG2) along with subsets of this combination (FIG. 6, bottom chart) were characterized using the gateway-compatible doxycycline-inducible puromycin resistant PIGGYBAC™ transposon system described above. Each combination (designated OPC0 through OPC10) included three, four or five of the TFs. For example, OPC0 included the combination of OLIG2, OCT4, SOX9, NKX6.1, and NKX6.2. OPC1 included the combination of OCT4, SOX9, and NKX6.1. OPC2 included the combination of OCT4, OLIG2, and NKX6.1. OPC3 included the combination of OCT4, NKX6.1 and NKX6.2. OPC4 included the combination of OCT4, SOX9, and OLIG2. OPC5 included the combination of OLIG2, SOX9, and NKX6.1. OPC6 included the combination of OCT4, OLIG2, NKX6.1, and NKX6.2. OPC7 included the combination of OLIG2, SOX9, NKX6.1, and NKX6.2. OPC8 included the combination of OCT4, OLIG2, NKX6.2, and SOX9. OPC9 included the combination of OCT4, OLIG2, NKX6.1 and SOX9. OPC10 tested the combination of OCT4, SOX9, NKX6.1, and NKX6.2.

Figure 6:
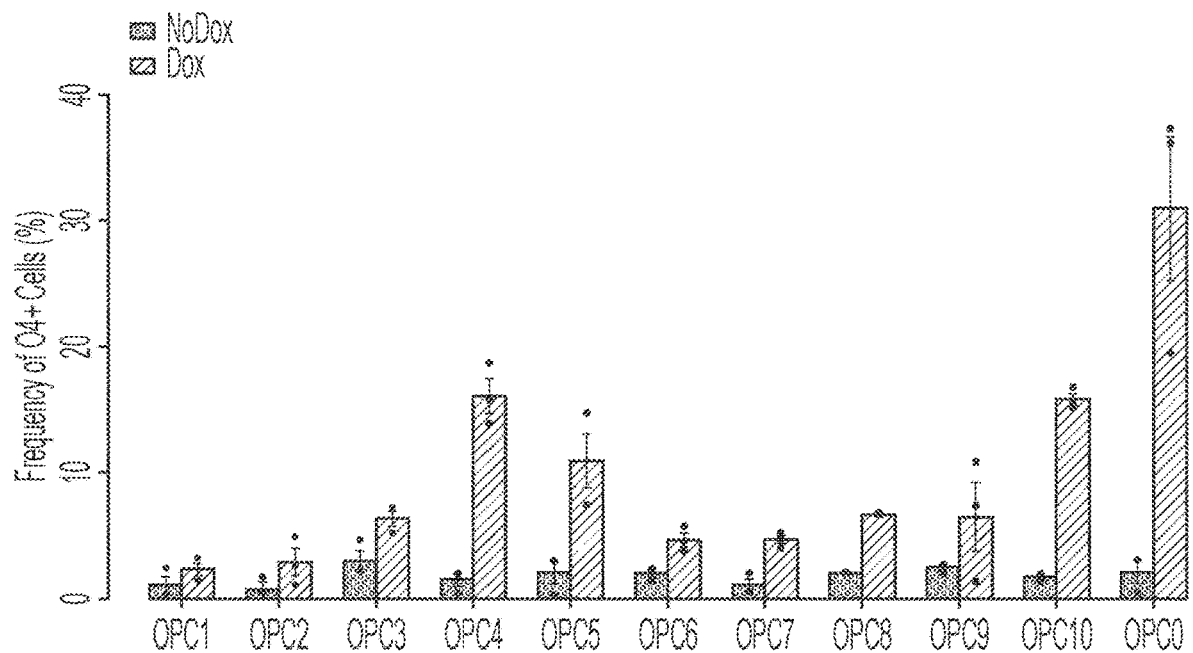
FIG. 6 shows data characterizing cells with the combination of OLIG2, SOX9, NKX6.1, NKX6.2, and OCT4 transcription factors (OPC0) and cells with a subset of the TF combination (OPC1-OPC10) using FACS analysis. The top graph shows quantification of O4 expressing iPSC-derived OPCs at Day 4 (% O4+ cells). Each column is the representation of the mean O4 expression of each independent replicate after 4 days of differentiation in mTeSR media. NoDox (left columns) indicates No doxycycline-induction and Dox (right columns) indicates doxycycline induction. (p<0.05). The bottom chart shows the combination of transcription factors tested in each cell line.

The TFs were nucleofected at high copy numbers into iPSCs. The cells were maintained in mTeSR1 and TF over-expression was induced with doxycycline for four days with no additional external cues. The percentage of O4-expressing cells was measured by anti-O4 antibody staining followed by flow cytometry. The results showed that OPC0 and a few subsets (OPC1-OPC10) were able to form O4+ cells in an efficient manner (FIG. 6, top graph). This study includes different integration loci and varied expression levels of the TFs in each cell colony. These results demonstrate that OPC0 is the most efficient in inducing differentiation of iPSCs into O4 expressing OPCs (FIG. 6, top graph). OPC10 also efficiently induced differentiation of iPSCs into O4 expressing OPCs (FIG. 6, top graph).

Figure 7A:
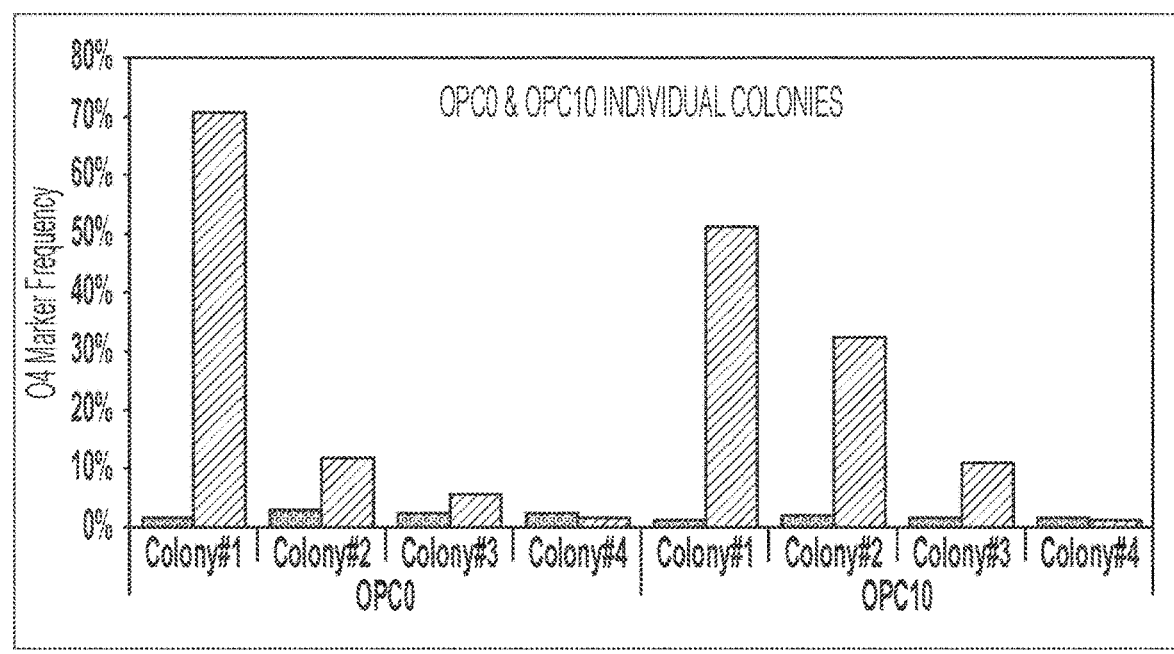
FIGS. 7A-7B include data characterizing the frequency of O4 expressing (O4+) cells in colonies from OPC0 and OPC10 cells. In each graph, the first bar for each colony indicates the frequency of marker-positive cells from cells that were un-induced (no doxycycline treatment, so cells were not induced to express the TFs). The second bar for each colony indicates the frequency of marker-positive cells from cells that were induced to express the TFs (doxycycline-treated cells).
Figure 7B:
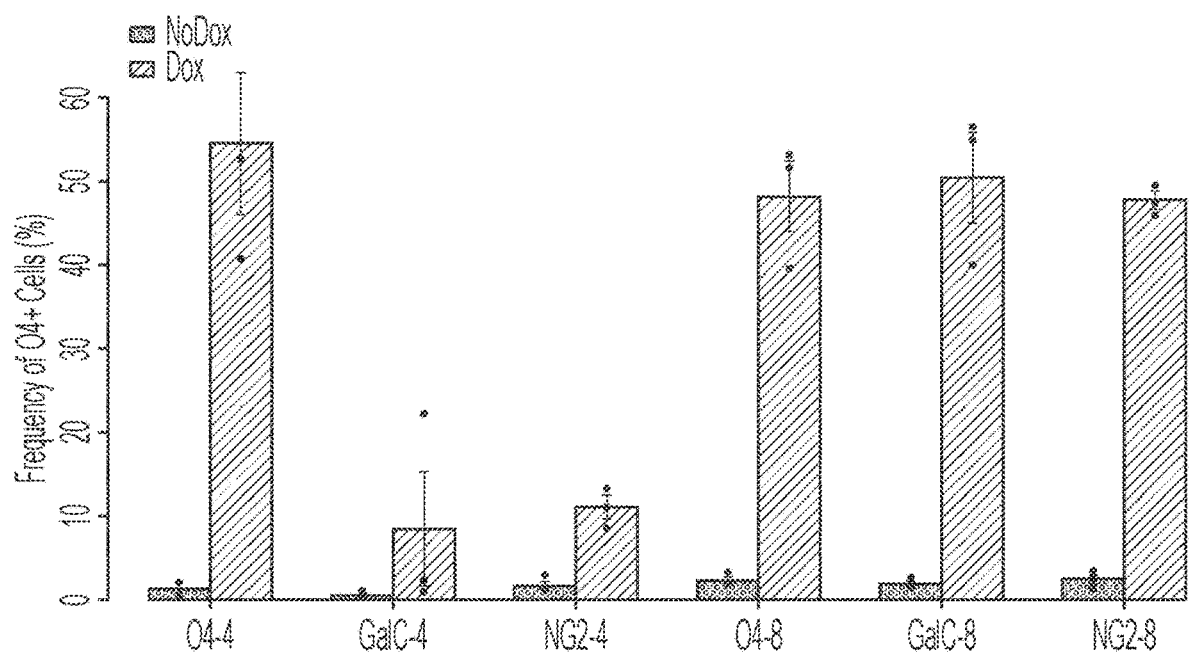

Individual colonies of the two groups with the highest percentage of O4+ cells after 4 days were selected and expanded. Results showed that out of multiple colonies that were assessed, one of the OPC0 colonies (Colony #1) expressed the highest amount of O4 marker (FIG. 7A) and was subsequently analyzed. OPC0-Colony #1 was stained for early, intermediate and late OPC markers and showed the highest expression of O4 marker after 4 days (FIG. 7B). NG2 was used as early stage OPC marker, O4 was used as an intermediate proliferative premitotic OPC marker, and GalC was used as a marker for late stage OPC (post-mitotic) and early mature oligodendrocytes. After 8 days, the cells were also positive for all three markers (FIG. 7B). In addition, cells that were in their final stages of O4 expression were already maturing into GalC expressing cells, a non-proliferative post-mitotic OPC marker (FIG. 7B). These results demonstrate that these cells have the potential to differentiate and mature.

The transcriptome profile of the O4-expressing OPCs that were sorted through fluorescence-activated cell sorting (FACS) was also assessed. The assessment was performed on O4+ cells derived from the OPC9 cell line. Cells were lysed using TRIzol and RNA was extracted using Direct-zol RNA MiniPrep. Three replicates of no doxycycline control cells and three replicates of O4+ cells were processed in parallel in each set of library preps. 1 µg RNA was used for Poly(A) isolation using the NEBNext Poly(A) mRNA Magnetic Isolation Module and NEBNext Ultra Directional RNA Library Prep Kit from Illumina. To prevent library overamplification, a portion of the PCR reaction was amplified by quantitative PCR using SYBR Gold Nucleic Acid Statin on a Roche Lightcycler 480. The remaining reaction was amplified using the number of cycles needed to reach mid-log amplification. The libraries were sequenced on an Illumina MiSeq and sequencing reads were aligned to a human transcriptome reference index using the STAR aligner. Statistical testing was performed using DESeq2's differential expression analysis algorithm. Multiple hypothesis testing was corrected using the False Discovery Rate (FDR) method to generate adjusted p-values. Zero values were imputed to one, and then log 2 transformed values were plotted as a heatmap and clustered by similarity (FIG. 8A). Genes were plotted based on their log 2 fold change compared to hiPSCs and were considered as statistically significant if the adjusted p-value was less than 0.05. A graph comparing the mean of normalized counts and Log 2 fold change is shown in FIG. 8B.

The heatmap showed up-regulation of oligodendrocyte-specific lineage genes, such as OLIG1, PLP1, SOX10, and CSPG4 (NG2) and down-regulation of pluripotency markers such as Nanog (FIG. 8A). SOX10 and OLIG1 are among the top 40 up-regulated genes (FIG. 8C). Olig1 and Sox10 synergistically drive MBP transcription into oligodendrocytes. Sox10 is one of the initial TFs that are expressed after specification of the cells to the oligodendrocyte lineage and in CNS it is only expressed in myelin-forming oligodendroglia. These results confirm the specificity of the generated O4+ cells and their commitment to mature into myelin forming oligodendrocytes using the TF-mediated cell engineering with the five-TF set or its subsets.

Example 3: Production of OPCs Overexpressing IL-10, IFNβ, or the Combination of IL-10 and IFNβ

This example describes production and characterization of stem cell-derived oligodendrocyte progenitor cells (OPCs) overexpressing the cytokines IL-10 and IFNβ, alone and in combination. This example demonstrates that overexpression of IL-10 and/or IFNβ, can stimulate secretion of the anti-inflammatory cytokine IL-10 in engineered OPCs.

Figure 9:
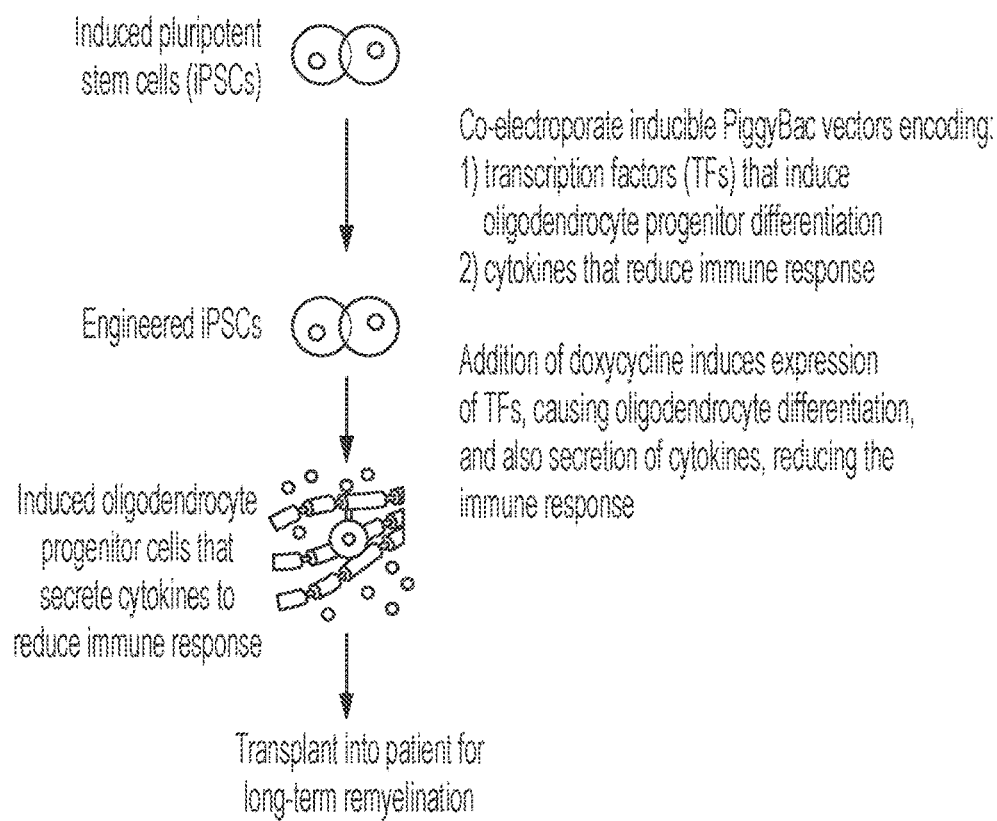
FIG. 9 is a schematic of an example workflow for the production of oligodendrocyte progenitor cells with increased immune-protection.

Induced pluripotent stem cells were co-electroporated with PIGGYBAC™ expression vectors encoding 1) doxycycline-inducible transcription factors (TFs) (SOX9, NKX6.1, OLIG2, and OCT4) that cause the stem cells to differentiate into oligodendrocyte progenitor cells, and 2) doxycycline-inducible cytokines (e.g., IL10 and IFNβ) that thwart the immune response. A schematic of an example workflow from human induced pluripotent stem cells to induced oligodendrocyte progenitor cells that secrete cytokines to reduce immune response and remyelinate axons for therapeutic effect is provided in FIG. 9. Human IL10 and IFNβ were obtained as ORF clones from the Human ORFeome collection (ORFeome Collaboration. *Nat. Meth.* 2016; 13(3):191-192). IL10 and IFNβ were expressed from separate constructs. Puromycin was used to select cells that have successfully integrated these vectors into the genome. Then, differentiation and cytokine release were simultaneously induced with the addition of doxycycline. At different time points, the ability of the cells to secrete the cytokines was assayed by enzyme-linked immunosorbent assay (ELISA).

Figure 10:
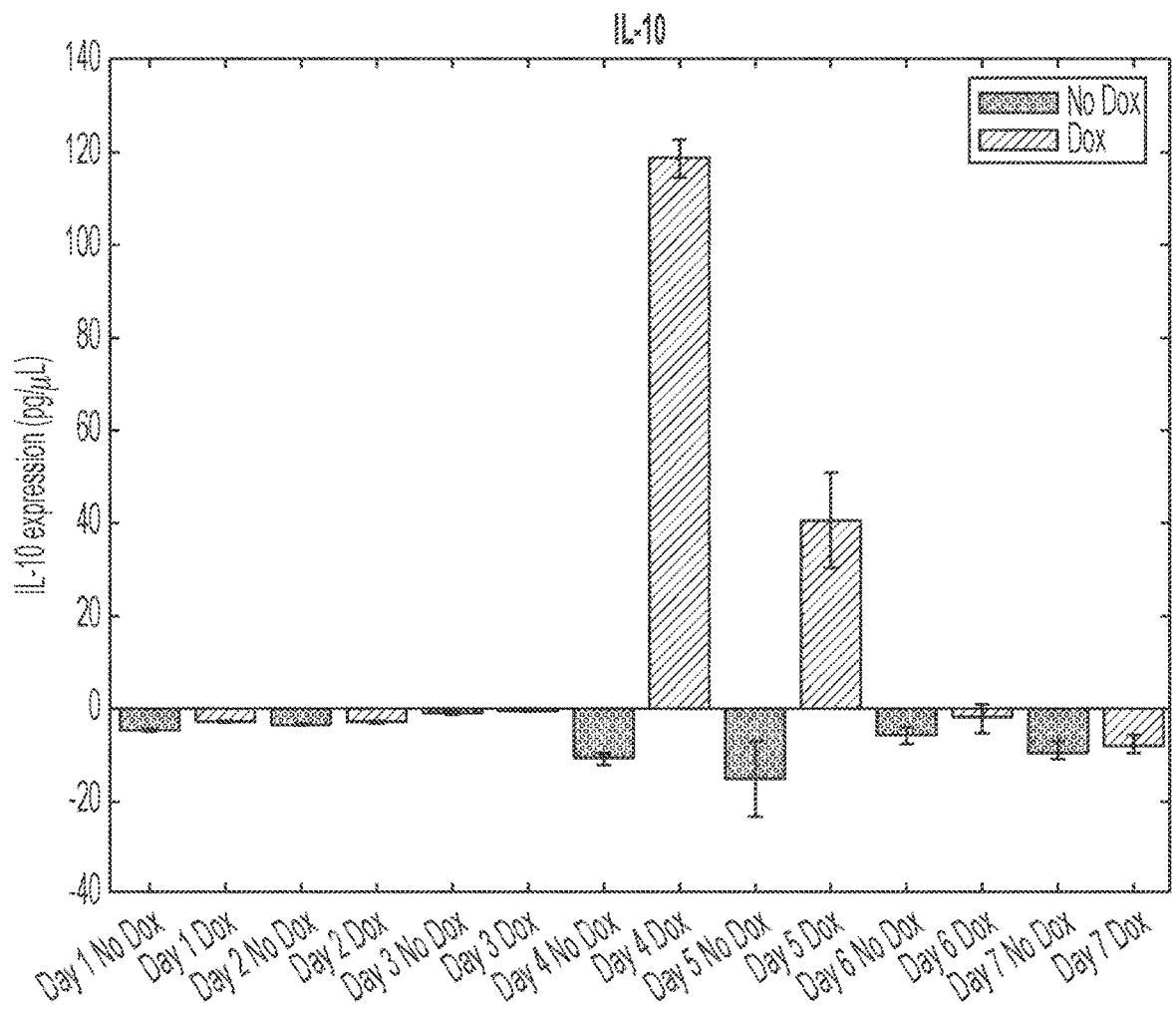
FIG. 10 is a graph of the concentration of secreted IL-10 in cells engineered to overexpress doxycycline-dependent OPC-inducing transcription factors (SOX9, NKX6.1, OLIG2, and OCT4) and doxycycline-dependent IL10 over the course of seven days. Cells were incubated in the presence or absence of doxycycline.
Figure 11:
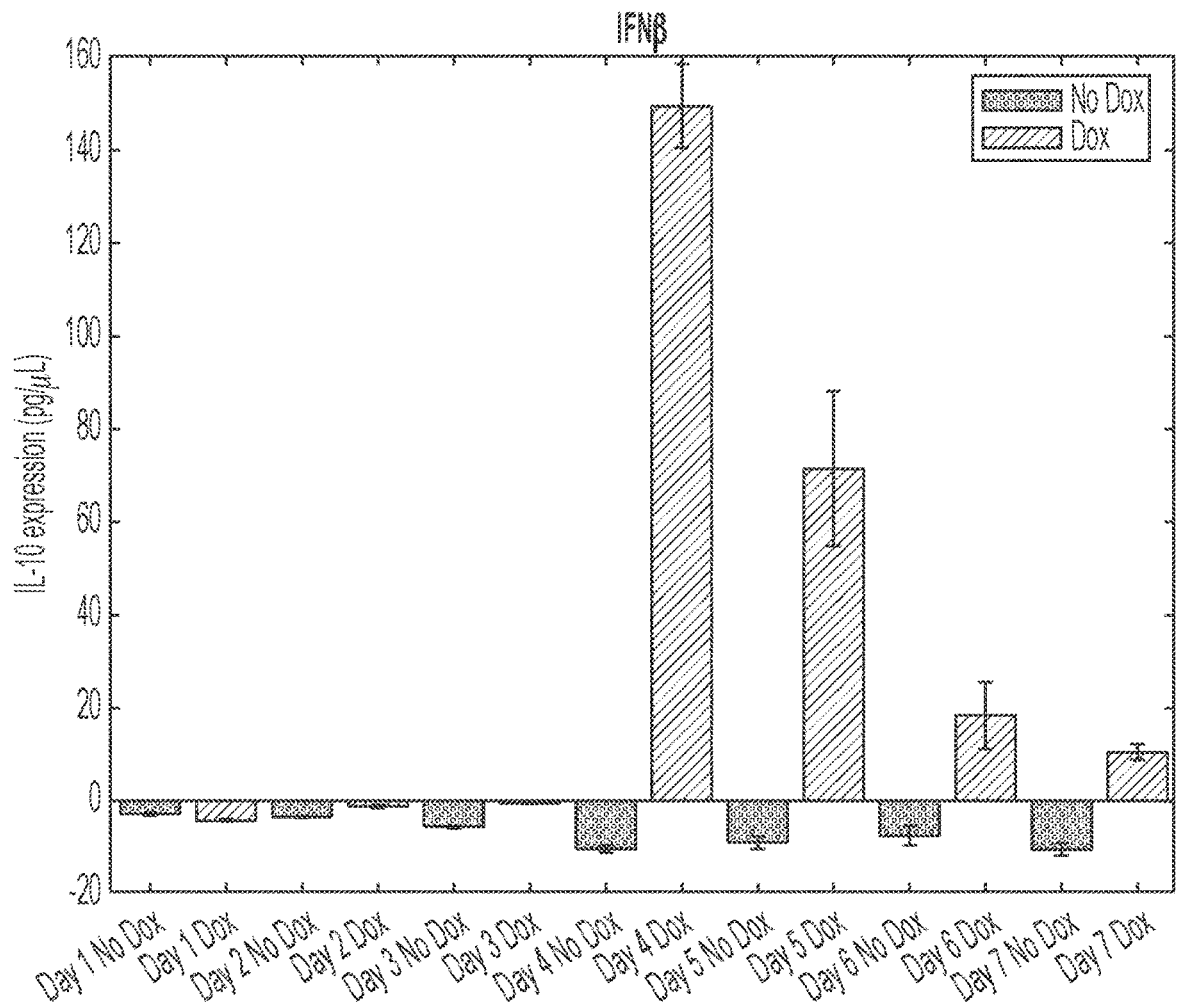
FIG. 11 is a graph of the concentration of secreted IL-10 in cells engineered to overexpress doxycycline-dependent OPC-inducing transcription factors and doxycycline-dependent IFNβ over the course of seven days. Cells were incubated in the presence or absence of doxycycline.

Three different stem cell lines, all with TFs that induce oligodendrocyte differentiation, were generated. In the first line, induced pluripotent stem cells were co-electroporated with the transcription factors and only IL10 (FIG. 10). In the second line, induced pluripotent stem cells were co-electroporated with the transcription factors and only iFNβ (FIG. 11). In the third line, induced pluripotent stem cells were co-electroporated with the transcription factors and both IL10 and IFNβ (FIG. 12).

To determine whether overexpression of IL10 and IFNβ, alone and in combination, could suppress an immune response to engineered OPCs, the levels of secreted IL10 was measured by ELISA assay for each cell line. As shown in FIG. 10, doxycycline treatment induced IL10 secretion in cells co-electroporated with the transcription factors and only IL10. After four days of doxycycline induction, more than 100 pg/μl of secreted IL10 was detected by ELISA assay (FIG. 10). IL10 secretion was observed only in the presence of doxycycline treatment, demonstrating that the induction of IL10 secretion was doxycycline-dependent.

Similarly, as shown in FIG. 11, doxycycline treatment also induced IL10 secretion in cells co-electroporated with the transcription factors and IFNβ. After four days of doxycycline induction, more than 140 pg/μl of secreted IL10 was detected by ELISA assay (FIG. 11). Since IFNβ is upstream of IL10, it is likely that IFNβ secretion promotes IL10 secretion in these cells.

Figure 12:
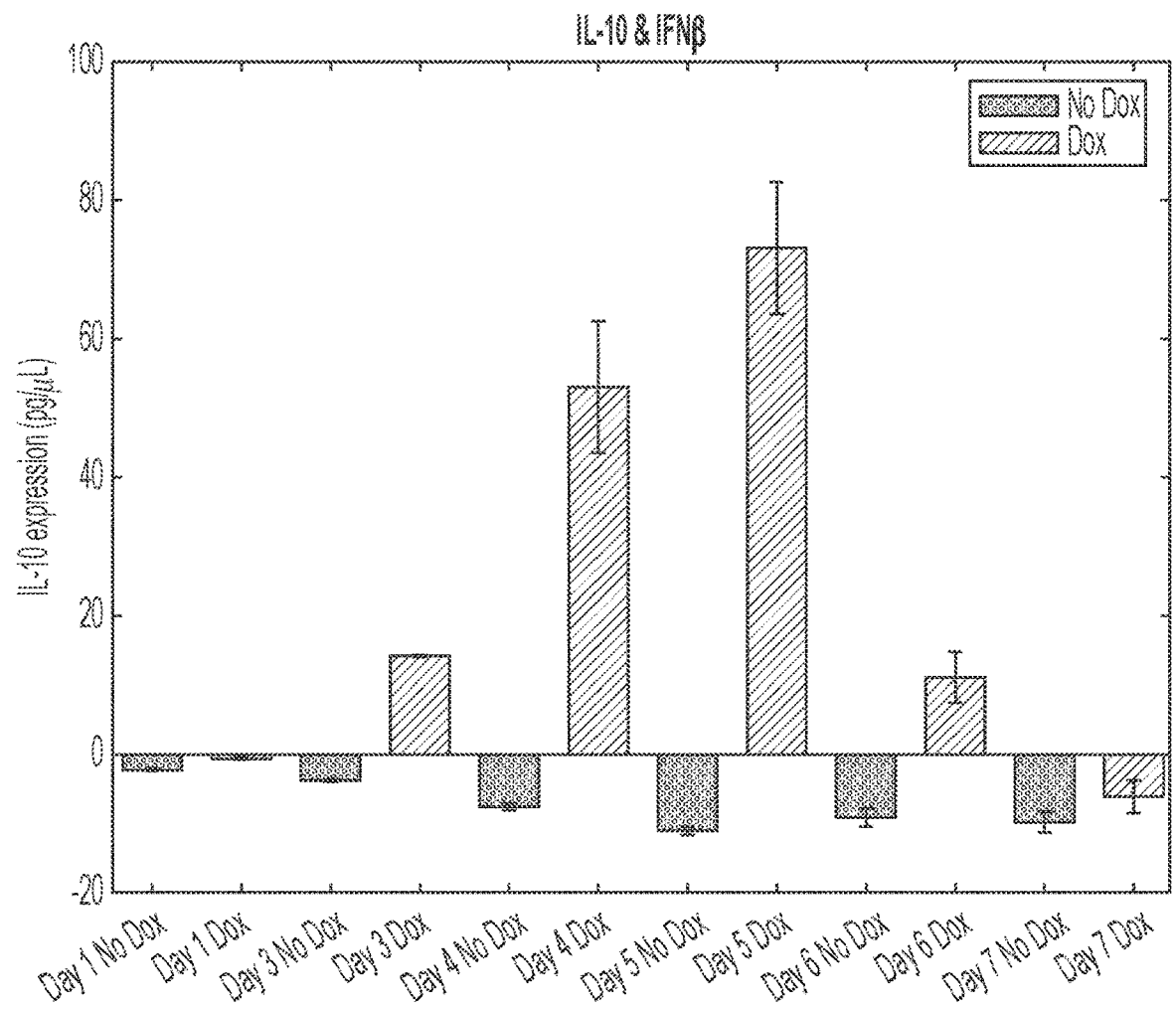
FIG. 12 is a graph of the concentration of secreted IL-10 in cells engineered to overexpress doxycycline-dependent OPC-inducing transcription factors, doxycycline-dependent IL-10, and doxycycline-dependent IFNβ over the course of seven days. Cells were incubated in the presence or absence of doxycycline.

Notably, initial secretion of IL10 was detected as early as 3 days after doxycycline induction in cells co-electroporated with the TFs and both IFNβ and IL10 (FIG. 12). IL10 secretion in these cells peak after 5 days of doxycycline treatment.

Figure 19A:
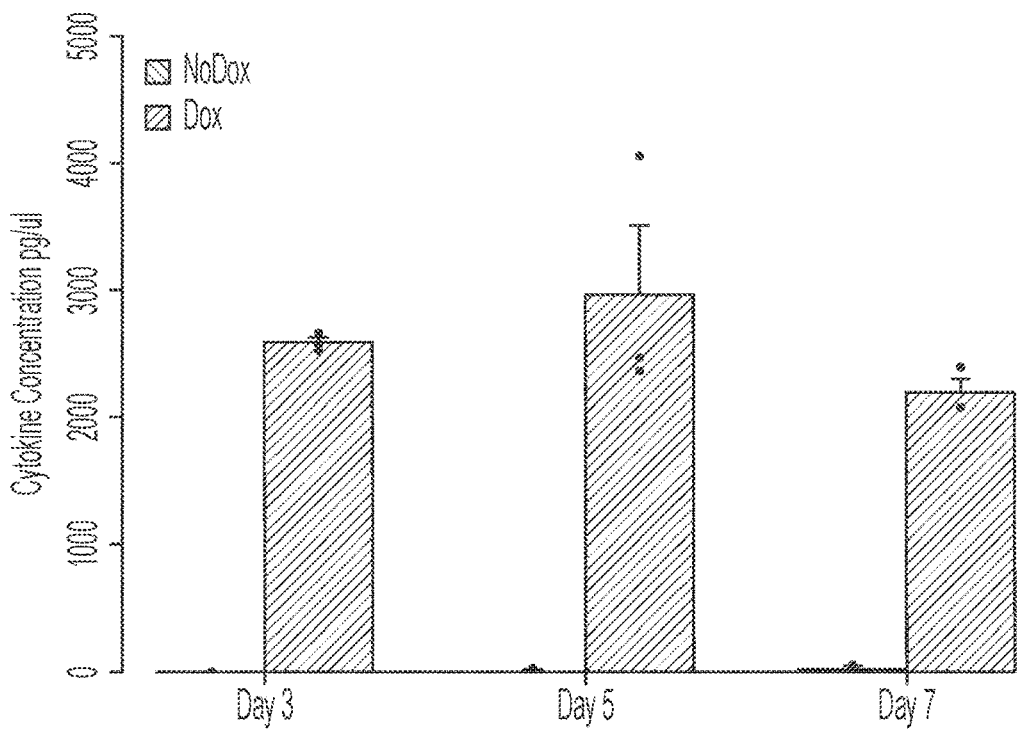
FIGS. 19A-19B include ELISA time course data quantifying IL10 secretion from cells engineered to differentiate into oligodendrocyte progenitors (OPC0: SOX9, NKX6.1, OLIG2, NKX6.2, and OCT4) and to secrete cytokines (IL-10, or IL-10 and IFNβ). Cells were incubated in the presence or absence of doxycycline.
Figure 19B:
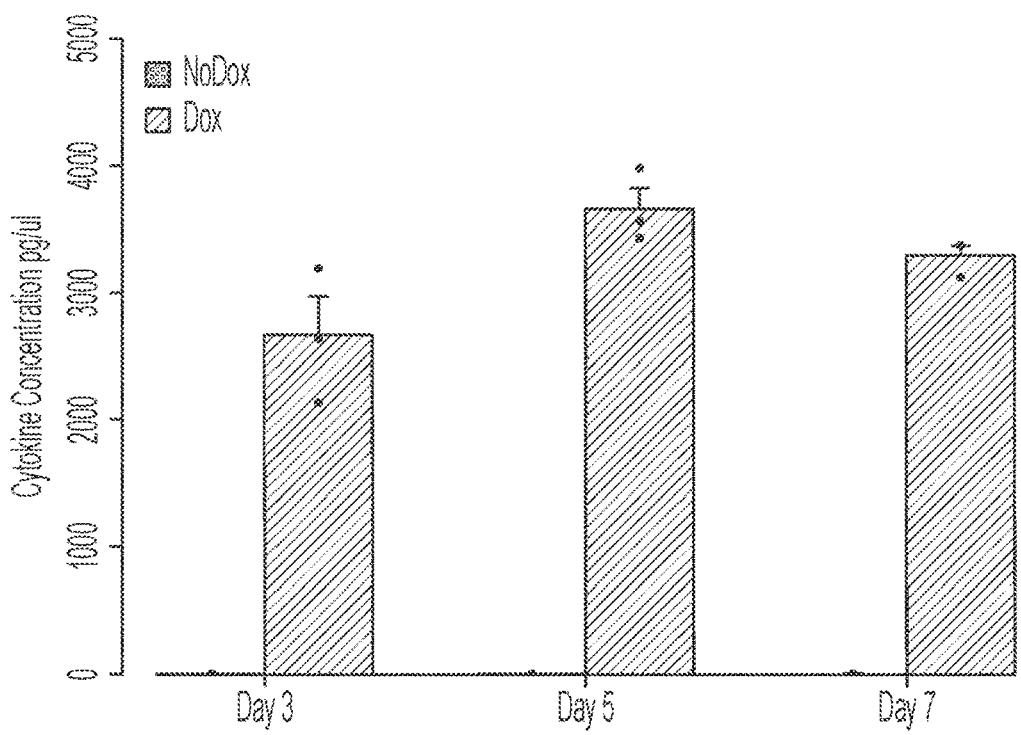

Cytokine-releasing OPCs were also generated to achieve a higher (e.g., 10×) IL-10 secretion level. Cells were engineered to inducibly express SOX9, NKX6.1, O1102, NKX6.2, and OCT4 and to inducibly express cytokines (IL-10 or IL-10 and IFNβ). ELISA showed that secretion reached levels that are 1000-fold higher than control cells (uninduced). A high amount of IL10 secretion from day 3 that persisted to 7 days of doxycycline induction was observed (FIG. 19A). IL10 secretion was not observed in the absence of doxycycline induction. IL10 was also detected when OPCs were engineered to secrete both IL10 and IFN-beta (FIG. 19B).

These results suggest that overexpression of IFNβ and/or IL10 can induce IL10 secretion in stem cell-derived cells (e.g., engineered OPCs), which can then be used to inhibit T-cell reactivity and remyelinate axons for therapeutic effect. For example, while OPCs expressing the autoantigen MBP elicit an immune response in patients with multiple sclerosis, engineered OPCs overexpressing IL-10 and IFNβ would likely be able to suppress an immune response.

Example 4: Vectors for Stable Overexpression of IL10 and IFNβ

Figure 13A:
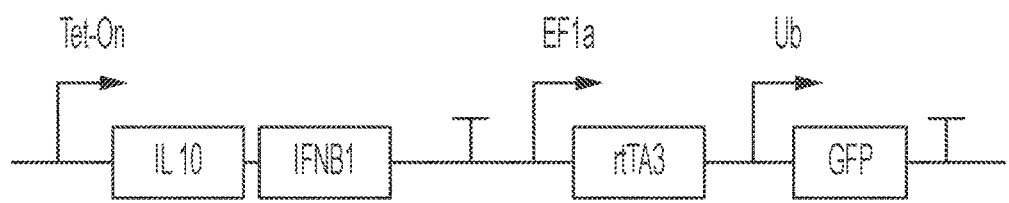
FIGS. 13A-13B include diagrams of vectors for over-expressing IL10 and IFNβ in an orthogonal PIGGYBAC™ vector.

In order to achieve stable overexpression of IL10 and IFNβ, the two constructs may be inserted into PBAN (FIG. 13A). Human IL10 and IFNβ may be obtained as ORF clones from the Human ORFeome collection (ORFeome Collaboration, Nat. Meth. 2016; 13(3):191-192) from Marc Vidal's laboratory (Dana Farber Cancer Institute). To ensure cells express both genes, IL-10 and IFNβ may be stitched together into the same expression unit (IL10_IFNβ) into one vector and then electroporated into stem cells. To select for transfected cells with IL10_IFNβ and TF orthogonally, two selection mechanisms may be applied to the constructs. As the TFs are expressed on a puromycin-resistant vector, IL10_IFNβ constructs may be assembled into a PBAN_GFP vector with GFP as a selection marker. IL10_IFNβ may then be inserted into PBAN_GFP using a Gibson reaction. The cells can then be transfected in order to generate a stable cell line with overexpression of IL-10 and IFNβ simultaneously which may be confirmed by ELISA assay as described above. A functional assay involving T cell proliferation can be performed to assess the extent that IL-10 and IFNβ secretion prevents T cell activation.

Figure 13B:
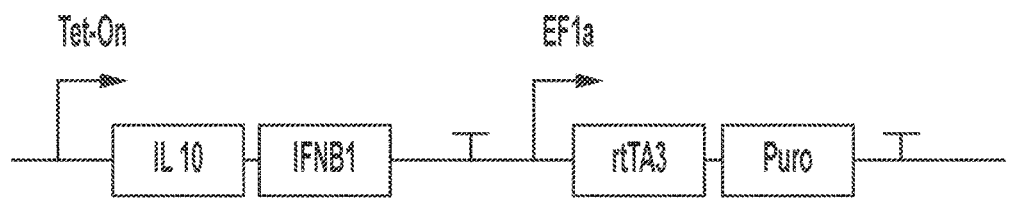

As a non-limiting example, a PBAN vector comprising the elements shown in FIG. 13B was used to overexpress IL10 and IFNβ.

Example 5: Effect of Copy Number on Efficiency of OPC Production

To assess the efficiency of OPC production, two amounts of DNA (high and low) were transfected into hiPSCs, and O4 expression (a marker of oligodendrocyte progenitors) was studied after DNA integration, with or without TF over-expression. The cells were engineered to inducibly express OLIG2, SOX9, NKX6.1, NKX6.2, and OCT4 (colonies are from OPC0). High amount of DNA includes concentrations greater than 1000 ng per 1 million cells. Low amount of DNA includes concentrations less than 1000 ng per 1 million cells. To identify the best performing clones, individual colonies, which were generated by either mechanically dislodging individual colonies or sorting single cells into individual wells, were isolated and studied.

Figure 14A:
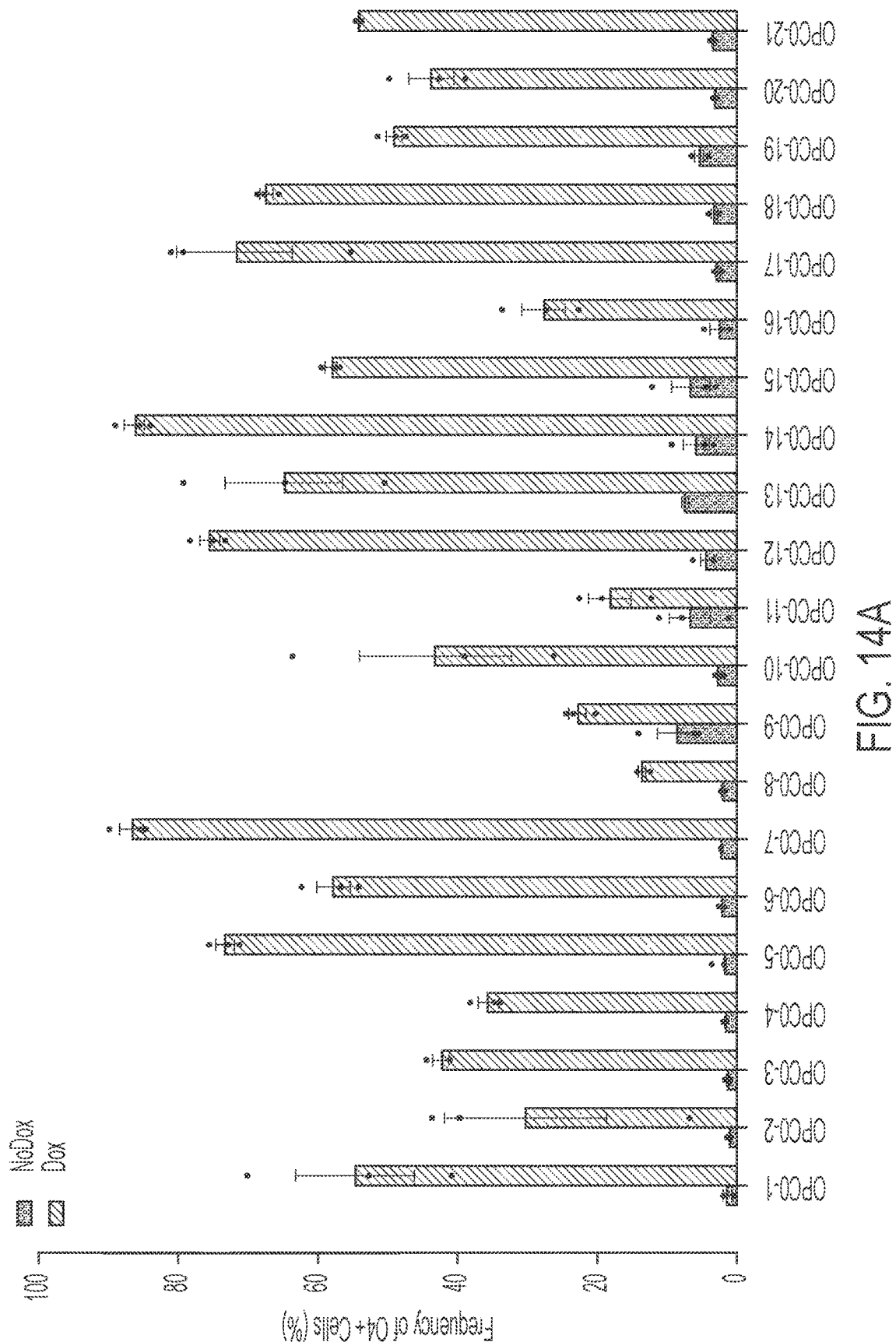
FIGS. 14A-14G differentiation efficiencies of colonies isolated from iPSCs transfected with OLIG2, SOX9, NKX6.1, NKX6.2, and OCT4 (OPC0).
Figure 14B:
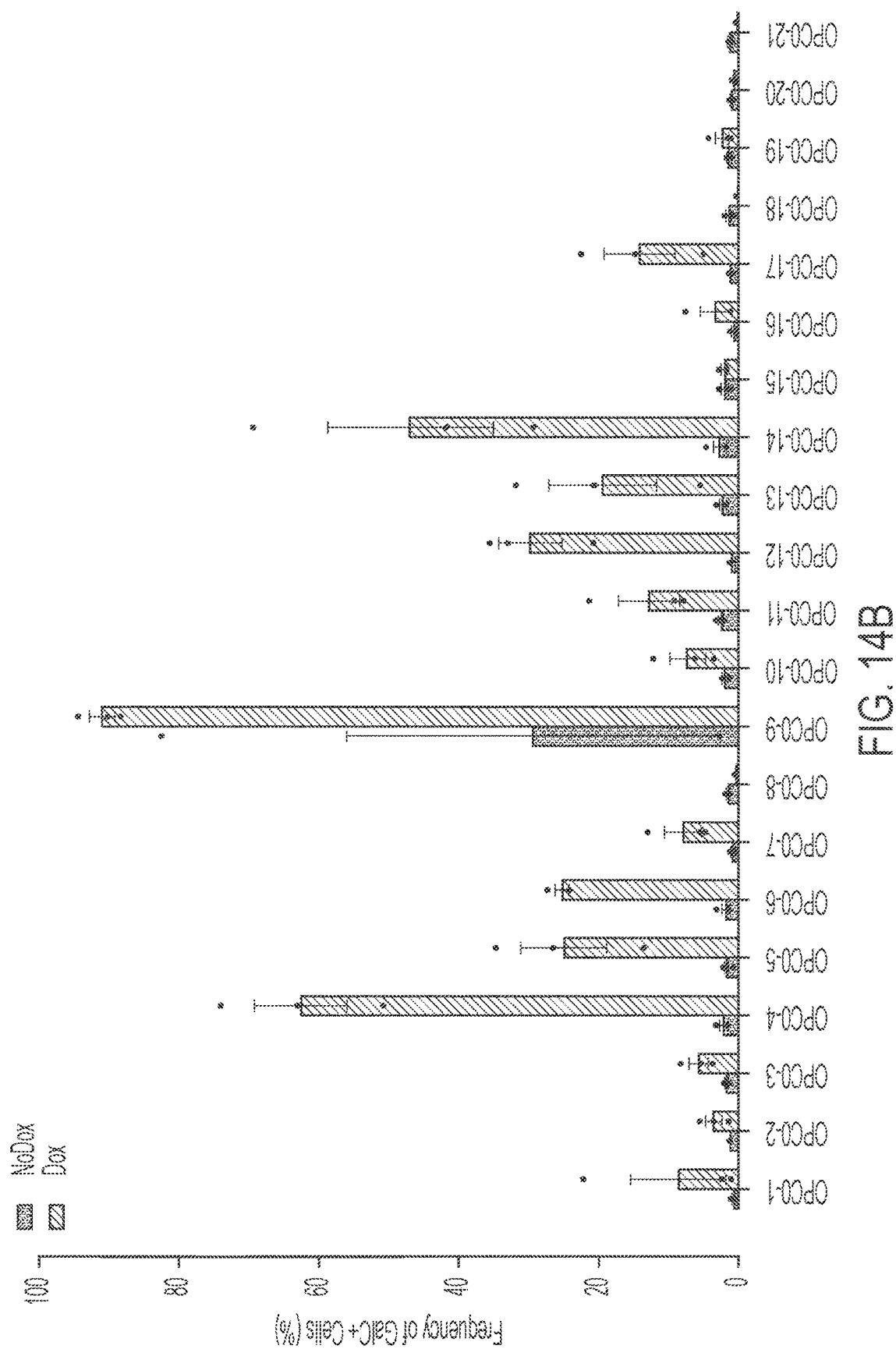
Figure 14C:
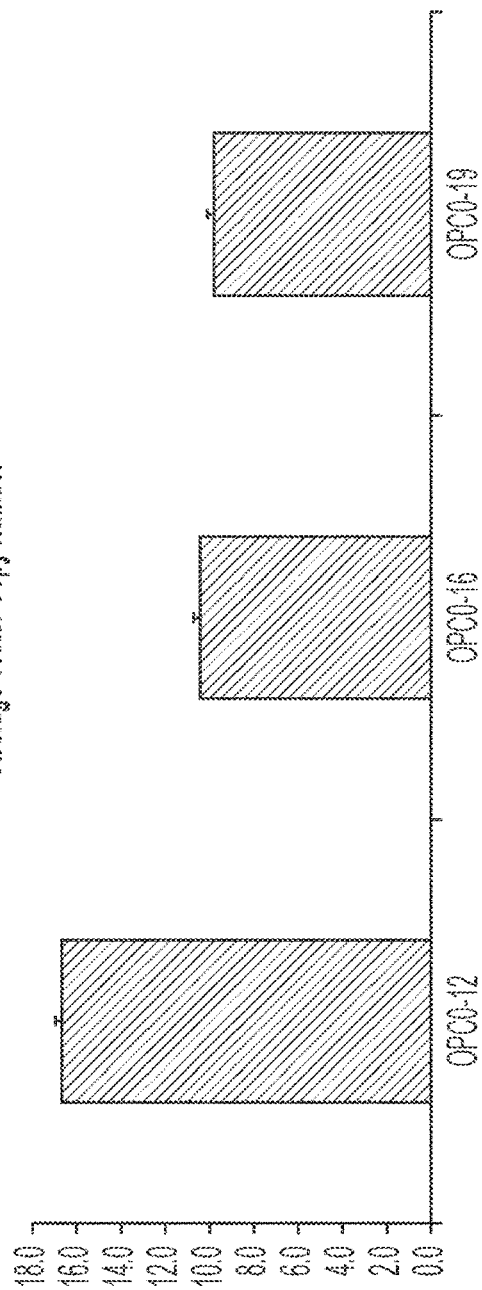
Figure 14D:
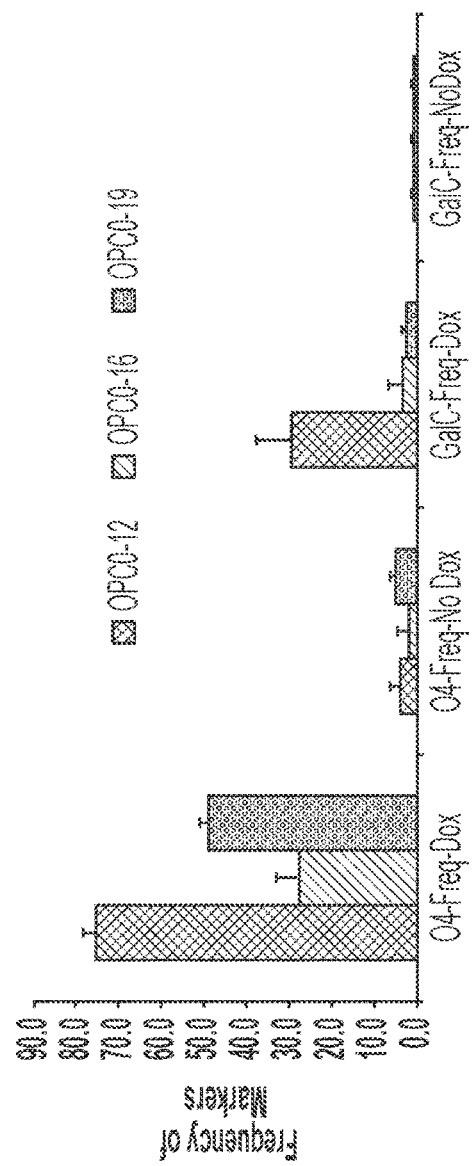
Figures 14E, 14F:
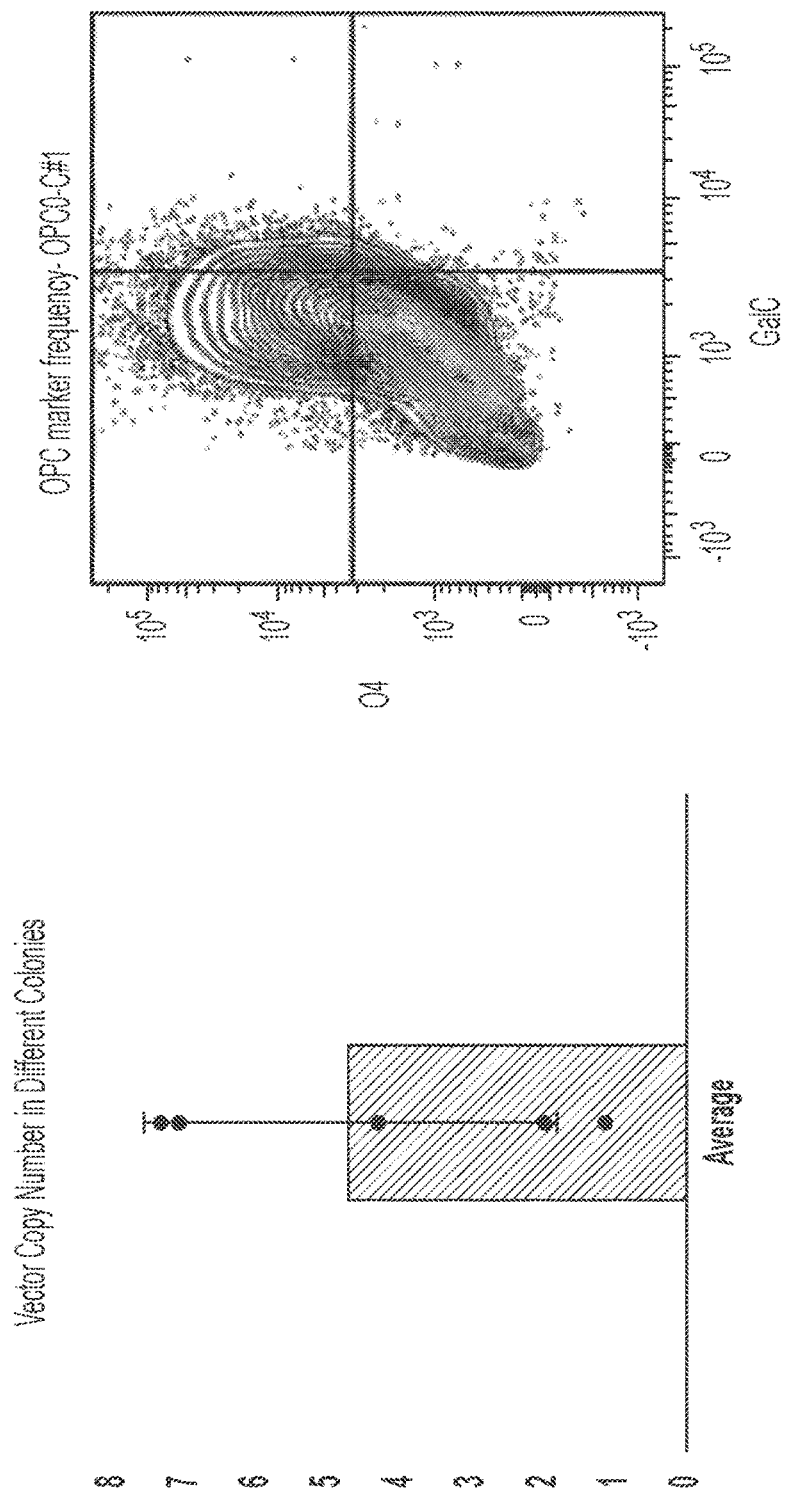
Figure 14G:
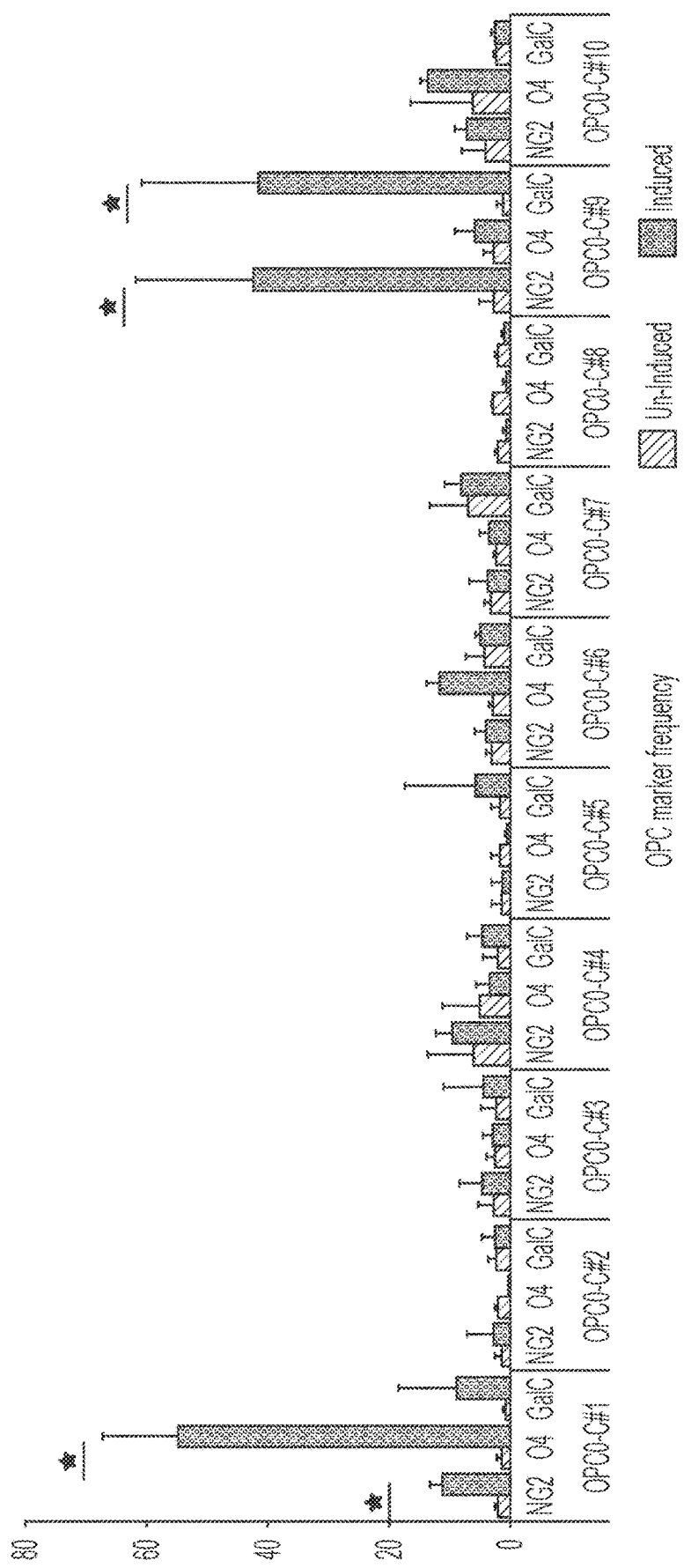

As shown herein, transfecting high amounts of DNA increased the number of colonies with high O4 expression (FIG. 14A—high DNA transfected) compared to transfecting low amounts (FIG. 14G—low DNA transfected). To ensure the differentiated cells remained pre-mitotic—an important cell state for engraftment in vivo—GalC expression (a post-mitotic marker) after induction was measured (FIG. 14B). Ideal colonies should show high O4 expression (FIG. 14A) and low GalC expression (FIG. 14B) after doxycycline induction. Without being bound by a particular theory, the increased efficiency of OPC differentiation using a high amount of transfected DNA may be attributed to an increase in the number of copies of integrated TFs in the genome: cells transfected with high amount of DNA showed more TFs (e.g., ~10-18 copies) integrated into the genome (FIG. 14C) compared to cells transfected with a lower amount of DNA (e.g., ~4-5 copies) (FIG. 14E). A more detailed analysis for O4 and GalC for the best clones are shown in FIG. 14D (high DNA amount) and FIG. 14F (low DNA amount).

Example 6: Further In Vitro Functional Studies of Engineered OPCs

Figure 15A:
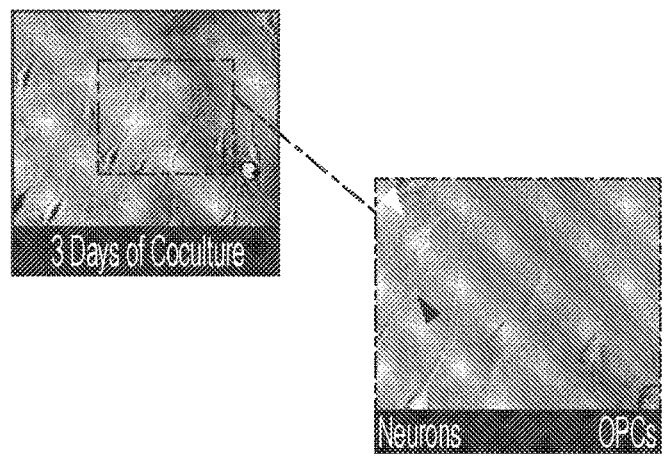
FIGS. 15A-15B show that the engineered OPCs could form myelin sheath in vitro. Cells from OPC0, colony 1, which were engineered to inducibly express OLIG2, SOX9, NKX6.1, NKX6.2, and OCT4, were used.
Figure 15B:
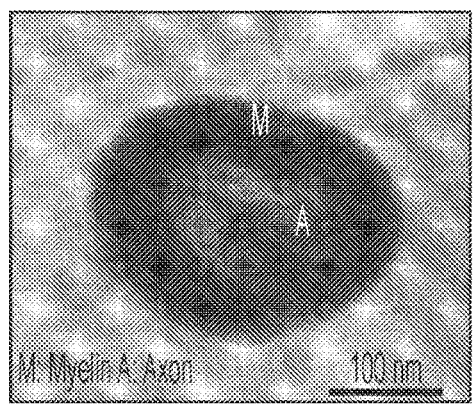

Next, it was demonstrated that the engineered OPCs were functional. An in vitro assay, where the engineered OPCs were co-cultured with hiPSC-induced neurons, was used. After 3 days. OPCs contacting the neurites of induced neurons were observed (FIG. 15A). In FIG. 15A, OPCs from OPC0 colony 1, which was engineered to inducibly express OLIG2, SOX9, NKX6.1, NKX6.2, and OCT4, was used. To assess whether the engineered OPCs could form myelin sheath in vitro, this co-culture was continued for a total of four weeks. Then, the cells were fixed, a cross-section was obtained, and electron microscopy was performed. Robust myelin formation around axons was observed, demonstrating functional myelination in vitro (FIG. 15B).

Figure 20:
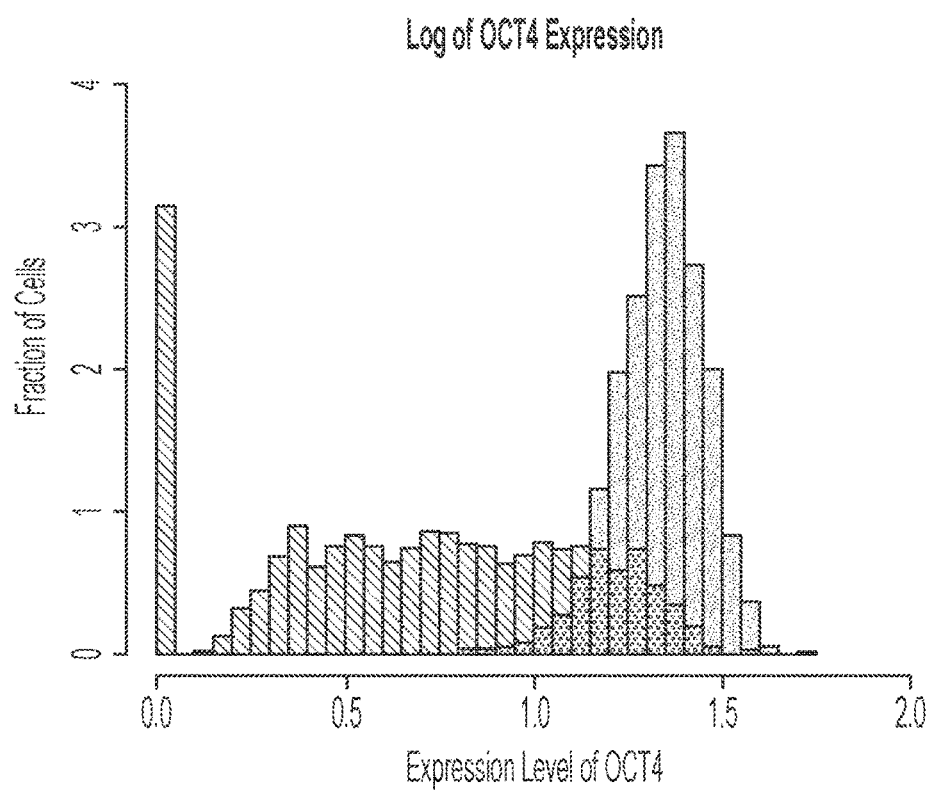
FIG. 20 is a histogram showing OCT4 expression at the single cell level of cells from OPC0, colony 1, which were engineered to inducibly express OLIG2, SOX9, NKX6.1, NKX6.2, and OCT4. The rightmost peak are cells that have not been treated with doxycycline and therefore remain OCT4-positive stem cells. The leftmost peak and peak with no OCT4 expression (shaded) are cells treated with doxycycline after four days.

To assess the purity of the programmed OPCs, single cell RNA-Seq using oil-droplet emulsions on thousands of single cells was conducted using 10× Genomics' Chromium single cell RNA-seq kit according to manufacturer's instructions, t-SNE (t-distributed stochastic neighbor embedding) plot analysis of CNP, PLP1, and NES expression was conducted. A two-dimensional plot was generated for each gene (CNP, PLP1, and NES) and each point in each plot represented a single cell's transcriptome projected. A single, coherent population of cells, with no sub-populations, was observed, suggesting the programming process was highly pure. It was found that oligodendrocyte-specific markers, such as PLP1 and CNP, were up-regulated as a relatively pure population concordant with the down-regulation of pluripotency genes in the majority of the cell population after four days of induction (data not shown). FIG. 20 is a histogram showing OCT4 expression at the single cell level of cells from OPC0, colony 1, which were engineered to inducibly express OLIG2, SOX9, NKX6.1, NKX6.2, and OCT4. The rightmost peak are cells that have not been treated with doxycycline and therefore remain OCT4-positive stem cells. The leftmost peak and peak with no OCT4 expression (shaded) are cells treated with doxycycline after four days.

This data provides strong evidence that the OPCs programmed within four days with no additional soluble factors are bonafide OPCs.

Example 7: Use of Engineered OPCs to Myelinate Human Organoids

Figure 16A:
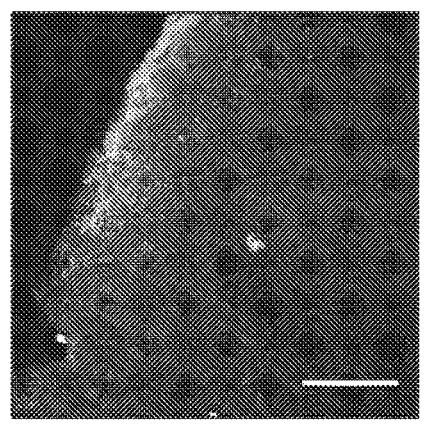
FIGS. 16A-16C show that engineered and differentiated OPCs can myelinate human cerebral organoids. Cells from OPC0, colony 1, which were engineered to inducibly express OLIG2, SOX9, NKX6.1, NKX6.2, and OCT4, were used.
Figure 16B:
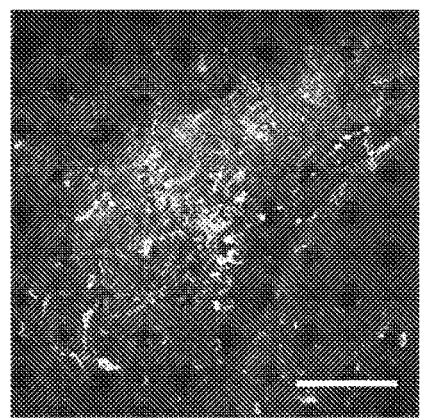
Figure 16C:
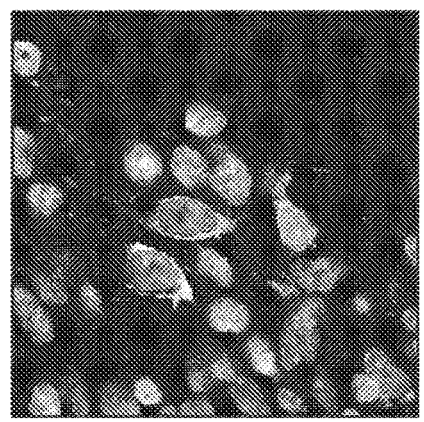

To determine whether the programmed OPCs could form myelin in in vivo-like conditions, human organoids were used. The OPCs were from OPC0, colony 1, which were engineered to inducibly express OLIG2, SOX9, NKX6.1, NKX6.2, and OCT4. To further improve the clinical translation of these programmed OPCs, the human cerebral organoid model was used to evaluate these cells' ability to myelinate human organoids, which feature complex spatial organization and an ensemble of cell types found in human brains. Unmodified hiPSCs were mixed with hiPSCs that could be induced to differentiate into OPCs upon doxycycline addition. After the cerebral organoids were formed without doxycycline, and doxycycline was added to induce differentiation of OPCs in the subset of engineered hiPSCs. After 8 weeks, the human cerebral organoids were sectioned and stained for myelin basic protein (MBP) and for myelin oligodendrocyte glycoprotein (MOG). MOG expression was observed in organoids treated with doxycycline to induce OPC differentiation, but not in organoids cultured without doxycycline (FIGS. 16A-16B). MBP expression was also observed in organoids treated with doxycycline to induce OPC differentiation (FIG. 16C). This in vivo-like human model demonstrates the ability of programmed OPCs to myelinate human neurons.

Example 8: Administration of Engineered OPCs Improved Motor Function in the Shiverer Mouse Model To determine the myelin-forming ability of the engineered OPCs in vivo, the cells were transplanted into the MBP-deficient Shi/Shi Shiverer mouse model. The OPCs were from OPC0, colony 1, which were engineered to inducibly express OLIG2, SOX9, NKX6.1, NKX6.2, and OCT4. The Shiverer mouse has multiple exon deletions in its MBP gene, leading to minimal MBP protein expression and subsequently a lack of myelin production. This model is the standard animal model that is used to confirm myelin generation in vivo. As these mouse models lack myelin, the mouse models were utilized as an assessment of the myclin forming abilities of our cells in vivo. Any expression of exogenous MBP (or other myelin markers) after cell injection in animals demonstrates that the injected cells promote of myelin formation and are functional. Homozygous Shiverer mice were housed under appropriate conditions with food and water provided and were crossed with heterozygous mice under standard IACUC protocols. Newborn mice (postnatal day=0-3) were cryoanesthesized and ~5×10$^4$ in 2 μl PBS of cells were injected intracranially using freehand injection while a control group (postnatal day=0-3) received PBS injection.

To perform a behavioral test of motor function, a hind limb suspension test was performed 10 weeks after injection. The mice were suspended by their hind limbs from the lip of a standard 50 ml glass beaker and the posture adopted is scored according to the following criteria: score of 4 indicates normal hind-limb separation with tail raised; score of 3, weakness is apparent and hind limbs closer together but seldom touching each other; score of 2, hind limbs are close to each other and often touching; score of 1, weakness apparent and the hind limbs are almost always in a clasped position with the tail raised; a score of 0 indicates constant clasping of the hind limbs with the tail lowered or failure to hold onto the tube.

The control-untreated healthy mouse had a hind limb suspension score of 4 and the control-untreated Shiverer mice had a lower score of 3 (data not shown). Notably, a Shiverer mouse injected with OPCs had a score of 4, which is the same as the healthy control-untreated mice (data not shown). Thus, the hind limb suspension test demonstrated that the treated Shiverer mouse received a better clinical score 10 weeks after injection compared to the untreated Shiverer mice.

Figure 18B:
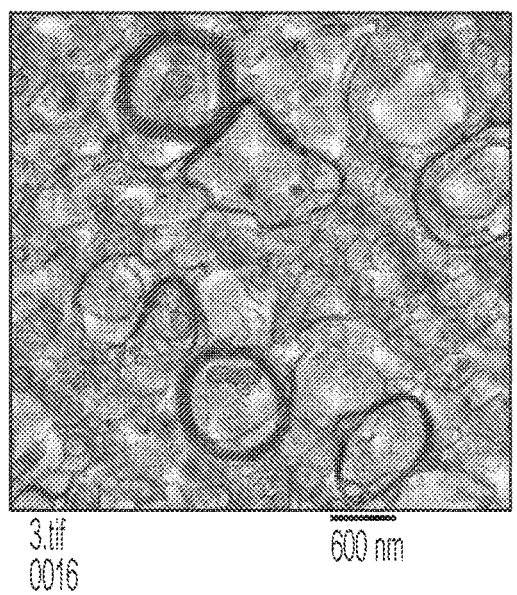
Figure 18C:
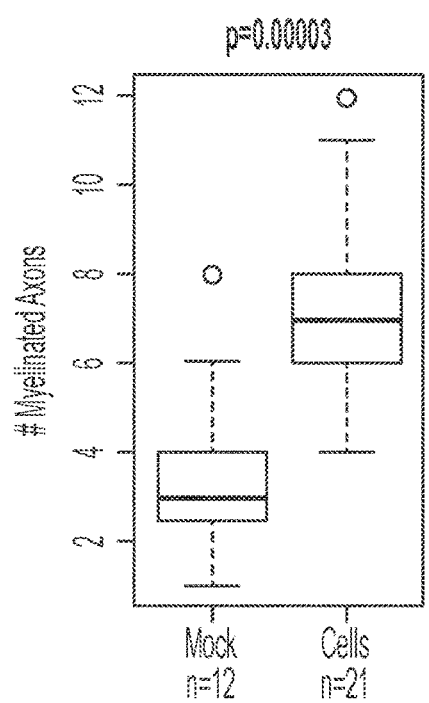
Figure 18D:
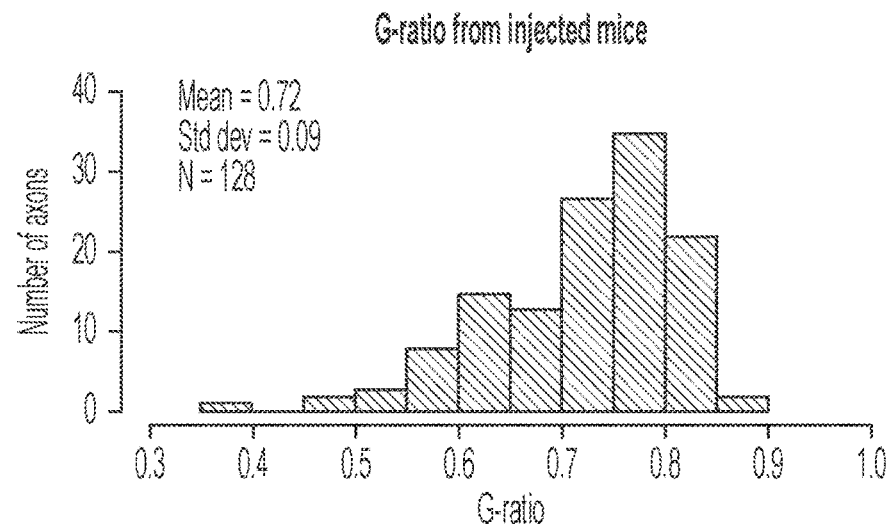

To show the improvement in physiological score was due to myelin growth in a mouse treated with the engineered OPCs, mouse brains were sectioned and stained for myelin. OPC-injected mice stained positive for myelin (FIG. 17B). For reference, healthy mice (fully stained, FIG. 17A) and non-injected mice are shown (no staining, FIG. 17C). The number of myelinated axons was also quantified using transmission electron microscopy (TEM) images. These images show an increase in the number of myelinated axons (FIG. 18B) compared to PBS controls (FIG. 18A). This is quantified in FIG. 18C. The G-ratio quantifies the amount of myelin, with lower numbers showing thicker myelin. FIG. 18D shows the distribution of G-ratio's similar to those found in vivo. The axonal g-ratio range was on average between 0.6 and 0.8.

Example 9: Administration of Engineered OPCs to an Experimental Autoimmune Encephalomyelitis (EAE) Model of Multiple Sclerosis An experimental autoimmune encephalomyelitis model (EAE) was developed. The EAE model is a standard model for human inflammatory demyelinating diseases such as multiple sclerosis. This model has similar manifestations of the disease such as inflammation, gliosis, and axonal and myelin loss.

In the study described herein, mice were acclimated to the facility for at least 7 days prior to the start of the study. All mice were the same age within 1 week. EAE will be induced in all mice as follows:

| Day 0, Hour 0: | Immunization with MOG35-55/CFA |
| --- | --- |
| Day 0, Hour 2: | Injection of pertussis toxin |
| Day 1, Hour 0: | 2nd injection of pertussis toxin (24 hours after initial immunization) |

Mice were injected subcutaneously at two sites in the back with the emulsion component (containing MOG35-55) of Hooke Kit™ MOG35-55/CFA Emulsion PTX, catalog number EK-2110 (Hooke Laboratories. Lawrence MA). One site of injection was done in the upper back, approximately 1 cm caudal of the neck line. The second site was in the lower back, approximately 2 cm cranial of the base of the tail. The injection volume was 0.1 mL at each site. Within 2 hours of the injection of emulsion, and then again 24 hours after the injection of emulsion, the pertussis toxin component of the kit was administered intraperitoneally. After disease induction, mice were assigned to groups in a balanced manner to achieve similar average weight across the groups at the start of the study (Day −2).

Survival rate, weight loss and both cumulative and maximum score of each animal will be recorded.

Table 1 below gives the treatment administered to each group. In Table 1. Dox indicates doxycycline and i.v. indicates intravenous administration of indicated engineered OPCs. Twelve (12) animals were used in each group. Test cells A are iPSCs that are capable of expressing SOX9, OLIG2, NKX6.1, NKX6.2, OCT4, IL10, and IFN-beta in the presence of doxycycline.

TABLE 1

Diet and Treatment Regimen of EAE mice.

| Group | Diet | Start of diet | Treatment | Dose | Volume | Day of treatment | Route | Purpose |
| --- | --- | --- | --- | --- | --- | --- | --- | --- |
| 1 | Dox | Day-2 | Vehicle | — | 150 μL/mouse | Day 0, Day 7 | i.v. | Negative control |
| 2 | Dox | Day-2 | Test cells A | 2M cells/ms | 150 μL/mouse | Day 7 | i.v. | Test |

Figure 21A:
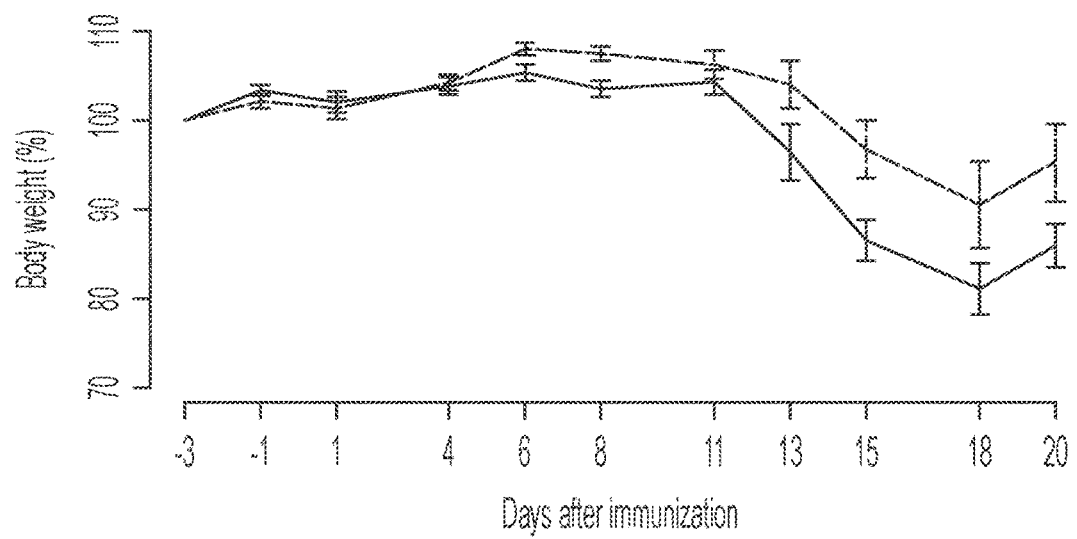
FIGS. 21A-21B show adoptive transfer EAE mouse model with or without intravenous injection of hiPSC-derived OPCs engineered to secrete both IL10 and IFNβ.

To study the effect of the cocktail-iPSCs (engineered to inducibly express SOX9, OLIG2, NKX6.1, NKX6.2, OCT4, IL10, and IFN-beta), mice were intravenously (i.v.) injected with cocktail-iPSCs ($2 \times 10^6$ cell/mouse) into mice seven days post EAE induction while animals were kept on a doxycycline diet throughout the study. The weight loss and disease progression were monitored in both groups (the vehicle and injected group). The results of the adoptive transfer EAE mouse model with or without intravenous injection of hiPSC-derived OPCs engineered to secrete both IL10 and IFNβ are shown in FIGS. 21A-21B.

Figure 21B:
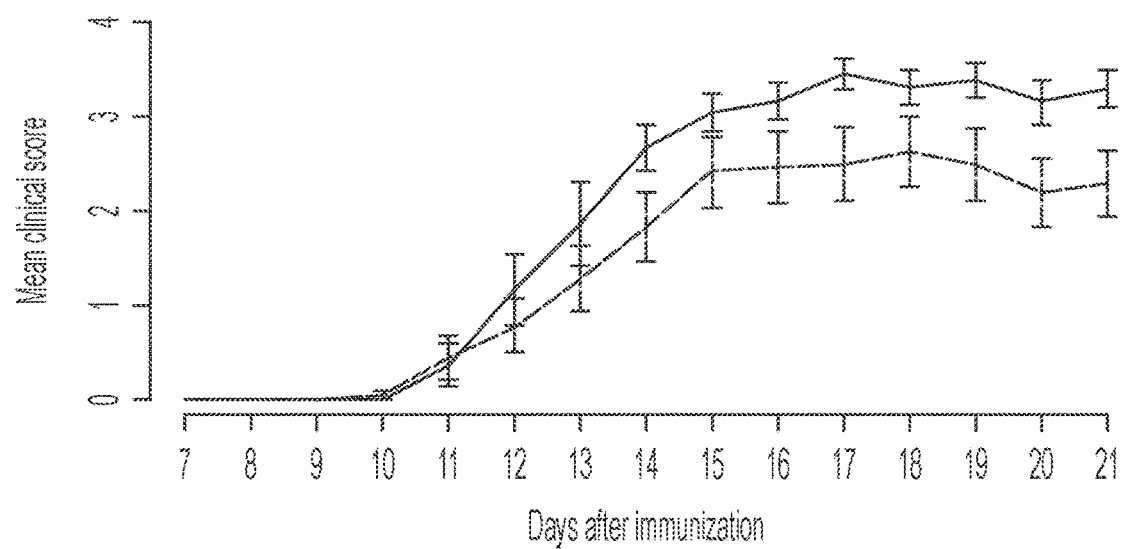

The vehicle demonstrated a progressive increase in clinical score from days 10 while a reduction in the clinical score was observed in mice treated with cocktail-iPSCs (P<0.05) (FIG. 21B).

In the experimental group, 2 mice had no disease presentation and there were 0 deaths. All control mice had significant symptom presentation and one died (maximum score=5). Disease reversal from peak presentation in the experimental group include a 1 point reversal in 2 experimental vs 1 control mice, 0.5 point reversal in 5 experimental vs 2 control mice, and progression in 2 experimental vs 8 control mice. One experimental mouse had stable disease.

Example 10: Non-Limiting Examples of Nucleic Acid and Amino Acid Sequences Encoding Transcription Factors Non-limiting examples of nucleic acid and amino acid sequences encoding transcription factors are provided below. The nucleic acid sequences provided below were used in the examples described above.

Nucleic acid sequence encoding NKX6.1:
(SEQ ID NO: 1)
ATGTTAGCGGTGGGGCAATGGAGGGCACCCGGCAGAGCGCATTCCTGC

TCAGCAGCCCTCCCCTGGCCGCCCTGCACAGCATGGCCGAGATGAAGAC

CCCGCTGTACCCTGCCGCGTATCCCCCGCTGCCTGCCGGCCCCCCCTCC

TCCTCGTCCTCGTCGTCGTCCTCCTCGTCGCCCTCCCCGCCTCTGGGCA

CCCACAACCCAGGCGGCCTGAAGCCCCCGGCCACGGGGGGGCTCTCATC

CCTCGGCAGCCCCCCGCAGCAGCTCTCGGCCGCCACCCCACACGGCATC

AACGATATCCTGAGCCGGCCCTCCATGCCCGTGGCCTCGGGGGCCGCCC

TGCCCTCCGCCTCGCCCTCCGGTTCCTCCTCCTCCTCTTCCTCGTCCGC

CTCTGCCTCCTCCGCCTCTGCCGCCGCCGCGGCTGCTGCCGCGGCCGCA

GCCGCCGCCTCATCCCCGGCGGGGCTGCTGGCCGGACTGCCACGCTTTA

GCAGCCTGAGCCCGCCGCCGCCGCCGCCCGGGCTCTACTTCAGCCCCAG

CGCCGCGGCCGTGGCCGCCGTGGGCCGGTACCCCAAGCCGCTGGCTGAG

-continued

CTGCCTGGCCGGACGCCCATCTTCTGGCCCGGAGTGATGCAGAGCCCGC

CCTGGAGGGACGCACGCCTGGCCTGTACCCCTCATCAAGGATCCATTTT

GTTGGACAAAGACGGGAAGAGAAAACACACGAGACCCACTTTTTCCGGA

CAGCAGATCTTCGCCCTGGAGAAGACTTTCGAACAAACAAAATACTTGG

CGGGGCCCGAGAGGGCTCGTTTGGCCTATTCGTTGGGGATGACAGAGAG

TCAGGTCAAGGTCTGGTTCCAGAACCGCCGGACCAAGTGGAGGAAGAAG

CACGCTGCCGAGATGGCCACGGCCAAGAAGAAGCAGGACTCGGAGACAG

AGCGCCTCAAGGGGGCCTCGGAGAACGAGGAAGAGGACGACGACTACAA

TAAGCCTCTGGATCCCAACTCGGACGACGAGAAAATCACGCAGCTGTTG

AAGAAGCACAAGTCCAGCAGCGGCGGCGGCGGCGGCCTCCTACTGCACG

CGTCCGAGCCGGAGAGCTCATCC

Nucleic acid sequence encoding SOX9:

(SEQ ID NO: 2)
ATGAATCTCCTGGACCCCTTCATGAAGATGACCGACGAGCAGGAGAAGG
GCCTGTCCGGCGCCCCCAGCCCCACCATGTCCGAGGACTCCGCGGGCTC
GCCCTGCCCGTCGGGCTCCGGCTCGGACACCGAGAACACGCGGCCCCAG
GAGAACACGTTCCCCAAGGGCGAGCCCGATCTGAAGAAGGAGAGCGAGG
AGGACAAGTTCCCCGTGTGCATCCGCGAGGCGGTCAGCCAGGTGCTCAA
AGGCTACGACTGGACGCTGGTGCCCATGCCGGTGCGCGTCAACGGCTCC
AGCAAGAACAAGCCGCACGTCAAGCGGCCCATGAACGCCTTCATGGTGT
GGGCGCAGGCGGCGCGCAGGAAGCTCGCGGACCAGTACCCGCACTTGCA
CAACGCCGAGCTCAGCAAGACGCTGGGCAAGCTCTGGAGACTTCTGAAC
GAGAGCGAGAAGCGGCCCTTCGTGGAGGAGGCGGAGCGGCTGCGCGTGC
AGCACAAGAAGGACCACCCGGATTACAAGTACCAGCCGCGGCGGAGGAA
GTCGGTGAAGAACGGGCAGGCGGAGGCAGAGGAGGCCACGGAGCAGACG
CACATCTCCCCCAACGCCATCTTCAAGGCGCTGCAGGCCGACTCGCCAC
ACTCCTCCTCCGGCATGAGCGAGGTGCACTCCCCCGGCGAGCACTCGGG
GCAATCCCAGGGCCCACCGACCCCACCCACCACCCCCAAAACCGACGTG
CAGCCGGGCAAGGCTGACCTGAAGCGAGAGGGGCGCCCCTTGCCAGAGG
GGGGCAGACAGCCCCCTATCGACTTCCGCGACGTGGACATCGGCGAGCT
GAGCAGCGACGTCATCTCCAACATCGAGACCTTCGATGTCAACGAGTTT
GACCAGTACCTGCCGCCCAACGGCCACCCGGGGGTGCCGGCCACGCACG
GCCAGGTCACCTACACGGGCAGCTACGGCATCAGCAGCACCGCGGCCAC
CCCGGCGAGCGCGGGCCACGTGTGGATGTCCAAGCAGCAGGCGCCGCCG
CCACCCCCGCAGCAGCCCCACAGGCCCCGCCGGCCCCGCAGGCGCCCC
CGCAGCCGCAGGCGGCGCCCCACAGCAGCCGGCGGCACCCCCGCAGCA
GCCACAGGCGCACACGCTGACCACGCTGAGCAGCGAGCCGGGCCAGTCC
CAGCGAACGCACATCAAGACGGAGCAGCTGAGCCCCAGCCACTACAGCG
AGCAGCAGCAGCACTCGCCCCAACAGATCGCCTACAGCCCCTTCAACCT
CCCACACTACAGCCCCTCCTACCCGCCCATCACCCGCTCACAGTACGAC
TACACCGACCACCAGAACTCCAGCTCCTACTACAGCCACGCGGCAGGCC
AGGGCACCGGCCTCTACTCCACCTTCACCTACATGAACCCCGCTCAGCG
CCCCATGTACACCCCCATCGCCGACACCTCTGGGGTCCCTTCCATCCCG
CAGACCCACAGCCCCAGCACTGGGAACAACCCGTCTACACACAGCTCA
CTCGACCT

Nucleic acid sequence encoding NKX6.2:
(SEQ ID NO: 3)
ATGGACACTAACCGCCCGGGCGCGTTCGTGCTGAGCAGTGCCCCGCTGG
CCGCGCTGCACAACATGGCCGAGATGAAGACGTCGCTGTTCCCCTACGC
GCTGCAGGGTCCGGCCGGCTTCAAGGCGCCCGCGCTGGGGGGCCTGGGC
GCGCAGCTCCCGCTCGGGACCCCGCACGGCATCAGCGACATCCTGGGCC
GGCCCGTGGGCGCGGCGGGCGGGGGCCTCCTGGGGGGCTGCCCCGGCT
CAACGGGCTCGCGTCGTCCGCCGGCGTTTACTTCGGGCCCGCGGCCGCT
GTGGCGCGGCTACCCCAAGCCCCTGGCCGAGCTGCCGGGGCGCCCGC CCATCTTCTGGCCCGGCGTGGTGCAGGGCGCGCCCTGGAGGGACCCGCG
TCTGGCTGGCCCGGCCCCGGCCGGCGGCGTCCTGGACAAGGACGGGAAG
AAGAAGCACTCGCGCCCGACCTTCTCGGGCCAGCAGATCTTCGCGCTGG
AGAAAACCTTCGAGCAGACCAAGTACCTGGCGGGCCCGGAGCGCGCGCG
TCTCGCCTACTCGCTGGGCATGACCGAGAGCCAGGTGAAGGTCTGGTTC
CAGAACCGCCGGACCAAGTGGCGCAAGCGGCACGCGGTGGAGATGGCGT
CGGCCAAGAAGAAGCAGGACTCGGACGCCGAGAAGCTGAAGGTGGGCGG
CTCGGACGCGGAGGACGACGACGAATACAACCGGCCCCTGGACCCCAAC
TCGGACGACGAGAAGATCACGCGGCTGCTCAAGAAGCACAAACCCTCGA
ACTTGGCGCTGGTCAGCCCGTGCGGCGGCGGCGGGGGGACGCCTTG Nucleic acid sequence encoding OLIG2:
(SEQ ID NO: 4)
ATGGACTCGGACGCCAGCCTGGTGTCCAGCCGCCCGTCGTCGCCAGAGC
CCGATGACCTTTTTCTGCCGGCCCGGAGTAAGGGCAGCAGCGGCAGCGC
CTTCACTGGGGGCACCGTGTCCTCGTCCACCCCGAGTGACTGCCCGCCG
GAGCTGAGCGCCGAGCTGCGCGGCGCTATGGGCTCTGCGGGCGCGCATC
CTGGGGACAAGCTAGGAGGCAGTGGCTTCAAGTCATCCTCGTCCAGCAC
CTCGTCGTCTACGTCGTCGGCGGCTGCGTCGTCCACCAAGAAGGACAAG
AAGCAAATGACAGAGCCGGAGCTGCAGCAGCTGCGTCTCAAGATCAACA
GCCGCGAGCGCAAGCGCATGCACGACCTCAACATCGCCATGGATGGCCT
CCGCGAGGTCATGCCGTACGCACACGGCCCTTCGGTGCGCAAGCTTTCC
AAGATCGCCACGCTGCTGCTGGCGCGCAACTACATCCTCATGCTCACCA
ACTCGCTGGAGGAGATGAAGCGACTGGTGAGCGAGATCTACGGGGCCA
CCACGCTGGCTTCCACCCGTCGGCCTGCGGCGGCCTGGCGCACTCCGCG
CCCCTGCCCGCCGCCACCGCGCACCCGGCAGCAGCGCACGCCGCAC
ATCACCCCGCGGTGCACCACCCCATCCTGCCGCCCGCCGCCGCAGCGGC
TGCTGCCGCCGCTGCAGCCGCGGCTGTGTCCAGCGCCTCTCTGCCCGGA
TCCGGGCTGCCGTCGGTCGGCTCCATCCGTCCACCGCACGGCCTACTCA
AGTCTCCGTCTGCTGCCGCGGCCGCCCCGCTGGGGGGCGGGGCGGCGG
CAGTGGGGCGAGCGGGGCTTCCAGCACTGGGGCGGCATGCCCTGCCCC
TGCAGCATGTGCCAGGTGCCGCCGCCGCACCACCACGTGTCGGCTATGG
GCGCCGGCAGCCTGCCGCGCCTCACCTCCGACGCCAAG Nucleic acid sequence encoding OCT4:
(SEQ ID NO: 5)
ATGGCGGGACACCTGGCTTCAGATTTTGCCTTCTCGCCCCCTCCAGGTG
GTGGAGGTGATGGGCCAGGGGGGCCGGAGCCGGGCTGGGTTGATCCTCG
GACCTGGCTAAGCTTCCAAGGCCCTCCTGGAGGGCAGGAATCGGGCCG
GGGGTTGGGCCAGGCTCTGAGGTGTGGGGGATTCCCCCATGCCCCCCGC
CGTATGAGTTCTGTGGGGGGATGGCGTACTGTGGGCCCCAGGTTGGAGT
GGGGCTAGTGCCCCAAGGCGGCTTGGAGACCTCTCAGCCTGAGGGCGAA
GCAGGAGTCGGGGTGGAGAGCAACTCCGATGGGGCCTCCCCGGAGCCCT
GCACCGTCACCCCTGGTGCCGTGAAGCTGGAGAAGGAGAAGCTGGAGCA
AAACCCGGAGGAGTCCCAGGACATCAAAGCTCTGCAGAAAGAACTCGAG -continued

```
CAATTTGCCAAGCTCCTGAAGCAGAAGAGGATCACCCTGGGATATACAC

AGGCCGATGTGGGGCTCACCCTGGGGGTTCTATTTGGGAAGGTATTCAG

CCAAACGACCATCTGCCGCTTTGAGGCTCTGCAGCTTAGCTTCAAGAAC

ATGTGTAAGCTGCGGCCCTTGCTGCAGAAGTGGGTGGAGGAAGCTGACA

ACAATGAAATCTTCAGGAGATATGCAAAGCAGAAACCCTCGTGCAGGC

CCGAAAGAGAAAGCGAACCAGTATCGAGAACCGAGTGAGAGGCAACCTG

GAGAATTTGTTCCTGCAGTGCCCGAAACCCACACTGCAGCAGATCAGCC

ACATCGCCCAGCAGCTTGGGCTCGAGAAGGATGTGGTCCGAGTGTGGTT

CTGTAACCGGCGCCAGAAGGGCAAGCGATCAAGCAGCGACTATGCACAA

CGAGAGGATTTTGAGGCTGCTGGGTCTCCTTTCTCAGGGGGACCAGTGT

CCTTTCCTCTGGCCCCAGGGCCCCATTTTGGTACCCCAGGCTATGGGAG

CCCTCACTTCACTGCACTGTACTCCTCGGTCCCTTTCCCTGAGGGGGAA

GCCTTTCCCCCTGTCTCTGTCACCACTCTGGGCTCTCCCATGCATTCAA

ACTGA
```

Amino acid sequence encoding NKX6.1:

(SEQ ID NO: 6)

```
MLAVGAMEGTRQSAFLLSSPPLAALHSMAEMKTPLYPAAYPPLPAGPPS

SSSSSSSSSSPSPPLGTHNPGGLKPPATGGLSSLGSPPQQLSAATPHGI

NDILSRPSMPVASGAALPSASPSGSSSSSSSSASASSASAAAAAAAAAA

AAASSPAGLLAGLPRFSSLSPPPPPPGLYFSPSAAAVAAVGRYPKPLAE

LPGRTPIFWPGVMQSPPWRDARLACTPHQGSILLDKDGKRKHTRPTFSG

QQIFALEKTFEQTKYLAGPERARLAYSLGMTESQVKVWFQNRRTKWRKK

HAAEMATAKKKQDSETERLKGASENEEEDDDYNKPLDPNSDDEKITQLL

KKHKSSSGGGGLLLHASEPESSS
```

Amino acid sequence encoding SOX9:

(SEQ ID NO: 7)

```
MNLLDPFMKMTDEQEKGLSGAPSPTMSEDSAGSPCPSGSGSDTENTRPQ

ENTFPKGEPDLKKESEEDKFPVCIREAVSQVLKGYDWTLVPMPVRVNGS

SKNKPHVKRPMNAFMVWAQAARRKLADQYPHLHNAELSKTLGKLWRLLN

ESEKRPFVEEAERLRVQHKKDHPDYKYQPRRRKSVKNGQAEAEEATEQT

HISPNAIFKALQADSPHSSSGMSEVHSPGEHSGQSQGPPTPPTTPKTDV

QPGKADLKREGRPLPEGGRQPPIDFRDVDIGELSSDVISNIETFDVNEF

DQYLPPNGHPGVPATHGQVTYTGSYGISSTAATPASAGHVWMSKQQAPP

PPPQQPPQAPPAPQAPPQPQAAPPQQPAAPPQQPQAHTLTTLSSEPGQS

QRTHIKTEQLSPSHYSEQQQHSPQQIAYSPFNLPHYSPSYPPITRSQYD

YTDHQNSSSYYSHAAGQGTGLYSTFTYMNPAQRPMYTPIADTSGVPSIP

QTHSPQHWEQPVYTQLTRP
```

Amino acid sequence encoding NKX6.2:

(SEQ ID NO: 8)

```
MDTNRPGAFVLSSAPLAALHNMAEMKTSLFPYALQGPAGFKAPALGGLG

AQLPLGTPHGISDILGRPVGAAGGGLLGGLPRLNGLASSAGVYFGPAAA

VARGYPKPLAELPGRPPIFWPGVVQGAPWRDPRLAGPAPAGGVLDKDGK

KKHSRPTFSGQQIFALEKTFEQTKYLAGPERARLAYSLGMTESQVKVWF

QNRRTKWRKRHAVEMASAKKKQDSDAEKLKVGGSDAEDDDEYNRPLDPN

SDDEKITRLLKKHKPSNLALVSPCGGGAGDAL
```

Amino acid sequence encoding OLIG2:

(SEQ ID NO: 9)

```
MDSDASLVSSRPSSPEPDDLFLPARSKGSSGSAFTGGTVSSSTPSDCPP

ELSAELRGAMGSAGAHPGDKLGGSGFKSSSSSTSSSTSSAAASSTKKDK

KQMTEPELQQLRLKINSRERKRMHDLNIAMDGLREVMPYAHGPSVRKLS

KIATLLLARNYILMLTNSLEEMKRLVSEIYGGHHAGFHPSACGGLAHSA

PLPAATAHPAAAAHAAHHPAVHHPILPPAAAAAAAAAAAAVSSASLPG

SGLPSVGSIRPPHGLLKSPSAAAAAPLGGGGGGSGASGGFQHWGGMPCP

CSMCQVPPPHHHVSAMGAGSLPRLTSDAK
```

Amino acid sequence encoding OCT4:

(SEQ ID NO: 10)

```
MAGHLASDFAFSPPPGGGGDGPGGPEPGWVDPRTWLSFQGPPGGPGIGP

GVGPGSEVWGIPPCPPPYEFCGGMAYCGPQVGVGLVPQGGLETSQPEGE

AGVGVESNSDGASPEPCTVTPGAVKLEKEKLEQNPEESQDIKALQKELE

QFAKLLKQKRITLGYTQADVGLTLGVLFGKVFSQTTICRFEALQLSFKN

MCKLRPLLQKWVEEADNNENLQEICKAETLVQARKRKRTSIENRVRGNL

ENLFLQCPKPTLQQISHIAQQLGLEKDVVRVWFCNRRQKGKRSSSDYAQ

REDFEAAGSPFSGGPVSFPLAPGPHFGTPGYGSPHFTALYSSVPFPEGE

AFPPVSVTTLGSPMHSN
```

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

What is claimed is:

1. A method comprising:
introducing into pluripotent stem cells at least four transcription factors selected from (a) oligodendrocyte 2 (OLIG2), (b) SRY-box 9 (SOX9), (c) NKX homeobox 6.1 (NKX6.1), (d) NKX homeobox 6.2 (NKX6.2), and (e) octamer-binding 4 (OCT4),
culturing the pluripotent stem cells; and
inducing the pluripotent stem cells to produce a population of cells comprising oligodendrocyte progenitor cells (OPCs), wherein the pluripotent stem cells produce the population of cells comprising OPCs within 30 days of the inducing.

2. The method of claim 1, further comprising culturing the OPCs with another cell type to produce a myelinated organoid.

3. The method of claim 1, wherein each of the at least four transcription factors is introduced on an engineered nucleic acid comprising a nucleotide sequence encoding the respective transcription factor.

4. The method of claim 3, wherein at least two of the at least four transcription factors are encoded by the same engineered nucleic acid.

5. The method of claim 1, wherein OLIG2, OCT4, SOX9, NKX6.1, and NKX6.2 are introduced into the pluripotent stem cells.

6. The method of claim 1, wherein at least 20% of the cells of the population of cells comprising OPCs express O4.

7. The method of claim 6, wherein at least 20% of the cells of the population of cells comprising OPCs express O4 within four days following the inducing.

8. The method of claim 7, wherein at least 40% of the cells of the population of cells comprising OPCs express O4 within four days following the inducing.

9. The method of claim 1, wherein the culturing comprises culturing the pluripotent stem cells for 1 to 10 days.

10. The method of claim 1, wherein at least one engineered nucleic acid encoding a cytokine selected from IL-10 and IFNβ is introduced into the pluripotent stem cells.

11. The method of claim 10, wherein the population of cells comprising OPCs secrete IL-10, within three, four, five or seven days following the inducing.

12. The method of claim 11, wherein a level of IL-10 secreted by the population of cells comprising OPCs is at least 50-fold higher than control cells, wherein the control cells are (a) naturally occurring OPCs, (b) OPCs that are not engineered to express IL-10, and/or (c) OPCs that are engineered to express IL-10 under an inducible promoter and are cultured in the absence of an inducing agent.

13. The method of claim 2, wherein each transcription factor is introduced on an engineered nucleic acid comprising a nucleotide sequence encoding the transcription factor.

14. The method of claim 13, wherein at least two of the at least four transcription factors are encoded by the same engineered nucleic acid.

15. The method of claim 1, wherein each of the at least four transcription factors is encoded by a coding sequence operably linked to an inducible promoter.

16. The method of claim 1, wherein the at least four transcription factors comprise OCT4, OLIG2, NKX6.1, and SOX9.

17. The method of claim 1, wherein the at least four transcription factors comprise OCT4, OLIG2, NKX6.2, and SOX9.

18. The method of claim 1, wherein the at least four transcription factors comprise OLIG2, SOX9, NKX6.1, and NKX6.2.

19. The method of claim 1, wherein the at least four transcription factors comprise OCT4, OLIG2, NKX6.1, and NKX6.2.

\* \* \* \* \*

SEQUENCE LISTING

Sequence total quantity: 10
SEQ ID NO: 1           moltype = DNA   length = 1101
FEATURE                Location/Qualifiers
source                 1..1101
                       mol_type = genomic DNA
                       organism = Homo sapiens
SEQUENCE: 1
atgttagcgg tgggggcaat ggagggcacc cggcagagcg cattcctgct cagcagccct    60
cccctggccg ccctgcacag catggccgag atgaagaccc cgctgtaccc tgccgcgtat   120
ccccgctgc ctgccggccc ccctcctcc tcgtcctcgt cgtcgtcctc ctcgtcgccc    180
tcccgcctc tgggcaccca aacccaggc ggcctgaagc ccccggccac gggggggctc    240
tcatccctcg gcagccccc gcagcagctc tcggccgcca ccccacacgg catcaacgat    300
atcctgagcc ggccctccat gcccgtggcc tcggggggccg ccctgccctc cgcctcgccc  360
tccggttcct cctcctcctc ttcctcgtcc gcctctgcct cctccgcctc tgccgccgcc   420
gcggctgctg ccgcggccgc agccgccgcg tcatcccgcg ggggctgct ggccggactg    480
ccacgcttta gcagcctgag cccgccgccg ccgccgcccg gctctactt cagccccagc    540
gccgcggccg tggccgccgt gggccggtac cccaagccgc tggctgagct gcctggccgg   600
acgcccatct tctggcccgg agtgatgcag agcccgccct ggaggacgc acgcctggcc    660
tgtaccccctc atcaaggatc catttgttg gacaaagacg ggaagagaaa acacacgaga   720
cccactttt ccggacagca gatcttcgcc ctgagaagaa ctttcgaaca aacaaaatac    780
ttggcgggc cgagagggc tcgtttggcc tattcgttgg ggatgacaga gagtcaggtc    840
aaggtctggt tccagaaccg ccggaccaag tggaggaaga agcacgctgc cgagatggcc   900
acggccaaga agaagcagga ctcggagaca gagcgcctca aggggggcctc ggagaacgag  960
gaagaggacg acgactacaa taagcctctg gatcccaact cggacgacga gaaaatcacg  1020
cagctgttga agaagcacaa gtccagcagc ggcggcggcg gcggcctcct actgcacgcg  1080
tccgagccgg agagctcatc c                                            1101

SEQ ID NO: 2           moltype = DNA   length = 1527
FEATURE                Location/Qualifiers
source                 1..1527
                       mol_type = genomic DNA
                       organism = Homo sapiens
SEQUENCE: 2
atgaatctcc tggaccccctt catgaagatg accgacgagc aggagaaggg cctgtccggc    60
gccccagcc ccaccatgtc cgaggactcc gcgggctcgc cctgcccgtc gggctccggc   120
tcggacacga agaacacgcg gccccaggag aacacgttcc ccaagggcga gcccgatctg   180
aagaaggaga gcgaggagga caagttcccc gtgtgcatcc gcgaggcggt cagccaggtg   240
ctcaaaggct acgactggac gctggtgccc atgccggtgc gcgtcaacgg ctccagcaag   300
aacaagccgc acgtcaagcg gcccatgaac gccttcatgg tgtgggcgca ggcggcgcgc   360
aggaagctcg cggaccagta cccgcacttg cacaaccgcg agtcagcaa gacgctgggc   420
aagctctgga gacttctgaa cgagagcgag aagcggcccct tcgtggagga ggcggagcgg   480
ctgcgcgtgc agcacaagaa ggaccacccg gattacaagt accagccgcg gcggaggaag   540
tcggtgaaga cgggcaggc ggaggcagag gaggccacgg agcagacgca catctccccc    600
aacgccatct tcaaggcgct gcaggccgac tcgccacact cctcctccgg catgagcgag   660
gtgcactccc ccggcgagca ctcggggcaa tccagggcc caccgaccc acccaccacc    720
cccaaaaccg acgtgcagcc gggcaaggct gacctgaagc gagaggggcg ccccttgcca   780
gagggggga gacagcccccc tatcgacttc cgcgacgtgg acatcggcga gctgagcagc   840
gacgtcatct ccaacatcga gacctttcgat gtcaacgagt ttgaccagta cctgccgccc   900
aacggccacc cggggggtgcc ggccacgcac ggccaggtca cctacacggg cagctacggc   960
atcagcagca ccgcggccac cccggcgagc gcgggccacg tgtggatgtc aagcagcag  1020
gcgccgccgc caccccgca gcagccccca caggccccgc cggccccgca ggcgcccccg  1080
cagccgcagg cggccgcccc acagcagccg gcggcacccc cgcacgcagcc acagcgcgca  1140
acgctgacca cgctgagcag cgagccgggc cagtcccagc gaacgcacat caagacggag  1200
cagctgagcc ccagccacta cagcgagcag cagcagcact cgcccaaca gatcgctac   1260
agcccccttca acctcccaca ctacagcccc tcctacccgc ccatcacccg ctcacagtac  1320
gactacaccg accaccagaa ctccagctcc tactacagcc acgcggcagg ccagggcacc  1380
ggcctctact ccaccttcac ctacatgaac cccagctcag ccccatgta cccccatc   1440
gccgacacct ctggggtccc ttccatcccg cagacccaca gcccccagca ctgggaacaa  1500
cccgtctaca cacagctcac tcgacct                                      1527

SEQ ID NO: 3           moltype = DNA   length = 831
FEATURE                Location/Qualifiers
source                 1..831
                       mol_type = genomic DNA
                       organism = Homo sapiens
SEQUENCE: 3
atggacacta accgcccggg cgcgttcgtg ctgagcagtg ccccgctggc cgcgctgcac    60
aacatggccg agatgaagac gtcgctgttc ccctacgcgc tgcagggtcc ggccggcttc   120
aaggccccg cgctgggggg cctgggcgcg cagctcccgc tcgggacccc gcacggcatc   180
agcgacatcc tgggccggcc cgtgggcgcg gcgggccggg gcctcctggg ggggctgccc   240
cggctcaacg ggctcgcgtc gtcgccggc gtttacttcg ggcccgcggc cgctgtggcg   300
cgcggctacc ccaagcccct ggccgagctg ccggggcgcc cgcccatctt ctggcccggc   360
gtggtgcagg gcgcgcctg gaggggaccccg cgtgtggccg cccgggccgc   420
gtcctggaca aggacgggaa gaagagcac tcgcgccga ccttctcggg ccagcagatc    480
ttcgcgctgg agaaaacctt cgagcagacc aagtacctgg cgggcccgga gcgcgcgcgt   540
ctcgcctact cgctgggcat gaccgagagc caggtgaagg tctggttcca gaaccgccgg   600
accaagtggc gcaagcggca cgcggtggag atggcgtcg ccaagaagaa gcaggactcg   660
gacgccgaga agctgaaggt gggcggctcg gacgcgggag acgacgacga atacaaccgg   720

```
cccctggacc ccaactcgga cgacgagaag atcacgcggc tgctcaagaa gcacaaaccc    780
tcgaacttgg cgctggtcag cccgtgcggc ggcggcgcgg gggacgcctt g             831

SEQ ID NO: 4              moltype = DNA   length = 969
FEATURE                   Location/Qualifiers
source                    1..969
                          mol_type = genomic DNA
                          organism = Homo sapiens
SEQUENCE: 4
atggactcgg acgccagcct ggtgtccagc cgcccgtcgt cgccagagcc cgatgacctt    60
tttctgccgg cccggagtaa gggcagcagc ggcagcgcct tcactggggg caccgtgtcc    120
tcgtccaccc cgagtgactg cccgccggag ctgagcgccg agctgcgcgg cgctatgggc    180
tctgcgggcg cgcatcctgg ggacaagcta ggaggcagtg cgcttcaagtc atcctcgtcc    240
agcacctcgt cgtctacgtc gtcggcggct gcgtcgtcca ccaagaagga caagaagcgc    300
atgacagagc cggagctgca gcagctgcgt ctcaagatca cagccgcga gcgcaagcgc    360
atgcacgacc tcaacatcgc catggatggc tccgcgagg tcatgccgta cgcacacggc    420
ccttcggtgc gcaagctttc caagatcgcc acgctgctgc tggcgcgcaa ctacatcctc    480
atgctcacca actcgctgga ggagatgaag cgactgctgc gagatcta cgggggccac    540
cacgctggct tccacccgtc ggcctgcggc ggcctggcgc actccgcgcc cctgcccgcc    600
gccaccgcgc acccggcagc agcagcgcac gccgcacatc accccgcggt gcaccacccc    660
atcctgccgc ccgccgccgc agcggctgct gccgccgctg cagccgcggc tgtgtccagc    720
gcctctctgc ccggatccgg gctgccgtcg gtcggctcca tccgtccacc gcacggccta    780
ctcaagtctc cgtctgctgc gcggccgcc ccgctgggg gcgggggcgg cggcagtggg    840
gcgagcgggg gcttccagca ctggggcgg atgcccgcc cctgcagcat gtgccaggtg    900
ccgccgccgc accaccacgt gtcggctatg ggcgccggca gctgccgcg cctcacctcc    960
gacgccaag                                                            969

SEQ ID NO: 5              moltype = DNA   length = 1083
FEATURE                   Location/Qualifiers
source                    1..1083
                          mol_type = genomic DNA
                          organism = Homo sapiens
SEQUENCE: 5
atggcgggac acctggcttc agattttgcc ttctcgcccc ctccaggtgg tggaggtgat    60
gggccaggggg ggccggagcc gggctgggtt gatcctcgga cctgggcag cttccaaggc    120
cctcctggag ggccaggaat cgggccgggg gttgggccag gctctgaggt gtggggatt    180
cccccatgcc ccccgccgta tgagttctgt gggggggatgg cgtactgtgg gccccaggtt    240
ggagtggggc tagtgcccca aggcggcttg agacctctc agcctgaggg cgaagcagga    300
gtcggggtgg agagcaactc cgatggggcc tccccggacc cctgcaccgt cacccctggt    360
gccgtgaagc tggagaagga aagctggag caaaacccgg aggagtccca ggacatcaaa    420
gctctgcaga aagaactcga gcaatttgcc aagctcctga gcagaagag gatcaccctg    480
ggatatacac aggccgatgt ggggctcacc ctggggggttc tatttgggaa ggtattcagc    540
caaacgacca tctgccgctt tgaggtctgt cagcttagct tcaagaacat gtgtaagctg    600
cggcccttgc tgcagaagtg ggtggaggaa gctgacaaca atgaaaatct tcaggagata    660
tgcaaagcag aaaccctcgt gcaggcccga aagagaaagc gaaccagtat cgagaaccga    720
gtgagaggca acctggagaa tttgttcctg cagtgcccga acccacact gcagcagatc    780
agccacatcg cccagcagct tgggctcgag aaggatgtgg tccgagtgtg gttctgtaac    840
cggcgccaga agggcaagcg atcaagcagc gactatgcac aacgagagga ttttgaggct    900
gctgggtctc ctttctcagg gggaccagtg tcctttcctc tggccccagg gcccattttt    960
ggtaccccag gctatgggag ccctcacttc actgcactgt actcctcggt ccctttccct    1020
gagggggaag cctttccccc tgtctctgtc accactctgg gctctcccat gcattcaaac    1080
tga                                                                  1083

SEQ ID NO: 6              moltype = AA    length = 367
FEATURE                   Location/Qualifiers
source                    1..367
                          mol_type = protein
                          organism = Homo sapiens
SEQUENCE: 6
MLAVGAMEGT RQSAFLLSSP PLAALHSMAE MKTPLYPAAY PPLPAGPPSS SSSSSSSSP    60
SPPLGTHNPG GLKPPATGGL SSLGSPPQQL SAATPHGIND ILSRPSMPVA SGAALPSASP   120
SGSSSSSSSS ASASSASAAA AAAAAAAAAA SSPAGLLAGL PRFSSLSPPP PPPGLYFSPS   180
AAAVAAVGRY PKPLAELPGR TPIFWPGVMQ SPPWRDARLA CTPHQGSILL DKDGKRKHTR   240
PTFSGQQIFA LEKTFEQTKY LAGPERARLA YSLGMTESQV KVWFQNRRTK WRKKHAAEMA   300
TAKKKQDSET ERLKGASENE EEDDDYNKPL DPNSDDEKIT QLLKKHKSSS GGGGGLLLHA   360
SEPESSS                                                              367

SEQ ID NO: 7              moltype = AA    length = 509
FEATURE                   Location/Qualifiers
source                    1..509
                          mol_type = protein
                          organism = Homo sapiens
SEQUENCE: 7
MNLLDPFMKM TDEQEKGLSG APSPTMSEDS AGSPCPSGSG SDTENTRPQE NTFPKGEPDL    60
KKESEEDKFP VCIREAVSQV LKGYDWTLVP MPVRVNGSSK NKPHVKRPMN AFMVWAQAAR   120
RKLADQYPHL HNAELSKTLG KLWRLLNESE KRPFVEEAER LRVQHKKDHP DYKYQPRRRK   180
SVKNGQAEAE EATEQTHISP NAIFKALQAD SPHSSSGMSE VHSPGEHSGQ SQGPPTPPTT   240
PKTDVQPGKA DLKREGRPLP EGGRQPPIDF RDVDIGELSS DVISNIETFD VNEFDQYLPP   300
NGHPGVPATH GQVTYTGSYG ISSTAATPAS AGHVWMSKQQ APPPPPQQPP QAPPAPQAPP   360
```

```
QPQAAPPQQP AAPPQQPQAH TLTTLSSEPG QSQRTHIKTE QLSPSHYSEQ QQHSPQQIAY      420
SPFNLPHYSP SYPPITRSQY DYTDHQNSSS YYSHAAGQGT GLYSTFTYMN PAQRPMYTPI      480
ADTSGVPSIP QTHSPQHWEQ PVYTQLTRP                                       509

SEQ ID NO: 8            moltype = AA  length = 277
FEATURE                 Location/Qualifiers
source                  1..277
                        mol_type = protein
                        organism = Homo sapiens
SEQUENCE: 8
MDTNRPGAFV LSSAPLAALH NMAEMKTSLF PYALQGPAGF KAPALGGLGA QLPLGTPHGI       60
SDILGRPVGA AGGGLLGGLP RLNGLASSAG VYFGPAAAVA RGYPKPLAEL PGRPPIFWPG      120
VVQGAPWRDP RLAGPAPAGG VLDKDGKKKH SRPTFSGQQI FALEKTFEQT KYLAGPERAR      180
LAYSLGMTES QVKVWFQNRR TKWRKRHAVE MASAKKKQDS DAEKLKVGGS DAEDDDEYNR      240
PLDPNSDDEK ITRLLKKHKP SNLALVSPCG GGAGDAL                              277

SEQ ID NO: 9            moltype = AA  length = 323
FEATURE                 Location/Qualifiers
source                  1..323
                        mol_type = protein
                        organism = Homo sapiens
SEQUENCE: 9
MDSDASLVSS RPSSPEPDDL FLPARSKGSS GSAFTGGTVS SSTPSDCPPE LSAELRGAMG       60
SAGAHPGDKL GGSGFKSSSS STSSSTSSAA ASSTKKDKKQ MTEPELQQLR LKINSRERKR      120
MHDLNIAMDG LREVMPYAHG PSVRKLSKIA TLLLARNYIL MLTNSLEEMK RLVSEIYGGH      180
HAGFHPSACG GLAHSAPLPA ATAHPAAAAH AAHHPAVHHP ILPPAAAAAA AAAAAAVSS       240
ASLPGSGLPS VGSIRPPHGL LKSPSAAAAA PLGGGGGSG ASGGFQHWGG MPCPCSMCQV       300
PPPHHHVSAM GAGSLPRLTS DAK                                             323

SEQ ID NO: 10           moltype = AA  length = 360
FEATURE                 Location/Qualifiers
source                  1..360
                        mol_type = protein
                        organism = Homo sapiens
SEQUENCE: 10
MAGHLASDFA FSPPPGGGGD GPGGPEPGWV DPRTWLSFQG PPGGPGIGPG VGPGSEVWGI       60
PPCPPPYEFC GGMAYCGPQV GVGLVPQGGL ETSQPEGEAG VGVESNSDGA SPEPCTVTPG      120
AVKLEKEKLE QNPEESQDIK ALQKELEQFA KLLKQKRITL GYTQADVGLT LGVLFGKVFS      180
QTTICRFEAL QLSFKNMCKL RPLLQKWVEE ADNNENLQEI CKAETLVQAR KRKRTSIENR      240
VRGNLENLFL QCPKPTLQQI SHIAQQLGLE KDVVRVWFCN RRQKGKRSSS DYAQREDFEA      300
AGSPFSGGPV SFPLAPGPHF GTPGYGSPHF TALYSSVPFP EGEAFPPVSV TTLGSPMHSN      360
```